US006699704B1

(12) United States Patent
van Loon et al.

(10) Patent No.: US 6,699,704 B1
(45) Date of Patent: Mar. 2, 2004

(54) HEAT TOLERANT PHYTASES

(75) Inventors: Adolphus van Loon, Rheinfelden (CH); David Mitchell, Aesch (CH)

(73) Assignee: Roche Vitamins Inc., Parsippany, NJ (US)

( * ) Notice: Subject to any disclaimer, the term of this patent is extended or adjusted under 35 U.S.C. 154(b) by 355 days.

(21) Appl. No.: 09/635,504

(22) Filed: Aug. 9, 2000

Related U.S. Application Data

(63) Continuation of application No. 08/868,435, filed on Jun. 3, 1997, now Pat. No. 6,291,221, which is a division of application No. 08/744,231, filed on Nov. 5, 1996, now Pat. No. 6,358,722, which is a continuation-in-part of application No. 08/424,757, filed on Apr. 18, 1995, now abandoned.

(30) Foreign Application Priority Data

Apr. 25, 1994 (EP) ............................................. 94810228

(51) Int. Cl.[7] ............................ C12N 9/16; C12N 1/20; C12N 1/15; C12N 1/19; C12N 15/74

(52) U.S. Cl. ............... 435/252.3; 435/196; 435/254.11; 435/254.2; 435/320.1; 435/18; 435/69.1; 435/255.1; 435/325; 536/23.2

(58) Field of Search .............................. 435/196, 252.3, 435/18, 69.1, 325, 320.1, 254.11, 254.2, 255.1; 536/23.2

(56) References Cited

U.S. PATENT DOCUMENTS

| | | |
|---|---|---|
| 5,436,156 A | 7/1995 | Van Gorcom et al. |
| 5,443,979 A | 8/1995 | Vanderbeke et al. |
| 5,863,533 A | 1/1999 | Van Gorcom et al. |
| 6,153,418 A | 11/2000 | Lehmann |
| 6,291,221 B1 | 9/2001 | Van Loon et al. |
| 6,358,722 B1 | 3/2002 | Van Loon et al. |
| 6,391,605 B1 | 5/2002 | Kostrewa et al. |

FOREIGN PATENT DOCUMENTS

| | | |
|---|---|---|
| DE | 1 492 060 | 3/1969 |
| EP | 0 035 204 A2 | 9/1981 |
| EP | 420 358 | 4/1991 |
| EP | 0 422 697 A1 | 4/1991 |
| EP | 299 108 | 5/1994 |
| EP | 0 619 369 | 10/1994 |
| EP | 684 313 | 11/1995 |
| EP | 747 483 | 12/1996 |
| EP | 0 758 018 A1 | 2/1997 |
| EP | 0 897 010 A2 | 2/1999 |
| EP | 0 897 985 A2 | 2/1999 |
| NZ | 235 478 | 9/1990 |
| WO | WO 91/14773 | 10/1991 |
| WO | WO 93/16175 | 8/1993 |
| WO | WO 94/03072 | 2/1994 |
| WO | WO 94/03612 | 2/1994 |
| WO | WO 95/00662 | 1/1995 |
| WO | WO 98/54980 | 12/1998 |

OTHER PUBLICATIONS

Bork, Genome Research, 10:398–400, 2000.*

(List continued on next page.)

*Primary Examiner*—Rebecca E. Prouty
*Assistant Examiner*—Delia Ramirez
(74) *Attorney, Agent, or Firm*—Bryan Cave LLP

(57) ABSTRACT

The present invention relates to heat tolerant phytases and DNA sequences which code therefor. The phytases are useful in hydrolyzing phytate to inositol and inorganic phosphates. The phytases are valuable feed additives.

24 Claims, 32 Drawing Sheets

OTHER PUBLICATIONS

Broun et al., Science 282:1315–1317, 1998.*
Van de Loo et al., Proc. Natl. Acad. Sci. 92:6743–6747, 1995.*
Seffernick et al., J. Bacteriol. 183(8):2405–2410, 2001.*
van Hartingsveldt et al., GenBank accession No. Z16414, 1992.*
Shieh and Ware, Appl. Microbiol. vol. 16, pp. 1348–1351 (1968).
Janecek, S., Process Biochem., vol. 28, pp. 435–445 (1993).
Fersht, A.R and Serrano, L., Curr. Opin. Struct. Biol., vol. 3, pp. 75–83 (1993).
Alber, T., Annu. Rev. Biochem., vol. 58, pp. 765–798 (1989).
Matthews, B.W., Biochemistry, vol. 26, pp. 6885–6888 (1987).
Matthews, B.W., Curr. Opin. Struct. Biol., vol. 1, pp. 17–21 (1991).
Pen, et al., Bio/Technology, vol. 11, pp. 811–814 (1994).
Stuber, et al., Immunological Methods, eds. Lefkovits and Pernis, Academic Press Inc., vol. IV, pp. 121–152 (1990).
Serrano, L. et al., J. Mol. Biol., vol. 223, pp. 305–312 (1993).
Steipe, B., et al., J. Mol. Biol., vol. 240, pp. 188–192 (1994).
Dox, et al., J. Biol. Chem., vol. 10, pp. 183–186 (1911).
Howson, et al., Enzyme Microb. Technol., vol. 5, pp. 377–382 (1983).
Lambrechts, et al., Biotech, Lett., vol. 14, No. 1, pp. 61–66 (1992).
Van Hartingsveldt, et al., Gene, vol. 127, pp. 87–94 (1993).
Piddington, et al., Gene, vol. 133, pp. 55–62 (1993).
Kraulis, P.J., Appl. Cryst., vol. 24, pp. 946–950 (1991).
Merrit, et al., Acta Cryst., pp. 869–873 (1994).
Wodzinzki, et al., Advances in Applied Microbiology, vol. 42, pp. 263–303 (1996).
Mitchell, et al., Microbiology, vol. 143, pp. 245–252 (1997).
Kostrewa, et al., Nature Structural Biology, vol. 4, pp. 185–190 (1997).
Simons, et al., Br. J. Nutr., vol. 64, pp. 525–540 (1990).
Schoner, et al., J. Anim. Physiol. a. Anim. Nutr., vol. 66, pp. 248–255 (1991).
Jongbloed, et al., J. Anim Sci., vol. 70, pp. 1159–1168 (1992).
Perney, et al., Poultry Sci., vol. 72, pp. 2106–2114 (1993).
Ferrell, et al., J. Anim. Physiol. a. Anim. Nutr., vol. 69, pp. 278–283 (1993).
Broz, et al., Br. Poultry Sci., vol. 35, pp. 273–280 (1994).
Dungelhoef, et al., Animal Feed Sci. Technol., vol. 49, pp. 1–10 (1994).
Piccotti, et al., J. Immunol., pp. 643–648 (1997).
Presentation by Dr. Luis Pasamontes at the Institute of Med. Microbiologie, Basel, Switzerland, Feb. 11, 1997.
Mullaney, et al., Appl. Microbiol Biotechnol., vol. 35, pp. 611–614 (1991).
Conneely, O.M., Biotechology in the Feed Industry, T.P. Lyons (ed.), Alltech Technical Publications, Nicholasville, KY, pp. 57–66 (1992).
R.F. Doolittle., et al., The Proteins, Neurath, et al. editors, Academic Press, New York, pp. 14 (1979).
Nunes, C.S., Biol. Abstr., vol. 98 Ref. No. 126043 (1994).
Segueilha, et al., J. Fermentation and Bioeng., vol. 74 (1), pp. 7–11 (1992).
Suzuki, et al., Bull. Coll. Agr., Tokyo Imp. Univ., vol. 7, pp. 495 (1907).
Yamada, et al., Agr. Biol. Chem., vol. 32, pp. 1275–1282 (1968).
Lee, C., et al., Science, vol. 239, pp. 1288–1291 (1988).
Yamamoto, et al., Agr. Biol. Chem. vol. 36 (12), pp. 2097–2103 (1972).
Ullah, et al., "Identification of Active–Site Residues in Aspergillus ficuum Extracellular pH 2.5 Optimum Acid Phosphatase," Biochemical and Biophysical Research Communications, vol. 192, No. 2, pp. 754–759 (1993).
Khare, et al., "Entrapment of Wheat Phytase in Polyacrylamide Gel and its Application in Soymilk Phytase Hydrolysis," Biotechnol. Appl. Biochem. vol. 19, pp. 193–198 (1994).
Derwent English language abstract of DE 1 492 060 (document B15) (1969).
Derwent accession No. XP–002120048, English language abstract of JP 09065877 (1997).

* cited by examiner

```
tctagaacaataacaggtactccctaggtacccgaaggaccttgtggaaaatgtatggag      60
gtggacacggcaccaaccaccacccgcgatggcgcacgtggtgccctaaccccttgctcc    120
ctcaggatggaatccatgtcgactctttaccctcaccatcgcctggatgaaacctccccg    180
ctaagctcacgacgatcgctatttccgaccgatttgaccgtcatggtggagggctgattc    240
ggtcgatgctcctgccttcatttcggagttcggagacatgaaaggcttatatgaggacgt    300
cccaggtcggggacgaaatccgccctgggctgtgctccttcgtcggaaacatctgctgtc    360
cgtgatggctaccatgggctttcttgccattgtgctctccgtcgccttgctctttagaag    420
              M  G  F  L  A  I  V  L  S  V  A  L  L  F  R  S    16 gtatgcacccctctacgtccaattctctgggcactgacaacggcgcagcacatcgggcac    480
                                                    T  S  G  T    20 cccgttgggccccgggggcaaacatagcgactgcaactcagtcgatcacggctatcaatg    540
P  L  G  P  R  G  K  H  S  D  C  N  S  V  D  H  G  Y  Q  C       40 cttcctgaactctctcataaatggggactctacgcgcctacttctccctccaggacga     600
F  P  E  L  S  H  K  W  G  L  Y  A  P  Y  F  S  L  Q  D  E       60 gtctccgtttcctctggacgtcccagaggactgtcacatcaccttcgtgcaggtgctggc    660
S  P  F  P  L  D  V  P  E  D  C  H  I  T  F  V  Q  V  L  A       80 ccgccacggcgcgcggagcccaacccatagcaagaccaaggcgtacgcggcgaccattgc    720
R  H  G  A  R  S  P  T  H  S  K  T  K  A  Y  A  A  T  I  A      100 ggccatccagaagagtgccactgcgtttccgggcaaatacgcgttcctgcagtcatataa    780
A  I  Q  K  S  A  T  A  F  P  G  K  Y  A  F  L  Q  S  Y  N      120 ctactccttggactctgaggagctgactcccttcgggcggaaccagctgcgagatctggg    840
Y  S  L  D  S  E  E  L  T  P  F  G  R  N  Q  L  R  D  L  G      140 cgcccagttctacgagcgctacaacgccctcacccgacacatcaaccccttcgtccgcgc    900
A  Q  F  Y  E  R  Y  N  A  L  T  R  H  I  N  P  F  V  R  A      160 caccgatgcatcccgcgtccacgaatccgccgagaagttcgtcgagggcttccaaaccgc    960
T  D  A  S  R  V  H  E  S  A  E  K  F  V  E  G  F  Q  T  A      180 tcgacaggacgatcatcacgccaatccccaccagccttcgcctcgcgtggacgtggccat   1020
R  Q  D  D  H  H  A  N  P  H  Q  P  S  P  R  V  D  V  A  I      200 ccccgaaggcagcgcctacaacaacacgctggagcacagcctctgcaccgccttcgaatc   1080
P  E  G  S  A  Y  N  N  T  L  E  H  S  L  C  T  A  F  E  S      220 cagcaccgtcggcgacgacgcggtcgccaacttcaccgccgtgttcgcgccggcgatcgc   1140
S  T  V  G  D  D  A  V  A  N  F  T  A  V  F  A  P  A  I  A      240 ccagcgcctggaggccgatcttcccggcgtgcagctgtccaccgacgacgtggtcaacct   1200
Q  R  L  E  A  D  L  P  G  V  Q  L  S  T  D  D  V  V  N  L      260 gatggccatgtgtccgttcgagacggtcagcctgaccgacgacgcgcacacgctgtcgcc   1260
M  A  M  C  P  F  E  T  V  S  L  T  D  D  A  H  T  L  S  P      280 gttctgcgacctcttcacggccactgagtggacgcagtacaactacctgctctcgctgga   1320
F  C  D  L  F  T  A  T  E  W  T  Q  Y  N  Y  L  L  S  L  D      300 caagtactacggctacggcgggggcaatccgctgggtccggtgcaggggtcggctgggc   1380
K  Y  Y  G  Y  G  G  G  N  P  L  G  P  V  Q  G  V  G  W  A      320 gaacgagctgatggcgcggctaacgcgcgcccccgtgcacgaccacacctgcgtcaacaa   1440
N  E  L  M  A  R  L  T  R  A  P  V  H  D  H  T  C  V  N  N      340 caccctcgacgcgagtccggccaccttccccgctgaacgccaccctctacgccgacttctc   1500
T  L  D  A  S  P  A  T  F  P  L  N  A  T  L  Y  A  D  F  S      360
```

FIG. 1A

```
ccacgacagcaacctggtgtcgatcttctgggcgctgggcctgtacaacggcaccgcgcc 1560
 H  D  S  N  L  V  S  I  F  W  A  L  G  L  Y  N  G  T  A  P  380 gctgtcgcagacctccgtcgagagcgtctcccagacggacgggtacgccgccgcctggac 1620
 L  S  Q  T  S  V  E  S  V  S  Q  T  D  G  Y  A  A  A  W  T  400 ggtgccgttcgccgctcgcgcgtacgtcgagatgatgcagtgtcgcgccgagaaggagcc 1680
 V  P  F  A  A  R  A  Y  V  E  M  M  Q  C  R  A  E  K  E  P  420 gctggtgcgcgtgctggtcaacgaccgggtcatgccgctgcatggctgccctacggacaa 1740
 L  V  R  V  L  V  N  D  R  V  M  P  L  H  G  C  P  T  D  K  440 gctggggcggtgcaagcgggacgctttcgtcgcggggctgagctttgcgcaggcgggcgg 1800
 L  G  R  C  K  R  D  A  F  V  A  G  L  S  F  A  Q  A  G  G  460 gaactgggcggattgtttctgatgttgagaagaaaggtagatagataggtagtacatatg 1860
 N  W  A  D  C  F                                             466 gattgctcggctctgggtcgttgcccacaatgcatattacgcccgtcaactgccttgcgc 1920
catccacctctcaccctggacgcaaccgagcggtctaccctgcacacggcttccaccgcg 1980
acgcgcacggataaggcgcttttgttacggggttggggctgggggcagccggagccggag 2040
agagagaccagcgtgaaaaacgacagaacatagatatcaattcgacgccaattcatgcag 2100
agtagtatacagacgaactgaaacaaacacatcacttccctcgctcctctcctgtagaag 2160
acgctcccaccagccgcttctggcccttattcccgtacgctaggtagaccagtcagccag 2220
acgcatgcctcacaagaacgggggcggggacacactccgctcgtacagcacccacgacg 2280
tgtacaggaaaaccggcagcgccacaatcgtcgagagccatctgcag            2327
```

FIG. 1-B

```
gtcgacgaggcacaccacgcccgtcctcggcgggtccgagagggccggggctcgggttcga    60
caaggagacgggcgtcccttcgggcgcggctgcgggtgtgggtgttgctgtggacggtga   120
ggaggggggacgggctgggcgttgatgacggtacgaatgcgaacggacacaggccgctgag  180
cgtgggtgttgcgttctaatctttctttgtgtgggtgtgtacgtgtgggtgtgtatgtgt   240
ttggggggggaatgttcttggtaattatctttctacccttcttctctttcctttattct    300
gttcagcaggtatacccgtgtaagtgtacaggattatgggacgggtgggtggatggact    360
acttctagaaggacggataaggaaaaaggggaaacacgaatatggcgccctgggtggcgc   420
gtcgagctggatgcttgacgccggtctggcaaacattttcttcttctagcacccaaccta   480
gtacttgatagagtgtttcggggccaggcggtttgcgctgtgtttttaccaatcaccaac   540
tagtgctactactattattgcggctgttgatgcagccgtgtaccaaaaatgccgcggcat   600
ctccattgatacttgtagttttgatagatcaatatttgggaggttgcgctgggctgctct   660
gaaacccctctctcttgctgtacgtaacgtatgtgcacagtatgtcaccgacaaagacga   720
ttgcatgcgcatcgttttttgttgtgtttcaggcctcgctcgtgtctagggtataaacac   780
attgaagactacatatgcgcaagacgttgacattaacggggtcctgcagccgccgcaggt   840
gcatgtcgtgattaataccacgcgcctgcgtaaattagctagccgccgccctgtttcact   900
cggttagagacggacaggtgagacgggtctcggttaagcaagcaaattggaatgcaaggt   960
tgaaggtgtaatctgcatagcgtggaaatgagagggctctgtgggcagccaggaaggtga  1020
gacgaaatgaggaaagaggcaccagaagctgttgttctgaagtgcccgtggtcatagctc  1080
caggattaagtacggatgtcccatgccaagctgctggcttcgaaagcgagtacggagtag  1140
tgtccattgttcacgagggatccccaatgtgttagacatgcctgaatcaattttgtccta  1200
tttttggatttcaactgtttctctcgactgtgctcggtagcgactatgccgcaaggtaca  1260
ctacatgttgtacaataatcatacatcgaccttccgtaggagtgctgaaatacccgacct  1320
gctctctctagcaggtgcctaatggctttcgtgtaactcgatcgaaacggatcagcaagt  1380
ccatttgctgttggttgagatgtacgatttacaaacacgtggagaggtgagccacagcga  1440
taggcttctggaaggattctggcgtctcggaaagagggccactcgccccactaaccggcg  1500
ccgatcttgacatggggctcgcaggggggtttaagtgcacactacggagtacggattacac  1560
agtagtgtatgggtgggggcgagtttgggtggccttgtgtggggctcaccggctgcctgt  1620
tctcggggagtcttggcgggccgattggacccacctaaccacgggtagtcttggcccggc  1680
caactcacaccgccctcatgtttcggagccagtcagggaggcaggcactactcagtcagg  1740
tacacacgtcgggctcctcgatgctgggtgacatcgaggcgatactgcattccaactacg  1800
gttggcataggaggtatcctattctagagctgttctacgccggaacgtaacccgggataa  1860
cccgggatatcgcttccctgagcgagcgcgctgctgaggatcatacaacccaacaaccga  1920
cgacggtgcaagaaggttgggggaaggaagaaatcaaggaaaaaaaaataggggggggtgg  1980
ggaccaagagagaaagaaaggagaaaagggtgggggagggaagagaaaaaaaaacgga    2040
ggaatatggcgtcgctcttcgactggttccggaagggggcatctgggtacacatatgcac  2100
ctcttccgcacggcagggatataaaccgggagtgcagtcccaccgatcatgctgagtccg  2160
cccgtctccagacttcacggtcgcagaggactagacgcgcggtgaagatgactggcctcg  2220
                                                    M T G L   5
gagtgatggtggtgatggtcggcttcctggcgatcgcctctctgtaagcagcgattccag  2280
 V M V V M V G F L A I A S L                                   19
gggtccggtgtgcgttaaaagaaaaagctaacgccaccagacaatccgagtcccggccat  2340
                                           Q S E S R P C       26
gcgacaccccagacttgggcttccagtgtggtacggccatttcccacttctggggccagt  2400
 D T P D L G F Q C G T A I S H F W G Q Y                       46
actcgccctacttctccgtgccctcggagctggatgcttcgatccccgacgactgcgagg  2460
 S P Y F S V P S E L D A S I P D D C E V                       66
tgacgtttgcccaagtcctctcccgccacggcgcgagggcgccgacgctcaaacgggccg  2520
 T F A Q V L S R H G A R A P T L K R A A                       86
cgagctacgtcgatctcatcgacaggatccaccatggcgccatctcctacgggccgggct  2580
 S Y V D L I D R I H H G A I S Y G P G Y                      106
acgagttcctcaggacgtatgactacaccctgggcgccgacgagctcacccggacgggcc  2640
 E F L R T Y D Y T L G A D E L T R T G Q                      126
agcagcagatggtcaactcgggcatcaagttttaccgccgctaccgcgctctcgccccgca  2700
 Q Q M V N S G I K F Y R R Y R A L A R K                      146
```

FIG. 2-A

```
agtcgatcccettcgtccgcaccgccggccaggaccgcgtcgtccactcggccgagaact 2760
  S  I  P  F  V  R  T  A  G  Q  D  R  V  V  H  S  A  E  N  F   166
tcacccagggcttccactctgccctgctcgccgaccgcgggtccaccgtccggcccaccc 2820
  T  Q  G  F  H  S  A  L  L  A  D  R  G  S  T  V  R  P  T  L   186
tccctatgacatggtcgtcatcccggaaaccgccggcgccaacaacacgctccacaacg 2880
  P  Y  D  M  V  V  I  P  E  T  A  G  A  N  N  T  L  H  N  D   206
acctctgcaccgccttcgaggaaggcccgtactcgaccatcggcgacgacgcccaagaca 2940
  L  C  T  A  F  E  E  G  P  Y  S  T  I  G  D  D  A  Q  D  T   226
cctacctctccaccttcgccggacccatcaccgcccgggtcaacgccaacctgccgggcg 3000
  Y  L  S  T  F  A  G  P  I  T  A  R  V  N  A  N  L  P  G  A   246
ccaacctgaccgacgccgacacggtcgcgctgatggacctctgccccttcgagacggtcg 3060
  N  L  T  D  A  D  T  V  A  L  M  D  L  C  P  F  E  T  V  A   266
cctcctcctcctccgacccggcaacggcggacgcggggggcggcaacgggcggccgctgt 3120
  S  S  S  S  D  P  A  T  A  D  A  G  G  N  G  R  P  L  S     286
cgcccttctgccgcctgttcagcgagtccgagtggcgcgcgtacgactacctgcagtcgg 3180
  P  F  C  R  L  F  S  E  S  E  W  R  A  Y  D  Y  L  Q  S  V   306
tgggcaagtggtacgggtacgggccgggcaacccgctggggccgacgcaggggtcgggt  3240
  G  K  W  Y  G  Y  G  P  G  N  P  L  G  P  T  Q  G  V  G  F   326
tcgtcaacgagctgctggcgcggctggccggggtccccgtgcgcgacggcaccagcacca 3300
  V  N  E  L  L  A  R  L  A  G  V  P  V  R  D  G  T  S  T  N   346
accgcaccctcgacggcgacccgcgcaccttcccgctcggccggcccctctacgccgact 3360
  R  T  L  D  G  D  P  R  T  F  P  L  G  R  P  L  Y  A  D  F   366
tcagccacgacaacgacatgatgggcgtcctcggcgccctcggcgcctacgacggcgtcc 3420
  S  H  D  N  D  M  M  G  V  L  G  A  L  G  A  Y  D  G  V  P   386
cgcccctcgacaagaccgcccgccgcgacccggaagagctcggcgggtacgcggccagct 3480
  P  L  D  K  T  A  R  R  D  P  E  E  L  G  G  Y  A  A  S  W   406
gggccgtcccgttcgccgccaggatctacgtcgagaagatgcggtgcagcggcggcggcg 3540
  A  V  P  F  A  A  R  I  Y  V  E  K  M  R  C  S  G  G  G     426
gcggcggcggcggcgagggcggcaggagaaggatgaggagatggtcagggtgctgg     3600
  G  G  G  G  E  G  R  Q  E  K  D  E  E  M  V  R  V  L  V     446
tgaacgaccgggtgatgacgctgaaggggtgcggcgccgacgagagggggatgtgtacgc 3660
  N  D  R  V  M  T  L  K  G  C  G  A  D  E  R  G  M  C  T  L   466
tagaacggttcatcgaaagcatggcgtttgcgagggggaacggcaagtgggatctctgct 3720
  E  R  F  I  E  S  M  A  F  A  R  G  N  G  K  W  D  L  C  F   486
ttgcttgatatgcccacgcccgagattgaacagaacttgtgatgggggtagagtgtggta 3780
  A                                                           487 ttcgagatgatagttcacagtttcgggaatcaaaaatcggttagactggcgaaattcaa  3840
gtctggggcctgcggcgtctgcattctccgttccctgttgttaccttcttaatggttttt 3900
ttttatttttatttttcttaaattttcacacaaaccttttattgtcttttttttcttctt 3960
tttcttcttctgcacatcggatgggaattgtcgac                           3995
```

FIG. 2-B

```
   gaccttggctcgcaaccacacagacacgctgtctccgttctgcgctcttccacgcaaga
 1 ---------+---------+---------+---------+---------+---------+ 60
   ctggaaccgagcgttggtgtgtctgtgcgacagaggcaagacgcgagaaaggtgcgttct
    T  L  A  R  N  H  T  D  T  L  S  P  F  C  A  L  S  T  Q  E
   ggagtggcaagcatatgactactaccaaagtctggggaaatac
61 ---------+---------+---------+---------+--- 103
   cctcaccgttcgtatactgatgatggtttcagaccccttatg
    E  W  Q  A  Y  D  Y  Y  Q  S  L  G  K  Y
```

FIG. 4

```
   tacggtagcgcgcaccagcgacgcaagtcagctgtcaccgttctgtcaactcttcactca
 1 ---------+---------+---------+---------+---------+---------+ 60
   atgccatcgcgcgtggtcgctgcgttcagtcgacagtggcaagacagttgagaagtgagt
    T  V  A  R  T  S  D  A  S  Q  L  S  P  F  C  Q  L  F  T  H
   caatgagtggaagaagtacaactaccttcagtccttgggcaagtac
61 ---------+---------+---------+---------+------ 106
   gttactcaccttcttcatgttgatggaagtcaggaacccgttcatg
    N  E  W  K  K  Y  N  Y  L  Q  S  L  G  K  Y
```

FIG. 5

```
   caccatggcgcgcaccgccactcggaaccgtagtctgtctccattttgtgccatcttcac
 1 ---------+---------+---------+---------+---------+---------+ 60
   gtggtaccgcgcgtggcggtgagccttggcatcagacagaggtaaaacacggtagaagtg
    T  M  A  R  T  A  T  R  N  R  S  L  S  P  F  C  A  I  F  T
   tgaaaaggagtggctgcagtacgactaccttcaatctctatcaaagtac
61 ---------+---------+---------+---------+--------- 109
   actttcctcaccgacgtcatgctgatggaagttagagatagtttcatg
    E  K  E  W  L  Q  Y  D  Y  L  Q  S  L  S  K  Y
```

FIG. 6

```
    atgggcgtctctgctgttctacttcctttgtatctcctagctggagtcacctccggactg
  1 ---------+---------+---------+---------+---------+---------+ 60
    tacccgcagagacgacaagatgaaggaaacatagaggatcgacctcagtggaggcctgac
    M  G  V  S  A  V  L  L  P  L  Y  L  L  A  G  V  T  S  G  L gcagtccccgcctcgagaaatcaatccacttgcgatacggtcgatcaagggtatcaatgc
 61 ---------+---------+---------+---------+---------+---------+ 120
    cgtcaggggcggagctctttagttaggtgaacgctatgccagctagttcccatagttacg
    A  V  P  A  S  R  N  Q  S  T  C  D  T  V  D  Q  G  Y  Q  C ttctccgagacttcgcatctttggggtcaatacgcgccgttcttctctctggcaaacgaa
121 ---------+---------+---------+---------+---------+---------+ 180
    aagaggctctgaagcgtagaaaccccagttatgcgcggcaagaagagagaccgtttgctt
    F  S  E  T  S  H  L  W  G  Q  Y  A  P  F  F  S  L  A  N  E tcggtcatctcccctgatgtgcccgccggttgcagagtcactttcgctcaggtcctctcc
181 ---------+---------+---------+---------+---------+---------+ 240
    agccagtagaggggactacacgggcggccaacgtctcagtgaaagcgagtccaggagagg
    S  V  I  S  P  D  V  P  A  G  C  R  V  T  F  A  Q  V  L  S cgtcatggagcgcggtatccgaccgagtccaagggcaagaaatactccgctctcattgag
241 ---------+---------+---------+---------+---------+---------+ 300
    gcagtacctcgcgccataggctggctcaggttcccgttctttatgaggcgagagtaactc
    R  H  G  A  R  Y  P  T  E  S  K  G  K  K  Y  S  A  L  I  E gagatccagcagaacgtgaccacctttgatggaaaatatgccttcctgaagacatacaac
301 ---------+---------+---------+---------+---------+---------+ 360
    ctctaggtcgtcttgcactggtggaaactaccttttatacggaaggacttctgtatgttg
    E  I  Q  Q  N  V  T  T  F  D  G  K  Y  A  F  L  K  T  Y  N tacagcttgggtgcagatgacctgactcccttcggagagcaggagctagtcaactccggc
361 ---------+---------+---------+---------+---------+---------+ 420
    atgtcgaacccacgtctactggactgagggaagcctctcgtcctcgatcagttgaggccg
    Y  S  L  G  A  D  D  L  T  P  F  G  E  Q  E  L  V  N  S  G atcaagttctaccagcgctacaacgccctcaccccgacacatcaacccctttcgtccgcgcc
421 ---------+---------+---------+---------+---------+---------+ 480
    tagttcaagatggtcgcgatgttgcgggagtgggctgtgtagttggggaagcaggcgcgg
    I  K  F  Y  Q  R  Y  N  A  L  T  R  H  I  N  P  F  V  R  A accgatgcatcccgcgtccacgaatccgccgagaagttcgtcgagggcttccaaaccgct
481 ---------+---------+---------+---------+---------+---------+ 540
    tggctacgtagggcgcaggtgcttaggcggctcttcaagcagctcccgaaggtttggcga
    T  D  A  S  R  V  H  E  S  A  E  K  F  V  E  G  F  Q  T  A cgacaggacgatcatcacgccaatccccaccagccttcgcctcgcgtggacgtggccatc
541 ---------+---------+---------+---------+---------+---------+ 600
    gctgtcctgctagtagtgcggttaggggtggtcggaagcggagcgcacctgcaccggtag
    R  Q  D  D  H  H  A  N  P  H  Q  P  S  P  R  V  D  V  A  I
```

FIG. 7-A

```
       cccgaaggcagcgcctacaacaacacgctggagcacagcctctgcaccgccttcgaatcc
601    ----------+---------+---------+---------+---------+---------+  660
       gggcttccgtcgcggatgttgttgtgcgacctcgtgtcggagacgtggcggaagcttagg
        P  E  G  S  A  Y  N  N  T  L  E  H  S  L  C  T  A  F  E  S agcaccgtcggcgacgacgcggtcgccaacttcaccgccgtgttcgcgccggcgatcgcc
661    ----------+---------+---------+---------+---------+---------+  720
       tcgtggcagccgctgctgcgccagcggttgaagtggcggcacaagcgcggccgctagcgg
        S  T  V  G  D  D  A  V  A  N  F  T  A  V  F  A  P  A  I  A cagcgcctggaggccgatcttcccggcgtgcagctgtccaccgacgacgtggtcaacctg
721    ----------+---------+---------+---------+---------+---------+  780
       gtcgcggacctccggctagaagggccgcacgtcgacaggtggctgctgcaccagttggac
        Q  R  L  E  A  D  L  P  G  V  Q  L  S  T  D  D  V  V  N  L atggccatgtgtccgttcgagacggtcagcctgaccgacgacgcgcacacgctgtcgccg
781    ----------+---------+---------+---------+---------+---------+  840
       taccggtacacaggcaagctctgccagtcggactggctgctgcgcgtgtgcgacagcggc
        M  A  M  C  P  F  E  T  V  S  L  T  D  D  A  H  T  L  S  P ttctgcgacctcttcacggccactgagtggacgcagtacaactacctgctctcgctggac
841    ----------+---------+---------+---------+---------+---------+  900
       aagacgctggagaagtgccggtgactcacctgcgtcatgttgatggacgagagcgacctg
        F  C  D  L  F  T  A  T  E  W  T  Q  Y  N  Y  L  L  S  L  D aagtactacggctacggcggggggcaatccgctgggtccggtgcaggggggtcggctgggcg
901    ----------+---------+---------+---------+---------+---------+  960
       ttcatgatgccgatgccgccccgttaggcgacccaggccacgtccccagccgacccgc
        K  Y  Y  G  Y  G  G  G  N  P  L  G  P  V  Q  G  V  G  W  A aacgagctgatggcgcggctaacgcgcgccccgtgcacgaccacacctgcgtcaacaac
961    ----------+---------+---------+---------+---------+---------+  1020
       ttgctcgactaccgcgccgattgcgcgcggggggcacgtgctggtgtggacgcagttgttg
        N  E  L  M  A  R  L  T  R  A  P  V  H  D  H  T  C  V  N  N accctcgacgcgagtccggccaccttcccgctgaacgccaccctctacgccgacttctcc
1021   ----------+---------+---------+---------+---------+---------+  1080
       tgggagctgcgctcaggccggtggaagggcgacttgcggtgggagatgcggctgaagagg
        T  L  D  A  S  P  A  T  F  P  L  N  A  T  L  Y  A  D  F  S cacgacagcaacctggtgtcgatcttctgggcgctgggcctgtacaacggcaccgcgccg
1081   ----------+---------+---------+---------+---------+---------+  1140
       gtgctgtcgttggaccacagctagaagacccgcgacccggacatgttgccgtggcgcggc
        H  D  S  N  L  V  S  I  F  W  A  L  G  L  Y  N  G  T  A  P ctgtcgcagacctccgtcgagagcgtctcccagacggacgggtacgccgccgcctggacg
1141   ----------+---------+---------+---------+---------+---------+  1200
       gacagcgtctggaggcagctctcgcagagggtctgcctgcccatgcggcggcggacctgc
        L  S  Q  T  S  V  E  S  V  S  Q  T  D  G  Y  A  A  A  W  T
```

FIG. 7-B

```
      gtgccgttcgccgctcgcgcgtacgtcgagatgatgcagtgtcgcgccgagaaggagccg
1201  ------------+---------+---------+---------+---------+---------+  1260
      cacggcaagcggcgagcgcgcatgcagctctactacgtcacagcgcggctcttcctcggc
      V  P  F  A  A  R  A  Y  V  E  M  M  Q  C  R  A  E  K  E  P ctggtgcgcgtgctggtcaacgaccgggtcatgccgctgcatggctgccctacggacaag
1261  ------------+---------+---------+---------+---------+---------+  1320
      gaccacgcgcacgaccagttgctggcccagtacggcgacgtaccgacgggatgcctgttc
      L  V  R  V  L  V  N  D  R  V  M  P  L  H  G  C  P  T  D  K ctggggcggtgcaagcgggacgctttcgtcgcggggctgagctttgcgcaggcgggcggg
1321  ------------+---------+---------+---------+---------+---------+  1380
      gaccccgccacgttcgccctgcgaaagcagcgccccgactcgaaacgcgtccgcccgccc
      L  G  R  C  K  R  D  A  F  V  A  G  L  S  F  A  Q  A  G  G aactgggcggattgtttctgatgttgagaagaaaggtagatagataggtagtacatatgg
1381  ------------+---------+---------+---------+---------+---------+  1440
      ttgacccgcctaacaaagactacaactcttctttccatctatctatccatcatgtatacc
      N  W  A  D  C  F attgctcggctctgggtcgttgcccacaatgcatattacgcccgtcaactgccttgcgcc
1441  ------------+---------+---------+---------+---------+---------+  1500
      taacgagccgagacccagcaacgggtgttacgtataatgcgggcagttgacggaacgcgg atccacctctcaccctggacgcaaccgagcggtctaccctgcacacggcttccaccgcga
1501  ------------+---------+---------+---------+---------+---------+  1560
      taggtggagagtgggacctgcgttggctcgccagatgggacgtgtgccgaaggtggcgct cgcgcacggataaggcgcttttgttacggggttggggctgggggcagccggagccggaga
1561  ------------+---------+---------+---------+---------+---------+  1620
      gcgcgtgcctattccgcgaaaacaatgccccaaccccgaccccgtcggcctcggcctct gagagaccagcgtgaaaaacgacagaacatagatatcaattcgacgccaattcatgcaga
1621  ------------+---------+---------+---------+---------+---------+  1680
      ctctctggtcgcacttttgctgtcttgtatctatagttaagctgcggttaagtacgtct gtagtatacagacgaactgaaacaaacacatcacttccctcgctcctctcctgtagaaga
1681  ------------+---------+---------+---------+---------+---------+  1740
      catcatatgtctgcttgactttgtttgtgtagtgaagggagcgaggagaggacatcttct cgctcccaccagccgcttctggcccttattcccgtacgctaggtagaccagtcagccaga
1741  ------------+---------+---------+---------+---------+---------+  1800
      gcgagggtggtcggcgaagaccgggaataagggcatgcgatccatctggtcagtcggtct cgcatgcctcacaagaacggggggcgggggacacactccgctcgtacagcacccacgacgt
1801  ------------+---------+---------+---------+---------+---------+  1860
      gcgtacggagtgttcttgccccccgccccctgtgtgaggcgagcatgtcgtgggtgctgca gtacaggaaaaccggcagcgccacaatcgtcgagagccatctgcaggaattc
1861  ------------+---------+---------+---------+---------+---   1912
      catgtccttttggccgtcgcggtgttagcagctctcggtagacgtccttaag
```

FIG. 7-C

```
9a1      1222 gacggtcagcctgaccgacgacgcgcacacgctgtcgccgttctgcgacc 1271
              ||||||||||||||||||||||||||||||||||||||||||||||||||
aterr21     1 gacggtcagcctgaccgacgacgcgcacacgctgtcgccgttctgcgacc   50

9a1      1272 tcttcacggccactgagtggacgcagtacaactacctgctctcgctggac 1321
              ||||||| ||| | ||||||||||||||||||||||||||||||||||||
aterr21    51 tcttcaccgccgccgagtggacgcagtacaactacctgctctcgctggac  100

9a1      1322 aagtactacggc 1333
              |||||||||| |
aterr21   101 aagtactacgtc  112
```

FIG. 10A

```
9a1      1507 cagcaacctggtgtcgatcttctgggcgctgggcctgtacaacggcaccg 1556
              ||| ||||||||||||||||||||||:||||||| |||||||||||||||
aterr58     1 cagtaacctggtgtcgatcttctggncgctgggtctgtacaacggcacca   50

9a1      1557 cgccgctgtcgcagacctccgtcgagagcgtctcccagacg 1597
              ||| |||||||||||||| |||  ||   || ||| ||||
atter58    51 agcccctgtcgcagaccaccgtggaggatatcacccggacg   91
```

FIG. 10B

```
gaccttggctcgcaaccacacagacacgctgtctccgttctgcgctcttttccacgcaaga    60
 T  L  A  R  N  H  T  D  T  L  S  P  F  C  A  L  S  T  Q  E    20 ggagtggcaagcatatgactactaccaaagtctggggaaatac                     103
 E  W  Q  A  Y  D  Y  Y  Q  S  L  G  K  Y                       34
```

FIG. 11A

```
tacggtagcgcgcaccagcgacgcaagtcagctgtcaccgttctgtcaactcttcactca    60
 T  V  A  R  T  S  D  A  S  Q  L  S  P  F  C  Q  L  F  T  H    20 caatgagtggaagaagtacaactaccttcagtccttgggcaagtac                  106
 N  E  W  K  K  Y  N  Y  L  Q  S  L  G  K  Y                    35
```

FIG. 11B

```
caccatggcgcgcaccgccactcggaaccgtagtctgtctccatttttgtgccatcttcac   60
 T  M  A  R  T  A  T  R  N  R  S  L  S  P  F  C  A  I  F  T    20 tgaaaaggagtggctgcagtacgactaccttcaatctctatcaaagtac               109
 E  K  E  W  L  Q  Y  D  Y  L  Q  S  L  S  K  Y                 36
```

FIG. 11C

```
gacggtcagcctgaccgacgacgcgcacacgctgtcgccgttctgcgacctcttcaccgc    60
 T  V  S  L  T  D  D  A  H  T  L  S  P  F  C  D  L  F  T  A    20 cgccgagtggacgcagtacaactacctgctctcgctggacaagtac                  106
 A  E  W  T  Q  Y  N  Y  L  L  S  L  D  K  Y                    15
```

FIG. 11D

```
cagtaacctggtgtcgatcttctgggcgctgggtctgtacaacggcaccaagcccctgtc   60
 S  N  L  V  S  I  F  W  A  L  G  L  Y  N  G  T  K  P  L  S    20 gcagaccaccgtggaggatatcacccggacggacgggtacgcggccgcctggacggtgcc   120
 Q  T  T  V  E  D  I  T  R  T  D  G  Y  A  A  A  W  T  V  P    40 gtttgccgcccgcgcctacatcgagatgatgcagtgtcgcgcggagaagcagccgctggta  181
 F  A  A  R  A  Y  I  E  M  M  Q  C  R  A  E  K  Q  P  L  V    60
```

FIG. 11E

```
  1 TCTGTAACCGATAGCGGACCGACTAGGCATCGTTGATCCACAATATCTCA    50
 51 GACAATGCAACTCAGTCGAATATGAAGGGCTACAGCCAGCATTTAAATAC   100
101 GGCCGTCTAGGTCGGGCTCCGGGGATGAGGAGGAGCAGGCTCGTGTTCAT   150
151 TTCGGTCATGGCTTTTTTCACGGTCGCTCTTTCGCTTTATTACTTGCTAT   200
            M  A  F  F  T  V  A  L  S  L  Y  Y  L  L  S    15
201 CGAGgtgagatctctacaatatctgtctgcttagttgaattggtacttat   250
     R                                                   16

251 ctgtacagAGTCTCTGCTCAGGCCCCAGTGGTCCAGAATCATTCATGCAA   300
             V  S  A  Q  A  P  V  V  Q  N  H  S  C  N     30
                                                +
301 TACGGCGGACGGTGGATATCAATGCTTCCCCAATGTCTCTCATGTTTGGG   350
     T  A  D  G  G  Y  Q  C  F  P  N  V  S  H  V  W  G    47
                                 +
351 GTCAGTACTCGCCGTACTTCTCCATCGAGCAGGAGTCAGCTATCTCTGAG   400
     Q  Y  S  P  Y  F  S  I  E  Q  E  S  A  I  S  E       63

401 GACGTGCCTCATGGCTGTGAGGTTACCTTTGTGCAGGTGCTCTCGCGGCA   450
     D  V  P  H  G  C  E  V  T  F  V  Q  V  L  S  R  H    80

451 TGGGGCTAGGTATCCGACAGAGTCGAAGAGTAAGGCGTACTCGGGGTTGA   500
     G  A  R  Y  P  T  E  S  K  S  K  A  Y  S  G  L  I    97

501 TTGAAGCAATCCAGAAGAATGCTACCTCTTTTTGGGGACAGTATGCTTTT   550
     E  A  I  Q  K  N  A  T  S  F  W  G  Q  Y  A  F      113
                   +
551 CTGGAGAGTTATAACTATACCCTCGGCGCGGATGACTTGACTATCTTCGG   600
     L  E  S  Y  N  Y  T  L  G  A  D  D  L  T  I  F  G   130
              +.
601 CGAGAACCAGATGGTTGATTCGGGTGCCAAGTTCTACCGACGGTATAAGA   650
     E  N  Q  M  V  D  S  G  A  K  F  Y  R  R  Y  K  N   147

651 ATCTCGCCAGGAAAAATACTCCTTTTATCCGTGCATCAGGGTCTGACCGT   700
     L  A  R  K  N  T  P  F  I  R  A  S  G  S  D  R     163
```

FIG. 13-A

```
 701  GTCGTTGCGTCTGCGGAGAAGTTCATTAATGGATTTCGCAAGGCTCAGCT   750
       V  V  A  S  A  E  K  F  I  N  G  F  R  K  A  Q  L    180

751  CCACGACCATGGCTCCAAACGTGCTACGCCAGTTGTCAATGTGATTATCC   800
       H  D  H  G  S  K  R  A  T  P  V  V  N  V  I  I  P    197

801  CTGAAATCGATGGGTTTAACAACACCCTGGACCATAGCACGTGCGTATCT   850
       E  I  D  G  F  N  N  T  L  D  H  S  T  C  V  S       213
                          +

851  TTTGAGAATGATGAGCGGGCGGATGAAATTGAAGCCAATTTCACGGCAAT   900
       F  E  N  D  E  R  A  D  E  I  E  A  N  F  T  A  I    230
                                                 +

901  TATGGGACCTCCGATCCGCAAACGTCTGGAAAATGACCTCCCTGGCATCA   950
       M  G  P  P  I  R  K  R  L  E  N  D  L  P  G  I  K    247

951  AACTTACAAACGAGAATGTAATATATTTGATGGATATGTGCTCTTTCGAC  1000
       L  T  N  E  N  V  I  Y  L  M  D  M  C  S  F  D       263

1001  ACCATGGCGCGCACCGCCCACGGAACCGAGCTGTCTCCATTTTGTGCCAT  1050
       T  M  A  R  T  A  H  G  T  E  L  S  P  F  C  A  I    280

1051  CTTCACTGAAAAGGAGTGGCTGCAGTACGACTACCTTCAATCTCTATCAA  1100
       F  T  E  K  E  W  L  Q  Y  D  Y  L  Q  S  L  S  K    297

1101  AGTACTACGGCTACGGTGCCGGAAGCCCCCTTGGCCCAGCTCAGGGAATT  1150
       Y  Y  G  Y  G  A  G  S  P  L  G  P  A  Q  G  I       313

1151  GGCTTCACCAACGAGCTGATTGCCCGACTAACGCAATCGCCCGTCCAGGA  1200
       G  F  T  N  E  L  I  A  R  L  T  Q  S  P  V  Q  D    330

1201  CAACACAAGCACCAACCACACTCTAGACTCGAACCCAGCCACATTTCCGC  1250
       N  T  S  T  N  H  T  L  D  S  N  P  A  T  F  P  L    347
       +        +

1251  TCGACAGGAAGCTCTACGCCGACTTCTCCCACGACAATAGCATGATATCG  1300
       D  R  K  L  Y  A  D  F  S  H  D  N  S  M  I  S       363

1301  ATATTCTTCGCCATGGGTCTGTACAACGGCACCCAGCCGCTGTCAATGGA  1350
       I  F  F  A  M  G  L  Y  N  G  T  Q  P  L  S  M  D    380
                                                 +
```

FIG. 13-B

```
1351  TTCCGTGGAGTCGATCCAGGAGATGGACGGTTACGCGGCGTCTTGGACTG  1400
        S  V  E  S  I  Q  E  M  D  G  Y  A  A  S  W  T  V   397

1401  TTCCGTTTGGTGCGAGGGCTTACTTTGAGCTCATGCAGTGCGAGAAGAAG  1450
        P  F  G  A  R  A  Y  F  E  L  M  Q  C  E  K  K    413

1451  GAGCCGCTTGTGCGGGTATTAGTGAATGATCGCGTTGTTCCTCTTCATGG  1500
        E  P  L  V  R  V  L  V  N  D  R  V  V  P  L  H  G   430

1501  CTGCGCAGTTGACAAGTTTGGACGGTGCACTTTGGACGATTGGGTAGAGG  1550
        C  A  V  D  K  F  G  R  C  T  L  D  D  W  V  E  G   447

1551  GCTTGAATTTTGCAAGGAGCGGCGGGAACTGGAAGACTTGTTTTACCCTA  1600
        L  N  F  A  R  S  G  G  N  W  K  T  C  F  T  L     463

1601  TAAAGGGCGTTTGCTCATTCATAAGTGTTGTGCAGGTATAGGAAGGTTAG  1650
        *

1651  GGAATTAGCTGTTTGGCTTTACTCTTATTAGACCAAGAATGATTTGTTTG  1700
1701  TTCTCAAGGCCTTCTAGCATATCGTCAAGTGGGATAAATCACCTATCCTC  1750
1751  CATGTGTAGGTGAACCCGCTCTTGCATCAACCTCTTGTGTTTCAGAGTAG  1800
1801  TTTCACCAAACATATCCTCGTGTCCTCTCTTCTGCTCTTCGGTCTCATAT  1850
1851  TACACTGTTCTCTATCTATATCGTCAACAAAACTACCACCCAAACACCAA  1900
1901  ATGTCACACTTTCCAGCACGAAATTTCTTCG  1931
```

FIG. 13-C

```
  1  TTCCACGCTGAAAGCCTGACTGCGATTTCCAAGCTGCATGCAGGCTGCTC   50
 51  AACTGCCTGCTTATCTTCATCAGACGCAGATACACAACCTGGTCTGTAGA  100
101  TGCACCCATGACGGACGAACGCACCGCTCTCTTGGCCTCCAGGGACCCGG  150
151  AGGTCGAGGGCGATGAGGTCGCGCCCTCGACGGCCTCCCAGTCCCTGTTG  200
201  CAGTTGAGATCTCGCTGCGAACGTCGACCGCAGATATGGTTGTCTTCGAC  250
251  GTTTTCTCGCCTTCGAGGAAGAATTGCTGCTGTGACGATGAGTCTGTTGT  300
                                         M  S  L  L    5

301  TGCTGGTGCTGTCCGGCGGGTTGGTCGCGTTATAgtatgctccttctctc  350
      L  V  L  S  G  G  L  V  A  L  Y                   16

351  tggtcatattgttttctgctaacgttctcataattgaagTGTCTCAAGAA  400
                                            V  S  R  N  20

401  ATCCGCATGTTGATAGCCACTCTTGCAATACAGTGGAAGGAGGGTATCAG  450
      P  H  V  D  S  H  S  C  N  T  V  E  G  G  Y  Q   36

451  TGTCGTCCAGAAATCTCCCACTCCTGGGGCCAGTATTCTCCATTCTTCTC  500
      C  R  P  E  I  S  H  S  W  G  Q  Y  S  P  F  F  S  53

501  CCTGGCAGACCAGTCGGAGATCTCGCCAGATGTCCCACAGAACTGCAAGA  550
      L  A  D  Q  S  E  I  S  P  D  V  P  Q  N  C  K  I  70

551  TTACGTTTGTCCAGCTGCTTTCTCGTCACGGCGCTAGATACCCTACGTCT  600
      T  F  V  Q  L  L  S  R  H  G  A  R  Y  P  T  S    86

601  TCCAAGACGGAGCTGTATTCGCAGCTGATCAGTCGGATTCAGAAGACGGC  650
      S  K  T  E  L  Y  S  Q  L  I  S  R  I  Q  K  T  A  103

651  GACTGCGTACAAAGGCTACTATGCCTTCTTGAAAGACTACAGATACCAGC  700
      T  A  Y  K  G  Y  Y  A  F  L  K  D  Y  R  Y  Q  L  120

701  TGGGAGCGAACGACCTGACGCCCTTTGGGGAAAACCAGATGATCCAGTTG  750
      G  A  N  D  L  T  P  F  G  E  N  Q  M  I  Q  L   136
```

FIG. 17-A

```
 751  GGCATCAAGTTTTATAACCATTACAAGAGTCTCGCCAGGAATGCCGTCCC   800
       G  I  K  F  Y  N  H  Y  K  S  L  A  R  N  A  V  P    153

801  ATTCGTTCGTTGCTCCGGCTCTGATCGGGTCATTGCCTCGGGGAGACTTT   850
       F  V  R  C  S  G  S  D  R  V  I  A  S  G  R  L  F    170

851  TCATCGAAGGTTTCCAGAGCGCCAAAGTGCTGGATCCTCATTCAGACAAG   900
        I  E  G  F  Q  S  A  K  V  L  D  P  H  S  D  K      186

901  CATGACGCTCCTCCCACGATCAACGTGATCATCGAGGAGGGTCCGTCCTA   950
       H  D  A  P  P  T  I  N  V  I  I  E  E  G  P  S  Y    203

951  CAATAACACGCTCGACACCGGCAGCTGTCCAGTCTTTGAGGACAGCAGCG  1000
       N  N  T  L  D  T  G  S  C  P  V  F  E  D  S  S  G    220
       +

1001  GGGGACATGACGCACAGGAAAAGTTCGCAAAGCAATTCGCACCAGCTATC  1050
       G  H  D  A  Q  E  K  F  A  K  Q  F  A  P  A  I       236

1051  CTGGAAAAGATCAAGGACCATCTTCCCGGCGTGGACCTGGCCGTGTCGGA  1100
       L  E  K  I  K  D  H  L  P  G  V  D  L  A  V  S  D    253

1101  TGTACCGTACTTGATGGACTTGTGTCCGTTTGAGACCTTGGCTCGCAACC  1150
       V  P  Y  L  M  D  L  C  P  F  E  T  L  A  R  N  H    270
                                                      +

1151  ACACAGACACGCTGTCTCCGTTCTGCGCTCTTTCCACGCAAGAGGAGTGG  1200
       T  D  T  L  S  P  F  C  A  L  S  T  Q  E  E  W       286

1201  CAAGCATATGACTACTACCAAAGTCTGGGGAAATACTATGGCAATGGCGG  1250
       Q  A  Y  D  Y  Y  Q  S  L  G  K  Y  Y  G  N  G  G    303

1251  GGGTAACCCGTTGGGGCCAGCCCAAGGCGTGGGGTTTGTCAACGAGTTGA  1300
       G  N  P  L  G  P  A  Q  G  V  G  F  V  N  E  L  I    320

1301  TTGCTCGCATGACCCATAGCCCTGTCCAGGACTACACCACGGTCAACCAC  1350
       A  R  M  T  H  S  P  V  Q  D  Y  T  T  V  N  H       336
                                                      +

1351  ACTCTTGACTCGAATCCGGCGACATTCCCTTTGAACGCGACGCTGTACGC  1400
       T  L  D  S  N  P  A  T  F  P  L  N  A  T  L  Y  A    353
                                 +
```

FIG. 17-B

```
1401  AGATTTCAGCCACGACAACACAATGACGTCAATTTTCGCGGCCTTGGGCC  1450
       D   F   S   H   D   N   T   M   T   S   I   F   A   A   L   G   L    370

1451  TGTACAACGGGACCGCGAAGCTGTCCACGACCGAGATCAAGTCCATTGAA  1500
       Y   N   G   T   A   K   L   S   T   T   E   I   K   S   I   E        386
       +

1501  GAGACGGACGGCTACTCGGCGGCGTGGACCGTTCCGTTCGGGGGGCGAGC  1550
       E   T   D   G   Y   S   A   A   W   T   V   P   F   G   G   R   A    403

1551  CTATATCGAGATGATGCAGTGTGATGATTCGGATGAGCCAGTCGTTCGGG  1600
       Y   I   E   M   M   Q   C   D   D   S   D   E   P   V   V   R   V    420

1601  TGCTGGTCAACGACCGGGTGGTGCCACTGCATGGCTGCGAGGTGGACTCC  1650
       L   V   N   D   R   V   V   P   L   H   G   C   E   V   D   S        436

1651  CTGGGGCGATGCAAACGAGACGACTTTGTCAGGGACTGAGTTTTGCGCG   1700
       L   G   R   C   K   R   D   D   F   V   R   G   L   S   F   A   R    453

1701  ACAGGGTGGGAACTGGGAGGGGTGTTACGCTGCTTCTGAGTAGGTTTATT  1750
       Q   G   G   N   W   E   G   C   Y   A   A   S   E   *                466

1751  CAGCGAGTTTCGACCTTTCTATCCTTCAAACACTGCACAAAGACACACTG  1800
1801  CATGAAATGGTAACAGGCCTGGAGCGTTTTAGAAGGAAAAAAGTT       1845
```

FIG. 17-C

```
  1 AGATTCAACGACGGAGGAATCGCAACCCTAATTGTCGGTATCATGGTGAC   50
                                                  M V T    3

51 TCTGACTTTCCTGCTTTCGGCGGCGTATCTGCTTTCTGGgtgagtggctt  100
     L  T  F  L  L  S  A  A  Y  L  L  S  G              16

101 ggatctattgctcggatagggctgtggtgctgattctgaaacggagTAGA  150
                                                   R   17

151 GTGTCTGCGGCACCTAGTTCTGCTGGCTCCAAGTCCTGCGATACGGTAGA  200
     V  S  A  A  P  S  S  A  G  S  K  S  C  D  T  V  D  34

201 CCTCGGGTACCAGTGCTCCCCTGCGACTTCTCATCTATGGGGCCAGTACT  250
     L  G  Y  Q  C  S  P  A  T  S  H  L  W  G  Q  Y  S  51

251 CGCCATTCTTTTCGCTCGAGGACGAGCTGTCCGTGTCGAGTAAGCTTCCC  300
     P  F  F  S  L  E  D  E  L  S  V  S  S  K  L  P     67

301 AAGGATTGCCGGATCACCTTGGTACAGGTGCTATCGCGCCATGGAGCGCG  350
     K  D  C  R  I  T  L  V  Q  V  L  S  R  H  G  A  R  84

351 GTACCCAACCAGCTCCAAGAGCAAAAAGTATAAGAAGCTTGTGACGGCGA  400
     Y  P  T  S  S  K  S  K  K  Y  K  K  L  V  T  A  I 101

401 TCCAGGCCAATGCCACCGACTTCAAGGGCAAGTTTGCCTTTTTGAAGACG  450
     Q  A  N  A  T  D  F  K  G  K  F  A  F  L  K  T    117
        +

451 TACAACTATACTCTGGGTGCGGATGACCTCACTCCCTTTGGGGAGCAGCA  500
     Y  N  Y  T  L  G  A  D  D  L  T  P  F  G  E  Q  Q 134
     +

501 GCTGGTGAACTCGGGCATCAAGTTCTACCAGAGGTACAAGGCTCTGGCGC  550
     L  V  N  S  G  I  K  F  Y  Q  R  Y  K  A  L  A  R 151

551 GCAGTGTGGTGCCGTTTATTCGCGCCTCAGGCTCGGACCGGGTTATTGCT  600
     S  V  V  P  F  I  R  A  S  G  S  D  R  V  I  A    167
```

FIG. 19-A

```
601  TCGGGAGAGAAGTTCATCGAGGGGTTCCAGCAGGCGAAGCTGGCTGATCC  650
      S  G  E  K  F  I  E  G  F  Q  Q  A  K  L  A  D  P   184

651  TGGCGCGACGAACCGCGCCGCTCCGGCGATTAGTGTGATTATTCCGGAGA  700
       G  A  T  N  R  A  A  P  A  I  S  V  I  I  P  E  S  201

701  GCGAGACGTTCAACAATACGCTGGACCACGGTGTGTGCACGAAGTTTGAG  750
        E  T  F  N  N  T  L  D  H  G  V  C  T  K  F  E    217
              +

751  GCGAGTCAGCTGGGAGATGAGGTTGCGGCCAATTTCACTGCGCTCTTTGC  800
      A  S  Q  L  G  D  E  V  A  A  N  F  T  A  L  F  A   234
                                  +

801  ACCCGACATCCGAGCTCGCGCCGAGAAGCATCTTCCTGGCGTGACGCTGA  850
       P  D  I  R  A  R  A  E  K  H  L  P  G  V  T  L  T  251

851  CAGACGAGGACGTTGTCAGTCTAATGGACATGTGTTCGTTTGATACGGTA  900
       D  E  D  V  V  S  L  M  D  M  C  S  F  D  T  V    267

901  GCGCGCACCAGCGACGCAAGTCAGCTGTCACCGTTCTGTCAACTCTTCAC  950
      A  R  T  S  D  A  S  Q  L  S  P  F  C  Q  L  F  T   284

951  TCACAATGAGTGGAAGAAGTACAACTACCTTCAGTCCTTGGGCAAGTACT  1000
      H  N  E  W  K  K  Y  N  Y  L  Q  S  L  G  K  Y  Y   301

1001 ACGGCTACGGCGCAGGCAACCCTCTGGGACCGGCTCAGGGGATAGGGTTC  1050
       G  Y  G  A  G  N  P  L  G  P  A  Q  G  I  G  F    317

1051 ACCAACGAGCTGATTGCCCGGTTGACTCGTTCGCCAGTGCAGGACCACAC  1100
       T  N  E  L  I  A  R  L  T  R  S  P  V  Q  D  H  T  334

1101 CAGCACTAACTCGACTCTAGTCTCCAACCCGGCCACCTTCCCGTTGAACG  1150
       S  T  N  S  T  L  V  S  N  P  A  T  F  P  L  N  A  351
              +                                   +

1151 CTACCATGTACGTCGACTTTTCACACGACAACAGCATGGTTTCCATCTTC  1200
       T  M  Y  V  D  F  S  H  D  N  S  M  V  S  I  F    367

1201 TTTGCATTGGGCCTGTACAACGGCACTGAACCCTTGTCCCGGACCTCGGT  1250
      F  A  L  G  L  Y  N  G  T  E  P  L  S  R  T  S  V   384
                       +
```

FIG. 19-B

```
1251  GGAAAGCGCCAAGGAATTGGATGGGTATTCTGCATCCTGGGTGGTGCCTT  1300
       E  S  A  K  E  L  D  G  Y  S  A  S  W  V  V  P  F   401

1301  TCGGCGCGCGAGCCTACTTCGAGACGATGCAATGCAAGTCGGAAAAGGAG  1350
       G  A  R  A  Y  F  E  T  M  Q  C  K  S  E  K  E    417

1351  CCTCTTGTTCGCGCTTTGATTAATGACCGGGTTGTGCCACTGCATGGCTG  1400
       P  L  V  R  A  L  I  N  D  R  V  V  P  L  H  G  C  434

1401  CGATGTGGACAAGCTGGGGCGATGCAAGCTGAATGACTTTGTCAAGGGAT  1450
       D  V  D  K  L  G  R  C  K  L  N  D  F  V  K  G  L  451

1451  TGAGTTGGGCCAGATCTGGGGGCAACTGGGGAGAGTGCTTTAGTTGAGAT  1500
       S  W  A  R  S  G  G  N  W  G  E  C  F  S  *        465

1501  GTCATTGTTATGCTATACTCCAATAGACCGTTGCTTAGCCATTCACTTCA  1550
1551  CTTTGCTCGAACCGCCTGCCG                               1571
```

FIG. 19-C

```
  1 ACGTCCCAGGTCGGGGACTACATCCGCTATGTGGTCCTCTACTTCGTCGG  50
 51 AAGAATATACTGTCTCTTGTGGCTACCATGGGGGTTTTCGTCGTTCTATT 100
                                    M  G  V  F  V  V  L  L    8

101 ATCTATCGCGACTCTGTTCGGCAGgtatgtgcaccgctctaggttcaact 150
     S  I  A  T  L  F  G  S                              16

151 cgcctggtaactgacaaacagcacagCACATCGGGCACTGCGCTGGGCCC 200
                              T  S  G  T  A  L  G  P      24

201 CCGTGGAAATCACAGCGACTGCACCTCAGTCGACCGGGGGTATCAATGCT 250
     R  G  N  H  S  D  C  T  S  V  D  R  G  Y  Q  C  F   41
        +

251 TCCCTGAGCTCTCCCATAAATGGGGTCTCTACGCGCCCTATTTCTCCCTC 300
     P  E  L  S  H  K  W  G  L  Y  A  P  Y  F  S  L     57

301 CAGGATGAATCTCCGTTTCCTCTGGACGTCCCGGATGACTGCCACATCAC 350
     Q  D  E  S  P  F  P  L  D  V  P  D  D  C  H  I  T   74

351 CTTTGTGCAGGTGCTGGCCCGACATGGAGCGCGGTCTCCAACCGATAGCA 400
     F  V  Q  V  L  A  R  H  G  A  R  S  P  T  D  S  K   91

401 AGACAAAGGCGTATGCCGCGACTATTGCAGCCATCCAGAAGAATGCCACC 450
     T  K  A  Y  A  A  T  I  A  A  I  Q  K  N  A  T    107
                                            +

451 GCGTTGCCGGGCAAATACGCCTTCCTGAAGTCGTACAATTACTCCATGGG 500
     A  L  P  G  K  Y  A  F  L  K  S  Y  N  Y  S  M  G  124
                                        +

501 CTCCGAGAACCTGAACCCCTTCGGGCGGAACCAACTGCAAGATCTGGGCG 550
     S  E  N  L  N  P  F  G  R  N  Q  L  Q  D  L  G  A  141

551 CCCAGTTCTACCGTCGCTACGACACCCTCACCCGGCACATCAACCCTTTC 600
     Q  F  Y  R  R  Y  D  T  L  T  R  H  I  N  P  F    157

601 GTCCGGGCCGCGGATTCCTCCCGCGTCCACGAATCAGCCGAGAAGTTCGT 650
     V  R  A  A  D  S  S  R  V  H  E  S  A  E  K  F  V  174
```

FIG. 21-A

```
651  CGAGGGCTTCCAAAACGCCCGCCAAGGCGATCCTCACGCCAACCCTCACC  700
      E  G  F  Q  N  A  R  Q  G  D  P  H  A  N  P  H  Q   191

701  AGCCGTCGCCGCGCGTGGATGTAGTCATCCCCGAAGGCACCGCCTACAAC  750
      P  S  P  R  V  D  V  V  I  P  E  G  T  A  Y  N     207
                                                   +

751  AACACGCTCGAGCACAGCATCTGCACCGCCTTCGAGGCCAGCACCGTCGG  800
      N  T  L  E  H  S  I  C  T  A  F  E  A  S  T  V  G  224

801  CGACGCCGCGGCAGACAACTTCACTGCCGTGTTCGCGCCGGCGATCGCCA  850
      D  A  A  A  D  N  F  T  A  V  F  A  P  A  I  A  K  241
                  +

851  AGCGTCTGGAGGCCGATCTGCCCGGCGTGCAGCTGTCCGCCGACGACGTG  900
      R  L  E  A  D  L  P  G  V  Q  L  S  A  D  D  V     257

901  GTCAATCTGATGGCCATGTGTCCGTTCGAGACGGTCAGCCTGACCGACGA  950
      V  N  L  M  A  M  C  P  F  E  T  V  S  L  T  D  D  274

951  CGCGCACACGCTGTCGCCGTTCTGCGACCTCTTCACCGCCGCCGAGTGGA 1000
      A  H  T  L  S  P  F  C  D  L  F  T  A  A  E  W  T  291

1001 CGCAGTACAACTACCTGCTCTCGCTGGACAAGTACTACGGCTACGGCGGC 1050
      Q  Y  N  Y  L  L  S  L  D  K  Y  Y  G  Y  G  G     307

1051 GGCAATCCGCTGGGCCCCGTGCAGGGCGTGGGCTGGGCGAACGAGCTGAT 1100
      G  N  P  L  G  P  V  Q  G  V  G  W  A  N  E  L  I  324

1101 CGCGCGGCTGACGCGCTCCCCCGTCCACGACCACACCTGCGTCAACAACA 1150
      A  R  L  T  R  S  P  V  H  D  H  T  C  V  N  N  T  341
                                                      +

1151 CCCTCGACGCCAACCCGGCCACCTTCCCGCTGAACGCCACCCTCTACGCG 1200
      L  D  A  N  P  A  T  F  P  L  N  A  T  L  Y  A     357
                                          +

1201 GACTTTTCGCACGACAGTAACCTGGTGTCGATCTTCTGGGCGCTGGGTCT 1250
      D  F  S  H  D  S  N  L  V  S  I  F  W  A  L  G  L  374
```

FIG. 21-B

```
1251 GTACAACGGCACCAAGCCCCTGTCGCAGACCACCGTGGAGGATATCACCC 1300
      Y  N  G  T  K  P  L  S  Q  T  T  V  E  D  I  T  R   391
         +

1301 GGACGGACGGGTACGCGGCCGCCTGGACGGTGCCGTTTGCCGCCCGCGCC 1350
      T  D  G  Y  A  A  A  W  T  V  P  F  A  A  R  A    407

1351 TACATCGAGATGATGCAGTGTCGCGCGGAGAAGCAGCCGCTGGTGCGCGT 1400
      Y  I  E  M  M  Q  C  R  A  E  K  Q  P  L  V  R  V  424

1401 GCTGGTCAACGACCGTGTCATGCCGCTGCACGGCTGCGCGGTGGATAATC 1450
      L  V  N  D  R  V  M  P  L  H  G  C  A  V  D  N  L  441

1451 TGGGCAGGTGTAAACGGGACGACTTTGTGGAGGGACTGAGCTTTGCGCGG 1500
      G  R  C  K  R  D  D  F  V  E  G  L  S  F  A  R     457

1501 GCAGGAGGGAACTGGGCCGAGTGTTTCTGATGTACATGCTGTAGTTAGCT 1550
      A  G  G  N  W  A  E  C  F  *                      466

1551 TTGAGTCCTGAGGTACC                                  1567
```

FIG. 21C

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 2327 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(374..420, 469..1819)

(xi) SEQUENCE DESCRIPTION: SEQ ID NO: 1:

```
TCTAGAACAA TAACAGGTAC TCCCTAGGTA CCCGAAGGAC CTTGTGGAAA ATGTATGGAG      60

GTGGACACGG CACCAACCAC CACCCGCGAT GGCGCACGTG GTGCCCTAAC CCCTTGCTCC     120

CTCAGGATGG AATCCATGTC GACTCTTTAC CCTCACCATC GCCTGGATGA AACCTCCCCG     180

CTAAGCTCAC GACGATCGCT ATTTCCGACC GATTTGACCG TCATGGTGGA GGGCTGATTC     240

GGTCGATGCT CCTGCCTTCA TTTCGGAGTT CGGAGACATG AAAGGCTTAT ATGAGGACGT     300

CCCAGGTCGG GGACGAAATC CGCCCTGGGC TGTGCTCCTT CGTCGGAAAC ATCTGCTGTC     360

CGTGATGGCT ACC ATG GGC TTT CTT GCC ATT GTG CTC TCC GTC GCC TTG        409
            Met Gly Phe Leu Ala Ile Val Leu Ser Val Ala Leu
              1               5                  10
```

-continued

| | | |
|---|---|---|
| CTC TTT AGA AG GTATGCACCC CTCTACGTCC AATTCTCTGG GCACTGACAA<br>Leu Phe Arg Ser<br>15 | | 460 |
| CGGCGCAG C ACA TCG GGC ACC CCG TTG GGC CCC CGG GGC AAA CAT AGC<br>          Thr Ser Gly Thr Pro Leu Gly Pro Arg Gly Lys His Ser<br>                      20                              25 | | 508 |
| GAC TGC AAC TCA GTC GAT CAC GGC TAT CAA TGC TTT CCT GAA CTC TCT<br>Asp Cys Asn Ser Val Asp His Gly Tyr Gln Cys Phe Pro Glu Leu Ser<br>30                   35                40                   45 | | 556 |
| CAT AAA TGG GGA CTC TAC GCG CCC TAC TTC TCC CTC CAG GAC GAG TCT<br>His Lys Trp Gly Leu Tyr Ala Pro Tyr Phe Ser Leu Gln Asp Glu Ser<br>                50                   55                  60 | | 604 |
| CCG TTT CCT CTG GAC GTC CCA GAG GAC TGT CAC ATC ACC TTC GTG CAG<br>Pro Phe Pro Leu Asp Val Pro Glu Asp Cys His Ile Thr Phe Val Gln<br>65                   70                   75 | | 652 |
| GTG CTG GCC CGC CAC GGC GCG CGG AGC CCA ACC CAT AGC AAG ACC AAG<br>Val Leu Ala Arg His Gly Ala Arg Ser Pro Thr His Ser Lys Thr Lys<br>        80                   85                  90 | | 700 |
| GCG TAC GCG GCG ACC ATT GCG GCC ATC CAG AAG AGT GCC ACT GCG TTT<br>Ala Tyr Ala Ala Thr Ile Ala Ala Ile Gln Lys Ser Ala Thr Ala Phe<br>95                   100                 105 | | 748 |
| CCG GGC AAA TAC GCG TTC CTG CAG TCA TAT AAC TAC TCC TTG GAC TCT<br>Pro Gly Lys Tyr Ala Phe Leu Gln Ser Tyr Asn Tyr Ser Leu Asp Ser<br>110                115               120              125 | | 796 |
| GAG GAG CTG ACT CCC TTC GGG CGG AAC CAG CTG CGA GAT CTG GGC GCC<br>Glu Glu Leu Thr Pro Phe Gly Arg Asn Gln Leu Arg Asp Leu Gly Ala<br>               130                 135               140 | | 844 |
| CAG TTC TAC GAG CGC TAC AAC GCC CTC ACC CGA CAC ATC AAC CCC TTC<br>Gln Phe Tyr Glu Arg Tyr Asn Ala Leu Thr Arg His Ile Asn Pro Phe<br>             145                 150               155 | | 892 |
| GTC CGC GCC ACC GAT GCA TCC CGC GTC CAC GAA TCC GCC GAG AAG TTC<br>Val Arg Ala Thr Asp Ala Ser Arg Val His Glu Ser Ala Glu Lys Phe<br>160                165               170 | | 940 |
| GTC GAG GGC TTC CAA ACC GCT CGA CAG GAC GAT CAT CAC GCC AAT CCC<br>Val Glu Gly Phe Gln Thr Ala Arg Gln Asp Asp His His Ala Asn Pro<br>      175               180               185 | | 988 |
| CAC CAG CCT TCG CCT CGC GTG GAC GTG GCC ATC CCC GAA GGC AGC GCC<br>His Gln Pro Ser Pro Arg Val Asp Val Ala Ile Pro Glu Gly Ser Ala<br>190                195               200              205 | | 1036 |
| TAC AAC AAC ACG CTG GAG CAC AGC CTC TGC ACC GCC TTC GAA TCC AGC<br>Tyr Asn Asn Thr Leu Glu His Ser Leu Cys Thr Ala Phe Glu Ser Ser<br>             210                 215               220 | | 1084 |
| ACC GTC GGC GAC GAC GCG GTC GCC AAC TTC ACC GCC GTG TTC GCG CCG<br>Thr Val Gly Asp Asp Ala Val Ala Asn Phe Thr Ala Val Phe Ala Pro<br>             225                 230               235 | | 1132 |
| GCG ATC GCC CAG CGC CTG GAG GCC GAT CTT CCC GGC GTG CAG CTG TCC<br>Ala Ile Ala Gln Arg Leu Glu Ala Asp Leu Pro Gly Val Gln Leu Ser<br>240                245               250 | | 1180 |
| ACC GAC GAC GTG GTC AAC CTG ATG GCC ATG TGT CCG TTC GAG ACG GTC<br>Thr Asp Asp Val Val Asn Leu Met Ala Met Cys Pro Phe Glu Thr Val<br>      255               260               265 | | 1228 |
| AGC CTG ACC GAC GAC GCG CAC ACG CTG TCG CCG TTC TGC GAC CTC TTC<br>Ser Leu Thr Asp Asp Ala His Thr Leu Ser Pro Phe Cys Asp Leu Phe<br>270                275               280              285 | | 1276 |
| ACG GCC ACT GAG TGG ACG CAG TAC AAC TAC CTG CTC TCG CTG GAC AAG<br>Thr Ala Thr Glu Trp Thr Gln Tyr Asn Tyr Leu Leu Ser Leu Asp Lys<br>             290                 295               300 | | 1324 |
| TAC TAC GGC TAC GGC GGG GGC AAT CCG CTG GGT CCG GTG CAG GGG GTC<br>Tyr Tyr Gly Tyr Gly Gly Gly Asn Pro Leu Gly Pro Val Gln Gly Val | | 1372 |

-continued

```
                305                 310                 315
GGC TGG GCG AAC GAG CTG ATG GCG CGG CTA ACG CGC GCC CCC GTG CAC       1420
Gly Trp Ala Asn Glu Leu Met Ala Arg Leu Thr Arg Ala Pro Val His
            320                 325                 330

GAC CAC ACC TGC GTC AAC AAC ACC CTC GAC GCG AGT CCG GCC ACC TTC       1468
Asp His Thr Cys Val Asn Asn Thr Leu Asp Ala Ser Pro Ala Thr Phe
        335                 340                 345

CCG CTG AAC GCC ACC CTC TAC GCC GAC TTC TCC CAC GAC AGC AAC CTG       1516
Pro Leu Asn Ala Thr Leu Tyr Ala Asp Phe Ser His Asp Ser Asn Leu
350                 355                 360                 365

GTG TCG ATC TTC TGG GCG CTG GGC CTG TAC AAC GGC ACC GCG CCG CTG       1564
Val Ser Ile Phe Trp Ala Leu Gly Leu Tyr Asn Gly Thr Ala Pro Leu
                370                 375                 380

TCG CAG ACC TCC GTC GAG AGC GTC TCC CAG ACG GAC GGG TAC GCC GCC       1612
Ser Gln Thr Ser Val Glu Ser Val Ser Gln Thr Asp Gly Tyr Ala Ala
            385                 390                 395

GCC TGG ACG GTG CCG TTC GCC GCT CGC GCG TAC GTC GAG ATG ATG CAG       1660
Ala Trp Thr Val Pro Phe Ala Ala Arg Ala Tyr Val Glu Met Met Gln
        400                 405                 410

TGT CGC GCC GAG AAG GAG CCG CTG GTG CGC GTG CTG GTC AAC GAC CGG       1708
Cys Arg Ala Glu Lys Glu Pro Leu Val Arg Val Leu Val Asn Asp Arg
    415                 420                 425

GTC ATG CCG CTG CAT GGC TGC CCT ACG GAC AAG CTG GGG CGG TGC AAG       1756
Val Met Pro Leu His Gly Cys Pro Thr Asp Lys Leu Gly Arg Cys Lys
430                 435                 440                 445

CGG GAC GCT TTC GTC GCG GGG CTG AGC TTT GCG CAG GCG GGC GGG AAC       1804
Arg Asp Ala Phe Val Ala Gly Leu Ser Phe Ala Gln Ala Gly Gly Asn
                450                 455                 460

TGG GCG GAT TGT TTC TGATGTTGAG AAGAAAGGTA GATAGATAGG TAGTACATAT       1859
Trp Ala Asp Cys Phe
                465

GGATTGCTCG GCTCTGGGTC GTTGCCCACA ATGCATATTA CGCCCGTCAA CTGCCTTGCG     1919

CCATCCACCT CTCACCCTGG ACGCAACCGA GCGGTCTACC CTGCACACGG CTTCCACCGC     1979

GACGCGCACG GATAAGGCGC TTTTGTTACG GGGTTGGGGC TGGGGGCAGC CGGAGCCGGA     2039

GAGAGAGACC AGCGTGAAAA ACGACAGAAC ATAGATATCA ATTCGACGCC AATTCATGCA     2099

GAGTAGTATA CAGACGAACT GAAACAAACA CATCACTTCC CTCGCTCCTC TCCTGTAGAA     2159

GACGCTCCCA CCAGCCGCTT CTGGCCCTTA TTCCCGTACG CTAGGTAGAC CAGTCAGCCA     2219

GACGCATGCC TCACAAGAAC GGGGGCGGGG GACACACTCC GCTCGTACAG CACCCACGAC     2279

GTGTACAGGA AAACCGGCAG CGCCACAATC GTCGAGAGCC ATCTGCAG                  2327

(2) INFORMATION FOR SEQ ID NO: 2:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Phe Leu Ala Ile Val Leu Ser Val Ala Leu Leu Phe Arg Ser
1               5                   10                  15

Thr Ser Gly Thr Pro Leu Gly Pro Arg Gly Lys His Ser Asp Cys Asn
            20                  25                  30

Ser Val Asp His Gly Tyr Gln Cys Phe Pro Glu Leu Ser His Lys Trp
        35                  40                  45
```

-continued

```
Gly Leu Tyr Ala Pro Tyr Phe Ser Leu Gln Asp Glu Ser Pro Phe Pro
         50                  55                  60

Leu Asp Val Pro Glu Asp Cys His Ile Thr Phe Val Gln Val Leu Ala
 65                  70                  75                  80

Arg His Gly Ala Arg Ser Pro Thr His Ser Lys Thr Lys Ala Tyr Ala
                 85                  90                  95

Ala Thr Ile Ala Ala Ile Gln Lys Ser Ala Thr Ala Phe Pro Gly Lys
            100                 105                 110

Tyr Ala Phe Leu Gln Ser Tyr Asn Tyr Ser Leu Asp Ser Glu Glu Leu
            115                 120                 125

Thr Pro Phe Gly Arg Asn Gln Leu Arg Asp Leu Gly Ala Gln Phe Tyr
            130                 135                 140

Glu Arg Tyr Asn Ala Leu Thr Arg His Ile Asn Pro Phe Val Arg Ala
145                 150                 155                 160

Thr Asp Ala Ser Arg Val His Glu Ser Ala Glu Lys Phe Val Glu Gly
                165                 170                 175

Phe Gln Thr Ala Arg Gln Asp His His Ala Asn Pro His Gln Pro
            180                 185                 190

Ser Pro Arg Val Asp Val Ala Ile Pro Glu Gly Ser Ala Tyr Asn Asn
        195                 200                 205

Thr Leu Glu His Ser Leu Cys Thr Ala Phe Glu Ser Ser Thr Val Gly
        210                 215                 220

Asp Asp Ala Val Ala Asn Phe Thr Ala Val Phe Ala Pro Ala Ile Ala
225                 230                 235                 240

Gln Arg Leu Glu Ala Asp Leu Pro Gly Val Gln Leu Ser Thr Asp Asp
            245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Thr
            275                 280                 285

Glu Trp Thr Gln Tyr Asn Tyr Leu Leu Ser Leu Asp Lys Tyr Tyr Gly
    290                 295                 300

Tyr Gly Gly Gly Asn Pro Leu Gly Pro Val Gln Gly Val Gly Trp Ala
305                 310                 315                 320

Asn Glu Leu Met Ala Arg Leu Thr Arg Ala Pro Val His Asp His Thr
            325                 330                 335

Cys Val Asn Asn Thr Leu Asp Ala Ser Pro Ala Thr Phe Pro Leu Asn
            340                 345                 350

Ala Thr Leu Tyr Ala Asp Phe Ser His Asp Ser Asn Leu Val Ser Ile
            355                 360                 365

Phe Trp Ala Leu Gly Leu Tyr Asn Gly Thr Ala Pro Leu Ser Gln Thr
    370                 375                 380

Ser Val Glu Ser Val Ser Gln Thr Asp Gly Tyr Ala Ala Ala Trp Thr
385                 390                 395                 400

Val Pro Phe Ala Ala Arg Ala Tyr Val Glu Met Met Gln Cys Arg Ala
                405                 410                 415

Glu Lys Glu Pro Leu Val Arg Val Leu Val Asn Asp Arg Val Met Pro
            420                 425                 430

Leu His Gly Cys Pro Thr Asp Lys Leu Gly Arg Cys Lys Arg Asp Ala
            435                 440                 445

Phe Val Ala Gly Leu Ser Phe Ala Gln Ala Gly Asn Trp Ala Asp
    450                 455                 460

Cys Phe
```

(2) INFORMATION FOR SEQ ID NO: 3:

(i) SEQUENCE CHARACTERISTICS:
        (A) LENGTH: 3995 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(2208..2263, 2321..3725)

(xi) SEQUENCE DESCRIPTION: SEQ ID NO: 3:

```
GTCGACGAGG CACACCACGC CCGTCCTCGG CGGGTCCGAG AGGGCCGGGC TCGGGTTCGA      60

CAAGGAGACG GGCGTCCCTT CGGGCGCGGC TGCGGGTGTG GGTGTTGCTG TGGACGGTGA     120

GGAGGGGGAC GGGCTGGGCG TTGATGACGG TACGAATGCG AACGGACACA GGCCGCTGAG     180

CGTGGGTGTT GCGTTCTAAT CTTTCTTTGT GTGGGTGTGT ACGTGTGGGT GTGTATGTGT     240

TTGGGGGGGG GAATGTTCTT GGTAATTATC TTTCTACCCT TCTTCTCTTT CCTTTATTCT     300

GTTCAGCAGG TATACCCCGT GTAAGTGTAC AGGATTATGG GACGGGTGGG TGGATGGACT     360

ACTTCTAGAA GGACGGATAA GGAAAAAGGG GAAACACGAA TATGGCGCCC TGGGTGGCGC     420

GTCGAGCTGG ATGCTTGACG CCGGTCTGGC AAACATTTTC TTCTTCTAGC ACCCAACCTA     480

GTACTTGATA GAGTGTTTCG GGGCCAGGCG GTTTGCGCTG TGTTTTTACC AATCACCAAC     540

TAGTGCTACT ACTATTATTG CGGCTGTTGA TGCAGCCGTG TACCAAAAAT GCCGCGGCAT     600

CTCCATTGAT ACTTGTAGTT TTGATAGATC AATATTTGGG AGGTTGCGCT GGGCTGCTCT     660

GAAACCCCTC TCTCTTGCTG TACGTAACGT ATGTGCACAG TATGTCACCG ACAAAGACGA     720

TTGCATGCGC ATCGTTTTTT GTTGTGTTTC AGGCCTCGCT CGTGTCTAGG GTATAAACAC     780

ATTGAAGACT ACATATGCGC AAGACGTTGA CATTAACGGG GTCCTGCAGC CGCCGCAGGT     840

GCATGTCGTG ATTAATACCA CGCGCCTGCG TAAATTAGCT AGCCGCCGCC CTGTTTCACT     900

CGGTTAGAGA CGGACAGGTG AGACGGGTCT CGGTTAAGCA AGCAAATTGG AATGCAAGGT     960

TGAAGGTGTA ATCTGCATAG CGTGGAAATG AGAGGGCTCT GTGGGCAGCC AGGAAGGTGA    1020

GACGAAATGA GGAAAGAGGC ACCAGAAGCT GTTGTTCTGA AGTGCCCGTG GTCATAGCTC    1080

CAGGATTAAG TACGGATGTC CCATGCCAAG CTGCTGGCTT CGAAAGCGAG TACGGAGTAG    1140

TGTCCATTGT TCACGAGGGA TCCCCAATGT GTTAGACATG CCTGAATCAA TTTTGTCCTA    1200

TTTTTGGATT TCAACTGTTT CTCTCGACTG TGCTCGGTAG CGACTATGCC GCAAGGTACA    1260

CTACATGTTG TACAATAATC ATACATCGAC CTTCCGTAGG AGTGCTGAAA TACCCGACCT    1320

GCTCTCTCTA GCAGGTGCCT AATGGCTTTC GTGTAACTCG ATCGAAACGG ATCAGCAAGT    1380

CCATTTGCTG TTGGTTGAGA TGTACGATTT ACAAACACGT GGAGAGGTGA GCCACAGCGA    1440

TAGGCTTCTG GAAGGATTCT GGCGTCTCGG AAAGAGGGCC ACTCGCCCCA CTAACCGGCG    1500

CCGATCTTGA CATGGGGCTC GCAGGGGGTT TAAGTGCACA CTACGGAGTA CGGATTACAC    1560

AGTAGTGTAT GGGTGGGGGC GAGTTTGGGT GGCCTTGTGT GGGGCTCACC GGCTGCCTGT    1620

TCTCGGGGAG TCTTGGCGGG CCGATTGGAC CCACCTAACC ACGGGTAGTC TTGGCCCGGC    1680

CAACTCACAC CGCCCTCATG TTTCGGAGCC AGTCAGGGAG GCAGGCACTA CTCAGTCAGG    1740

TACACACGTC GGGCTCCTCG ATGCTGGGTG ACATCGAGGC GATACTGCAT TCCAACTACG    1800
```

-continued

```
GTTGGCATAG GAGGTATCCT ATTCTAGAGC TGTTCTACGC CGGAACGTAA CCCGGGATAA   1860

CCCGGGATAT CGCTTCCCTG AGCGAGCGCG CTGCTGAGGA TCATACAACC CAACAACCGA   1920

CGACGGTGCA AGAAGGTTGG GGGAAGGAAG AAATCAAGGA AAAAAAAATA GGGGGGGTGG   1980

GGACCAAGAG AGAAAGAAAG GAGAAAAGGG TGGGGGAGG GAAGAGAAAA AAAAAACGGA    2040

GGAATATGGC GTCGCTCTTC GACTGGTTCC GGAAGGGGGC ATCTGGGTAC ACATATGCAC   2100

CTCTTCCGCA CGGCAGGGAT ATAAACCGGG AGTGCAGTCC CACCGATCAT GCTGAGTCCG   2160

CCCGTCTCCA GACTTCACGG TCGCAGAGGA CTAGACGCGC GGTGAAG ATG ACT GGC    2216
                                                   Met Thr Gly
                                                     1

CTC GGA GTG ATG GTG GTG ATG GTC GGC TTC CTG GCG ATC GCC TCT  CT    2263
Leu Gly Val Met Val Val Met Val Gly Phe Leu Ala Ile Ala Ser  Leu
      5              10                  15

GTAAGCAGCG ATTCCAGGGG TCCGGTGTGC GTTAAAAGAA AAAGCTAACG CCACCAG A    2321

CAA TCC GAG TCC CGG CCA TGC GAC ACC CCA GAC TTG GGC TTC CAG TGT    2369
Gln Ser Glu Ser Arg Pro Cys Asp Thr Pro Asp Leu Gly Phe Gln Cys
 20              25                  30                  35

GGT ACG GCC ATT TCC CAC TTC TGG GGC CAG TAC TCG CCC TAC TTC TCC    2417
Gly Thr Ala Ile Ser His Phe Trp Gly Gln Tyr Ser Pro Tyr Phe Ser
              40                  45                  50

GTG CCC TCG GAG CTG GAT GCT TCG ATC CCC GAC GAC TGC GAG GTG ACG    2465
Val Pro Ser Glu Leu Asp Ala Ser Ile Pro Asp Asp Cys Glu Val Thr
              55                  60                  65

TTT GCC CAA GTC CTC TCC CGC CAC GGC GCG AGG GCG CCG ACG CTC AAA    2513
Phe Ala Gln Val Leu Ser Arg His Gly Ala Arg Ala Pro Thr Leu Lys
              70                  75                  80

CGG GCC GCG AGC TAC GTC GAT CTC ATC GAC AGG ATC CAC CAT GGC GCC    2561
Arg Ala Ala Ser Tyr Val Asp Leu Ile Asp Arg Ile His His Gly Ala
 85                  90                  95

ATC TCC TAC GGG CCG GGC TAC GAG TTC CTC AGG ACG TAT GAC TAC ACC    2609
Ile Ser Tyr Gly Pro Gly Tyr Glu Phe Leu Arg Thr Tyr Asp Tyr Thr
100                 105                 110                 115

CTG GGC GCC GAC GAG CTC ACC CGG ACG GGC CAG CAG CAG ATG GTC AAC    2657
Leu Gly Ala Asp Glu Leu Thr Arg Thr Gly Gln Gln Gln Met Val Asn
                120                 125                 130

TCG GGC ATC AAG TTT TAC CGC CGC TAC CGC GCT CTC GCC CGC AAG TCG    2705
Ser Gly Ile Lys Phe Tyr Arg Arg Tyr Arg Ala Leu Ala Arg Lys Ser
            135                 140                 145

ATC CCC TTC GTC CGC ACC GCC GGC CAG GAC CGC GTC GTC CAC TCG GCC    2753
Ile Pro Phe Val Arg Thr Ala Gly Gln Asp Arg Val Val His Ser Ala
            150                 155                 160

GAG AAC TTC ACC CAG GGC TTC CAC TCT GCC CTG CTC GCC GAC CGC GGG    2801
Glu Asn Phe Thr Gln Gly Phe His Ser Ala Leu Leu Ala Asp Arg Gly
165                 170                 175

TCC ACC GTC CGG CCC ACC CTC CCC TAT GAC ATG GTC GTC ATC CCG GAA    2849
Ser Thr Val Arg Pro Thr Leu Pro Tyr Asp Met Val Val Ile Pro Glu
180                 185                 190                 195

ACC GCC GGC GCC AAC AAC ACG CTC CAC AAC GAC CTC TGC ACC GCC TTC    2897
Thr Ala Gly Ala Asn Asn Thr Leu His Asn Asp Leu Cys Thr Ala Phe
                200                 205                 210

GAG GAA GGC CCG TAC TCG ACC ATC GGC GAC GAC GCC CAA GAC ACC TAC    2945
Glu Glu Gly Pro Tyr Ser Thr Ile Gly Asp Asp Ala Gln Asp Thr Tyr
            215                 220                 225

CTC TCC ACC TTC GCC GGA CCC ATC ACC GCC CGG GTC AAC GCC AAC CTG    2993
Leu Ser Thr Phe Ala Gly Pro Ile Thr Ala Arg Val Asn Ala Asn Leu
            230                 235                 240

CCG GGC GCC AAC CTG ACC GAC GCC GAC ACG GTC GCG CTG ATG GAC CTC    3041
```

```
Pro Gly Ala Asn Leu Thr Asp Ala Asp Thr Val Ala Leu Met Asp Leu
        245                 250                 255

TGC CCC TTC GAG ACG GTC GCC TCC TCC TCC TCC GAC CCG GCA ACG GCG      3089
Cys Pro Phe Glu Thr Val Ala Ser Ser Ser Ser Asp Pro Ala Thr Ala
260                 265                 270                 275

GAC GCG GGG GGC GGC AAC GGG CGG CCG CTG TCG CCC TTC TGC CGC CTG      3137
Asp Ala Gly Gly Gly Asn Gly Arg Pro Leu Ser Pro Phe Cys Arg Leu
                280                 285                 290

TTC AGC GAG TCC GAG TGG CGC GCG TAC GAC TAC CTG CAG TCG GTG GGC      3185
Phe Ser Glu Ser Glu Trp Arg Ala Tyr Asp Tyr Leu Gln Ser Val Gly
            295                 300                 305

AAG TGG TAC GGG TAC GGG CCG GGC AAC CCG CTG GGG CCG ACG CAG GGG      3233
Lys Trp Tyr Gly Tyr Gly Pro Gly Asn Pro Leu Gly Pro Thr Gln Gly
        310                 315                 320

GTC GGG TTC GTC AAC GAG CTG CTG GCG CGG CTG GCC GGG GTC CCC GTG      3281
Val Gly Phe Val Asn Glu Leu Leu Ala Arg Leu Ala Gly Val Pro Val
    325                 330                 335

CGC GAC GGC ACC AGC ACC AAC CGC ACC CTC GAC GGC GAC CCG CGC ACC      3329
Arg Asp Gly Thr Ser Thr Asn Arg Thr Leu Asp Gly Asp Pro Arg Thr
340                 345                 350                 355

TTC CCG CTC GGC CGG CCC CTC TAC GCC GAC TTC AGC CAC GAC AAC GAC      3377
Phe Pro Leu Gly Arg Pro Leu Tyr Ala Asp Phe Ser His Asp Asn Asp
                360                 365                 370

ATG ATG GGC GTC CTC GGC GCC CTC GGC GCC TAC GAC GGC GTC CCG CCC      3425
Met Met Gly Val Leu Gly Ala Leu Gly Ala Tyr Asp Gly Val Pro Pro
            375                 380                 385

CTC GAC AAG ACC GCC CGC CGC GAC CCG GAA GAG CTC GGC GGG TAC GCG      3473
Leu Asp Lys Thr Ala Arg Arg Asp Pro Glu Glu Leu Gly Gly Tyr Ala
        390                 395                 400

GCC AGC TGG GCC GTC CCG TTC GCC GCC AGG ATC TAC GTC GAG AAG ATG      3521
Ala Ser Trp Ala Val Pro Phe Ala Ala Arg Ile Tyr Val Glu Lys Met
    405                 410                 415

CGG TGC AGC GGC GGC GGC GGC GGC GGC GGC GGC GAG GGG CGG CAG          3569
Arg Cys Ser Gly Gly Gly Gly Gly Gly Gly Gly Glu Gly Arg Gln
420                 425                 430                 435

GAG AAG GAT GAG GAG ATG GTC AGG GTG CTG GTG AAC GAC CGG GTG ATG      3617
Glu Lys Asp Glu Glu Met Val Arg Val Leu Val Asn Asp Arg Val Met
                440                 445                 450

ACG CTG AAG GGG TGC GGC GCC GAC GAG AGG GGG ATG TGT ACG CTA GAA      3665
Thr Leu Lys Gly Cys Gly Ala Asp Glu Arg Gly Met Cys Thr Leu Glu
            455                 460                 465

CGG TTC ATC GAA AGC ATG GCG TTT GCG AGG GGG AAC GGC AAG TGG GAT      3713
Arg Phe Ile Glu Ser Met Ala Phe Ala Arg Gly Asn Gly Lys Trp Asp
        470                 475                 480

CTC TGC TTT GCT TGATATGCCC ACGCCCGAGA TTGAACAGAA CTTGTGATGG          3765
Leu Cys Phe Ala
485

GGGTAGAGTG TGGTATTCGA GATGATAGTT CACAGTTTTC GGGAATCAAA AATCGGTTAG    3825

ACTGGCGAAA TTCAAGTCTG GGGCCTGCGG CGTCTGCATT CTCCGTTCCC TGTTGTTACC    3885

TTCTTAATGG TTTTTTTTTA TTTTTTATTT TTCTTAAATT TTCACACAAA CCTTTTATTG    3945

TCTTTTTTTC TTCTTTTTCT TCTTCTGCAC ATCGGATGGG AATTGTCGAC              3995

(2) INFORMATION FOR SEQ ID NO: 4:

(i) SEQUENCE CHARACTERISTICS:
        (A) LENGTH: 487 amino acids
        (B) TYPE: amino acid
        (D) TOPOLOGY: linear
```

(ii) MOLECULE TYPE: protein (xi) SEQUENCE DESCRIPTION: SEQ ID NO: 4:

```
Met Thr Gly Leu Gly Val Met Val Met Val Gly Phe Leu Ala Ile
 1               5                  10                  15

Ala Ser Leu Gln Ser Glu Ser Arg Pro Cys Asp Thr Pro Asp Leu Gly
            20                  25                  30

Phe Gln Cys Gly Thr Ala Ile Ser His Phe Trp Gly Gln Tyr Ser Pro
            35                  40                  45

Tyr Phe Ser Val Pro Ser Glu Leu Asp Ala Ser Ile Pro Asp Asp Cys
    50                  55                  60

Glu Val Thr Phe Ala Gln Val Leu Ser Arg His Gly Ala Arg Ala Pro
65                  70                  75                  80

Thr Leu Lys Arg Ala Ala Ser Tyr Val Asp Leu Ile Asp Arg Ile His
                85                  90                  95

His Gly Ala Ile Ser Tyr Gly Pro Gly Tyr Glu Phe Leu Arg Thr Tyr
                100                 105                 110

Asp Tyr Thr Leu Gly Ala Asp Glu Leu Thr Arg Thr Gly Gln Gln Gln
            115                 120                 125

Met Val Asn Ser Gly Ile Lys Phe Tyr Arg Arg Tyr Arg Ala Leu Ala
    130                 135                 140

Arg Lys Ser Ile Pro Phe Val Arg Thr Ala Gly Gln Asp Arg Val Val
145                 150                 155                 160

His Ser Ala Glu Asn Phe Thr Gln Gly Phe His Ser Ala Leu Leu Ala
                165                 170                 175

Asp Arg Gly Ser Thr Val Arg Pro Thr Leu Pro Tyr Asp Met Val Val
            180                 185                 190

Ile Pro Glu Thr Ala Gly Ala Asn Asn Thr Leu His Asn Asp Leu Cys
    195                 200                 205

Thr Ala Phe Glu Glu Gly Pro Tyr Ser Thr Ile Gly Asp Asp Ala Gln
    210                 215                 220

Asp Thr Tyr Leu Ser Thr Phe Ala Gly Pro Ile Thr Ala Arg Val Asn
225                 230                 235                 240

Ala Asn Leu Pro Gly Ala Asn Leu Thr Asp Ala Asp Thr Val Ala Leu
                245                 250                 255

Met Asp Leu Cys Pro Phe Glu Thr Val Ala Ser Ser Ser Asp Pro
            260                 265                 270

Ala Thr Ala Asp Ala Gly Gly Asn Gly Arg Pro Leu Ser Pro Phe
            275                 280                 285

Cys Arg Leu Phe Ser Glu Ser Glu Trp Arg Ala Tyr Asp Tyr Leu Gln
    290                 295                 300

Ser Val Gly Lys Trp Tyr Gly Tyr Gly Pro Gly Asn Pro Leu Gly Pro
305                 310                 315                 320

Thr Gln Gly Val Gly Phe Val Asn Glu Leu Leu Ala Arg Leu Ala Gly
                325                 330                 335

Val Pro Val Arg Asp Gly Thr Ser Thr Asn Arg Thr Leu Asp Gly Asp
            340                 345                 350

Pro Arg Thr Phe Pro Leu Gly Arg Pro Leu Tyr Ala Asp Phe Ser His
            355                 360                 365

Asp Asn Asp Met Met Gly Val Leu Gly Ala Leu Gly Ala Tyr Asp Gly
    370                 375                 380

Val Pro Pro Leu Asp Lys Thr Ala Arg Arg Asp Pro Glu Glu Leu Gly
385                 390                 395                 400
```

```
Gly Tyr Ala Ala Ser Trp Ala Val Pro Phe Ala Ala Arg Ile Tyr Val
                405                 410                 415

Glu Lys Met Arg Cys Ser Gly Gly Gly Gly Gly Gly Gly Gly Gly Glu
            420                 425                 430

Gly Arg Gln Glu Lys Asp Glu Glu Met Val Arg Val Leu Val Asn Asp
        435                 440                 445

Arg Val Met Thr Leu Lys Gly Cys Gly Ala Asp Glu Arg Gly Met Cys
    450                 455                 460

Thr Leu Glu Arg Phe Ile Glu Ser Met Ala Phe Ala Arg Gly Asn Gly
465                 470                 475                 480

Lys Trp Asp Leu Cys Phe Ala
                485

(2) INFORMATION FOR SEQ ID NO: 5:

(i) SEQUENCE CHARACTERISTICS:
        (A) LENGTH: 103 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 2..103

(xi) SEQUENCE DESCRIPTION: SEQ ID NO: 5:

G ACC TTG GCT CGC AAC CAC ACA GAC ACG CTG TCT CCG TTC TGC GCT        46
  Thr Leu Ala Arg Asn His Thr Asp Thr Leu Ser Pro Phe Cys Ala
  1               5                   10                  15

CTT TCC ACG CAA GAG GAG TGG CAA GCA TAT GAC TAC TAC CAA AGT CTG      94
Leu Ser Thr Gln Glu Glu Trp Gln Ala Tyr Asp Tyr Tyr Gln Ser Leu
                20                  25                  30

GGG AAA TAC                                                         103
Gly Lys Tyr (2) INFORMATION FOR SEQ ID NO: 6:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO: 6:

Thr Leu Ala Arg Asn His Thr Asp Thr Leu Ser Pro Phe Cys Ala Leu
1               5                   10                  15

Ser Thr Gln Glu Glu Trp Gln Ala Tyr Asp Tyr Tyr Gln Ser Leu Gly
            20                  25                  30

Asn (2) INFORMATION FOR SEQ ID NO: 7:

(i) SEQUENCE CHARACTERISTICS:
        (A) LENGTH: 106 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
```

```
                (B) LOCATION: 2..106

(xi) SEQUENCE DESCRIPTION: SEQ ID NO: 7:

T ACG GTA GCG CGC ACC AGC GAC GCA AGT CAG CTG TCA CCG TTC TGT            46
  Thr Val Ala Arg Thr Ser Asp Ala Ser Gln Leu Ser Pro Phe Cys
   1               5                  10                  15

CAA CTC TTC ACT CAC AAT GAG TGG AAG AAG TAC AAC TAC CTT CAG TCC          94
Gln Leu Phe Thr His Asn Glu Trp Lys Lys Tyr Asn Tyr Leu Gln Ser
             20                  25                  30

TTG GGC AAG TAC                                                         106
Leu Gly Lys Tyr
             35

(2) INFORMATION FOR SEQ ID NO: 8:

(i) SEQUENCE CHARACTERISTICS:
            (A) LENGTH: 35 amino acids
            (B) TYPE: amino acid
            (D) TOPOLOGY: linear (ii) MOLECULE TYPE: protein (xi) SEQUENCE DESCRIPTION: SEQ ID NO: 8:

Thr Val Ala Arg Thr Ser Asp Ala Ser Gln Leu Ser Pro Phe Cys Gln
 1               5                  10                  15

Leu Phe Thr His Asn Glu Trp Lys Lys Tyr Asn Tyr Leu Gln Ser Leu
             20                  25                  30

Gly Lys Tyr
             35

(2) INFORMATION FOR SEQ ID NO: 9:

(i) SEQUENCE CHARACTERISTICS:
            (A) LENGTH: 109 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 2..109

(xi) SEQUENCE DESCRIPTION: SEQ ID NO: 9:

C ACC ATG GCG CGC ACC GCC ACT CGG AAC CGT AGT CTG TCT CCA TTT            46
  Thr Met Ala Arg Thr Ala Thr Arg Asn Arg Ser Leu Ser Pro Phe
   1               5                  10                  15

TGT GCC ATC TTC ACT GAA AAG GAG TGG CTG CAG TAC GAC TAC CTT CAA          94
Cys Ala Ile Phe Thr Glu Lys Glu Trp Leu Gln Tyr Asp Tyr Leu Gln
             20                  25                  30

TCT CTA TCA AAG TAC                                                     109
Ser Leu Ser Lys Tyr
             35

(2) INFORMATION FOR SEQ ID NO: 10:

(i) SEQUENCE CHARACTERISTICS:
            (A) LENGTH: 36 amino acids
            (B) TYPE: amino acid
            (D) TOPOLOGY: linear (ii) MOLECULE TYPE: protein (xi) SEQUENCE DESCRIPTION: SEQ ID NO: 10:

Thr Met Ala Arg Thr Ala Thr Arg Asn Arg Ser Leu Ser Pro Phe Cys
```

```
              1               5              10              15
Ala Ile Phe Thr Glu Lys Glu Trp Leu Gln Tyr Asp Tyr Leu Gln Ser
                    20              25              30

Leu Ser Lys Tyr
        35

(2) INFORMATION FOR SEQ ID NO: 11:

(i) SEQUENCE CHARACTERISTICS:
        (A) LENGTH: 1912 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: CDS
         (B) LOCATION: 1..1396

(ix) FEATURE:
         (A) NAME/KEY: CDS
         (B) LOCATION: 1..1398

(xi) SEQUENCE DESCRIPTION: SEQ ID NO: 11:

ATG GGC GTC TCT GCT GTT CTA CTT CCT TTG TAT CTC CTA GCT GGA GTC         48
Met Gly Val Ser Ala Val Leu Leu Pro Leu Tyr Leu Leu Ala Gly Val
 1               5                  10                  15

ACC TCC GGA CTG GCA GTC CCC GCC TCG AGA AAT CAA TCC ACT TGC GAT         96
Thr Ser Gly Leu Ala Val Pro Ala Ser Arg Asn Gln Ser Thr Cys Asp
            20                  25                  30

ACG GTC GAT CAA GGG TAT CAA TGC TTC TCC GAG ACT TCG CAT CTT TGG        144
Thr Val Asp Gln Gly Tyr Gln Cys Phe Ser Glu Thr Ser His Leu Trp
        35                  40                  45

GGT CAA TAC GCG CCG TTC TTC TCT CTG GCA AAC GAA TCG GTC ATC TCC        192
Gly Gln Tyr Ala Pro Phe Phe Ser Leu Ala Asn Glu Ser Val Ile Ser
    50                  55                  60

CCT GAT GTG CCC GCC GGT TGC AGA GTC ACT TTC GCT CAG GTC CTC TCC        240
Pro Asp Val Pro Ala Gly Cys Arg Val Thr Phe Ala Gln Val Leu Ser
65                  70                  75                  80

CGT CAT GGA GCG CGG TAT CCG ACC GAG TCC AAG GGC AAG AAA TAC TCC        288
Arg His Gly Ala Arg Tyr Pro Thr Glu Ser Lys Gly Lys Lys Tyr Ser
                85                  90                  95

GCT CTC ATT GAG GAG ATC CAG CAG AAC GTG ACC ACC TTT GAT GGA AAA        336
Ala Leu Ile Glu Glu Ile Gln Gln Asn Val Thr Thr Phe Asp Gly Lys
            100                 105                 110

TAT GCC TTC CTG AAG ACA TAC AAC TAC AGC TTG GGT GCA GAT GAC CTG        384
Tyr Ala Phe Leu Lys Thr Tyr Asn Tyr Ser Leu Gly Ala Asp Asp Leu
        115                 120                 125

ACT CCC TTC GGA GAG CAG GAG CTA GTC AAC TCC GGC ATC AAG TTC TAC        432
Thr Pro Phe Gly Glu Gln Glu Leu Val Asn Ser Gly Ile Lys Phe Tyr
    130                 135                 140

CAG CGC TAC AAC GCC CTC ACC CGA CAC ATC AAC CCC TTC GTC CGC GCC        480
Gln Arg Tyr Asn Ala Leu Thr Arg His Ile Asn Pro Phe Val Arg Ala
145                 150                 155                 160

ACC GAT GCA TCC CGC GTC CAC GAA TCC GCC GAG AAG TTC GTC GAG GGC        528
Thr Asp Ala Ser Arg Val His Glu Ser Ala Glu Lys Phe Val Glu Gly
                165                 170                 175

TTC CAA ACC GCT CGA CAG GAC GAT CAT CAC GCC AAT CCC CAC CAG CCT        576
Phe Gln Thr Ala Arg Gln Asp Asp His His Ala Asn Pro His Gln Pro
            180                 185                 190

TCG CCT CGC GTG GAC GTG GCC ATC CCC GAA GGC AGC GCC TAC AAC AAC        624
Ser Pro Arg Val Asp Val Ala Ile Pro Glu Gly Ser Ala Tyr Asn Asn
```

```
            195                 200                     205
ACG CTG GAG CAC AGC CTC TGC ACC GCC TTC GAA TCC AGC ACC GTC GGC      672
Thr Leu Glu His Ser Leu Cys Thr Ala Phe Glu Ser Ser Thr Val Gly
    210                 215                 220

GAC GAC GCG GTC GCC AAC TTC ACC GCC GTG TTC GCG CCG GCG ATC GCC      720
Asp Asp Ala Val Ala Asn Phe Thr Ala Val Phe Ala Pro Ala Ile Ala
225                 230                 235                 240

CAG CGC CTG GAG GCC GAT CTT CCC GGC GTG CAG CTG TCC ACC GAC GAC      768
Gln Arg Leu Glu Ala Asp Leu Pro Gly Val Gln Leu Ser Thr Asp Asp
                245                 250                 255

GTG GTC AAC CTG ATG GCC ATG TGT CCG TTC GAG ACG GTC AGC CTG ACC      816
Val Val Asn Leu Met Ala Met Cys Pro Phe Glu Thr Val Ser Leu Thr
            260                 265                 270

GAC GAC GCG CAC ACG CTG TCG CCG TTC TGC GAC CTC TTC ACG GCC ACT      864
Asp Asp Ala His Thr Leu Ser Pro Phe Cys Asp Leu Phe Thr Ala Thr
        275                 280                 285

GAG TGG ACG CAG TAC AAC TAC CTG CTC TCG CTG GAC AAG TAC TAC GGC      912
Glu Trp Thr Gln Tyr Asn Tyr Leu Leu Ser Leu Asp Lys Tyr Tyr Gly
    290                 295                 300

TAC GGC GGG GGC AAT CCG CTG GGT CCG GTG CAG GGG GTC GGC TGG GCG      960
Tyr Gly Gly Gly Asn Pro Leu Gly Pro Val Gln Gly Val Gly Trp Ala
305                 310                 315                 320

AAC GAG CTG ATG GCG CGG CTA ACG CGC GCC CCC GTG CAC GAC CAC ACC     1008
Asn Glu Leu Met Ala Arg Leu Thr Arg Ala Pro Val His Asp His Thr
                325                 330                 335

TGC GTC AAC AAC ACC CTC GAC GCG AGT CCG GCC ACC TTC CCG CTG AAC     1056
Cys Val Asn Asn Thr Leu Asp Ala Ser Pro Ala Thr Phe Pro Leu Asn
            340                 345                 350

GCC ACC CTC TAC GCC GAC TTC TCC CAC GAC AGC AAC CTG GTG TCG ATC     1104
Ala Thr Leu Tyr Ala Asp Phe Ser His Asp Ser Asn Leu Val Ser Ile
        355                 360                 365

TTC TGG GCG CTG GGC CTG TAC AAC GGC ACC GCG CCG CTG TCG CAG ACC     1152
Phe Trp Ala Leu Gly Leu Tyr Asn Gly Thr Ala Pro Leu Ser Gln Thr
    370                 375                 380

TCC GTC GAG AGC GTC TCC CAG ACG GAC GGG TAC GCC GCC GCC TGG ACG     1200
Ser Val Glu Ser Val Ser Gln Thr Asp Gly Tyr Ala Ala Ala Trp Thr
385                 390                 395                 400

GTG CCG TTC GCC GCT CGC GCG TAC GTC GAG ATG ATG CAG TGT CGC GCC     1248
Val Pro Phe Ala Ala Arg Ala Tyr Val Glu Met Met Gln Cys Arg Ala
                405                 410                 415

GAG AAG GAG CCG CTG GTG CGC GTG CTG GTC AAC GAC CGG GTC ATG CCG     1296
Glu Lys Glu Pro Leu Val Arg Val Leu Val Asn Asp Arg Val Met Pro
            420                 425                 430

CTG CAT GGC TGC CCT ACG GAC AAG CTG GGG CGG TGC AAG CGG GAC GCT     1344
Leu His Gly Cys Pro Thr Asp Lys Leu Gly Arg Cys Lys Arg Asp Ala
        435                 440                 445

TTC GTC GCG GGG CTG AGC TTT GCG CAG GCG GGC GGG AAC TGG GCG GAT     1392
Phe Val Ala Gly Leu Ser Phe Ala Gln Ala Gly Gly Asn Trp Ala Asp
    450                 455                 460

TGT TTC TGATGTTGAG AAGAAAGGTA GATAGATAGG TAGTACATAT GGATTGCTCG     1448
Cys Phe
465

GCTCTGGGTC GTTGCCCACA ATGCATATTA CGCCCGTCAA CTGCCTTGCG CCATCCACCT   1508

CTCACCCTGG ACGCAACCGA GCGGTCTACC CTGCACACGG CTTCCACCGC GACGCGCACG   1568

GATAAGGCGC TTTTGTTACG GGGTTGGGGC TGGGGGCAGC CGGAGCCGGA GAGAGAGACC   1628

AGCGTGAAAA ACGACAGAAC ATAGATATCA ATTCGACGCC AATTCATGCA GAGTAGTATA   1688

CAGACGAACT GAAACAAACA CATCACTTCC CTCGCTCCTC TCCTGTAGAA GACGCTCCCA   1748
```

```
CCAGCCGCTT CTGGCCCTTA TTCCCGTACG CTAGGTAGAC CAGTCAGCCA GACGCATGCC    1808

TCACAAGAAC GGGGGCGGGG GACACACTCC GCTCGTACAG CACCCACGAC GTGTACAGGA    1868

AAACCGGCAG CGCCACAATC GTCGAGAGCC ATCTGCAGGA ATTC                     1912
```

(2) INFORMATION FOR SEQ ID NO: 12:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Gly Val Ser Ala Val Leu Leu Pro Leu Tyr Leu Ala Gly Val
 1               5                  10                  15

Thr Ser Gly Leu Ala Val Pro Ala Ser Arg Asn Gln Ser Thr Cys Asp
                20                  25                  30

Thr Val Asp Gln Gly Tyr Gln Cys Phe Ser Glu Thr Ser His Leu Trp
            35                  40                  45

Gly Gln Tyr Ala Pro Phe Phe Ser Leu Ala Asn Glu Ser Val Ile Ser
        50                  55                  60

Pro Asp Val Pro Ala Gly Cys Arg Val Thr Phe Ala Gln Val Leu Ser
65                  70                  75                  80

Arg His Gly Ala Arg Tyr Pro Thr Glu Ser Lys Gly Lys Lys Tyr Ser
                85                  90                  95

Ala Leu Ile Glu Glu Ile Gln Gln Asn Val Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Asn Ala Leu Thr Arg His Ile Asn Pro Phe Val Arg Ala
145                 150                 155                 160

Thr Asp Ala Ser Arg Val His Glu Ser Ala Glu Lys Phe Val Glu Gly
                165                 170                 175

Phe Gln Thr Ala Arg Gln Asp Asp His His Ala Asn Pro His Gln Pro
            180                 185                 190

Ser Pro Arg Val Asp Val Ala Ile Pro Glu Gly Ser Ala Tyr Asn Asn
        195                 200                 205

Thr Leu Glu His Ser Leu Cys Thr Ala Phe Glu Ser Ser Thr Val Gly
    210                 215                 220

Asp Asp Ala Val Ala Asn Phe Thr Ala Val Phe Ala Pro Ala Ile Ala
225                 230                 235                 240

Gln Arg Leu Glu Ala Asp Leu Pro Gly Val Gln Leu Ser Thr Asp Asp
                245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Thr
        275                 280                 285

Glu Trp Thr Gln Tyr Asn Tyr Leu Leu Ser Leu Asp Lys Tyr Tyr Gly
    290                 295                 300

Tyr Gly Gly Gly Asn Pro Leu Gly Pro Val Gln Gly Val Gly Trp Ala
305                 310                 315                 320
```

```
Asn Glu Leu Met Ala Arg Leu Thr Arg Ala Pro Val His Asp His Thr
            325                 330                 335

Cys Val Asn Asn Thr Leu Asp Ala Ser Pro Ala Thr Phe Pro Leu Asn
            340                 345                 350

Ala Thr Leu Tyr Ala Asp Phe Ser His Asp Ser Asn Leu Val Ser Ile
            355                 360                 365

Phe Trp Ala Leu Gly Leu Tyr Asn Gly Thr Ala Pro Leu Ser Gln Thr
        370                 375                 380

Ser Val Glu Ser Val Ser Gln Thr Asp Gly Tyr Ala Ala Ala Trp Thr
385                 390                 395                 400

Val Pro Phe Ala Ala Arg Ala Tyr Val Glu Met Met Gln Cys Arg Ala
                405                 410                 415

Glu Lys Glu Pro Leu Val Arg Val Leu Val Asn Asp Arg Val Met Pro
                420                 425                 430

Leu His Gly Cys Pro Thr Asp Lys Leu Gly Arg Cys Lys Arg Asp Ala
            435                 440                 445

Phe Val Ala Gly Leu Ser Phe Ala Gln Ala Gly Gly Asn Trp Ala Asp
        450                 455                 460

Cys Phe
465

(2) INFORMATION FOR SEQ ID NO: 13:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 13:

GACGGTCAGC CTGACCGACG ACGCGCACAC GCTGTCGCCG TTCTGCGACC TCTTCACCGC        60

CGCCGAGTGG ACGCAGTACA ACTACCTGCT CTCGCTGGAC AAGTACTACG TC              112

(2) INFORMATION FOR SEQ ID NO: 14:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 14:

CAGTAACCTG GTGTCGATCT TCTGGNCGCT GGGTCTGTAC AACGGCACCA AGCCCCTGTC        60

GCAGACCACC GTGGAGGATA TCACCCGGAC G                                      91

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

ATGGAYATGT GYTCNTTYGA                                                    20
```

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
TTRCCRGCRC CRTGNCCRTA                                              20
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
TAYGCNGAYT TYTCNCAYGA                                              20
```

(2) INFORMATION FOR SEQ ID NO: 18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
CGRTCRTTNA CNAGNACNC                                               19
```

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
AGTCCGGAGG TGACTCCAGC TAGGAGATAC                                   30
```

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

```
CTGTCGCCGT TCTGCGACCT C                                            21
```

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

CGGTGCCGTT GTACAGACCC AGC                              23

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

ATGGGCTTTC TTGCCATTGT                                 20

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

TCAGAAACAA TCCGCCCAAG TT                              22

(2) INFORMATION FOR SEQ ID NO: 24:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 2..106

(ix) FEATURE:
        (A) NAME/KEY: Region
        (B) LOCATION: 32..52

```
       (D) OTHER INFORMATION: /note="position of Aterr21 primer"

(xi) SEQUENCE DESCRIPTION: SEQ ID NO: 24:

G ACG GTC AGC CTG ACC GAC GAC GCG CAC ACG CTG TCG CCG TTC TGC          46
  Thr Val Ser Leu Thr Asp Asp Ala His Thr Leu Ser Pro Phe Cys
   1               5                  10                  15

GAC CTC TTC ACC GCC GCC GAG TGG ACG CAG TAC AAC TAC CTG CTC TCG        94
Asp Leu Phe Thr Ala Ala Glu Trp Thr Gln Tyr Asn Tyr Leu Leu Ser
                20                  25                  30

CTG GAC AAG TAC                                                       106
Leu Asp Lys Tyr
            35

(2) INFORMATION FOR SEQ ID NO: 25:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO: 25:

Thr Val Ser Leu Thr Asp Asp Ala His Thr Leu Ser Pro Phe Cys Asp
 1               5                  10                  15

Leu Phe Thr Ala Ala Glu Trp Thr Gln Tyr Asn Tyr Leu Leu Ser Leu
                20                  25                  30

Asp Lys Tyr
        35

(2) INFORMATION FOR SEQ ID NO: 26:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 2..181

(ix) FEATURE:
        (A) NAME/KEY: Region
        (B) LOCATION: 28..50
        (D) OTHER INFORMATION: /note="position of Aterr58 primer"

(xi) SEQUENCE DESCRIPTION: SEQ ID NO: 26:

C AGT AAC CTG GTG TCG ATC TTC TGG GCG CTG GGT CTG TAC AAC GGC          46
  Ser Asn Leu Val Ser Ile Phe Trp Ala Leu Gly Leu Tyr Asn Gly
   1               5                  10                  15

ACC AAG CCC CTG TCG CAG ACC ACC GTG GAG GAT ATC ACC CGG ACG GAC        94
Thr Lys Pro Leu Ser Gln Thr Thr Val Glu Asp Ile Thr Arg Thr Asp
                20                  25                  30

GGG TAC GCG GCC GCC TGG ACG GTG CCG TTT GCC GCC CGC GCC TAC ATC       142
Gly Tyr Ala Ala Ala Trp Thr Val Pro Phe Ala Ala Arg Ala Tyr Ile
                35                  40                  45

GAG ATG ATG CAG TGT CGC GCG GAG AAG CAG CCG CTG GTA                   181
Glu Met Met Gln Cys Arg Ala Glu Lys Gln Pro Leu Val
                50                  55                  60
```

(2) INFORMATION FOR SEQ ID NO: 27:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 27:

```
Ser Asn Leu Val Ser Ile Phe Trp Ala Leu Gly Leu Tyr Asn Gly Thr
 1               5                  10                  15

Lys Pro Leu Ser Gln Thr Thr Val Glu Asp Ile Thr Arg Thr Asp Gly
                20                  25                  30

Tyr Ala Ala Ala Trp Thr Val Pro Phe Ala Ala Arg Ala Tyr Ile Glu
                35                  40                  45

Met Met Gln Cys Arg Ala Glu Lys Gln Pro Leu Val
                50                  55                  60
```

(2) INFORMATION FOR SEQ ID NO: 28:

(i) SEQUENCE CHARACTERISTICS:
        (A) LENGTH: 1931 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: join(158..204, 259..1600)

(ix) FEATURE:
        (A) NAME/KEY: intron
        (B) LOCATION: 205..258

(ix) FEATURE:
        (A) NAME/KEY: misc_feature
        (B) LOCATION: 1000..1105
        (D) OTHER INFORMATION: /note= "Position of PCR fragment"

(xi) SEQUENCE DESCRIPTION: SEQ ID NO: 28:

```
TCTGTAACCG ATAGCGGACC GACTAGGCAT CGTTGATCCA CAATATCTCA GACAATGCAA      60

CTCAGTCGAA TATGAAGGGC TACAGCCAGC ATTTAAATAC GGCCGTCTAG GTCGGGCTCC     120

GGGGATGAGG AGGAGCAGGC TCGTGTTCAT TTCGGTC ATG GCT TTT TTC ACG GTC     175
                                        Met Ala Phe Phe Thr Val
                                         1               5

GCT CTT TCG CTT TAT TAC TTG CTA TCG AG  GTGAGATCTC TACAATATCT        224
Ala Leu Ser Leu Tyr Tyr Leu Leu Ser  Arg
             10                  15

GTCTGCTTAG TTGAATTGGT ACTTATCTGT ACAG A GTC TCT GCT CAG GCC CCA       277
                                       Val Ser Ala Gln Ala Pro
                                                       20

GTG GTC CAG AAT CAT TCA TGC AAT ACG GCG GAC GGT GGA TAT CAA TGC       325
Val Val Gln Asn His Ser Cys Asn Thr Ala Asp Gly Gly Tyr Gln Cys
             25                  30                  35

TTC CCC AAT GTC TCT CAT GTT TGG GGT CAG TAC TCG CCG TAC TTC TCC       373
Phe Pro Asn Val Ser His Val Trp Gly Gln Tyr Ser Pro Tyr Phe Ser
     40                  45                  50

ATC GAG CAG GAG TCA GCT ATC TCT GAG GAC GTG CCT CAT GGC TGT GAG       421
```

```
Ile Glu Gln Glu Ser Ala Ile Ser Glu Asp Val Pro His Gly Cys Glu
 55                  60                  65                  70

GTT ACC TTT GTG CAG GTG CTC TCG CGG CAT GGG GCT AGG TAT CCG ACA        469
Val Thr Phe Val Gln Val Leu Ser Arg His Gly Ala Arg Tyr Pro Thr
             75                  80                  85

GAG TCG AAG AGT AAG GCG TAC TCG GGG TTG ATT GAA GCA ATC CAG AAG        517
Glu Ser Lys Ser Lys Ala Tyr Ser Gly Leu Ile Glu Ala Ile Gln Lys
             90                  95                 100

AAT GCT ACC TCT TTT TGG GGA CAG TAT GCT TTT CTG GAG AGT TAT AAC        565
Asn Ala Thr Ser Phe Trp Gly Gln Tyr Ala Phe Leu Glu Ser Tyr Asn
            105                 110                 115

TAT ACC CTC GGC GCG GAT GAC TTG ACT ATC TTC GGC GAG AAC CAG ATG        613
Tyr Thr Leu Gly Ala Asp Asp Leu Thr Ile Phe Gly Glu Asn Gln Met
        120                 125                 130

GTT GAT TCG GGT GCC AAG TTC TAC CGA CGG TAT AAG AAT CTC GCC AGG        661
Val Asp Ser Gly Ala Lys Phe Tyr Arg Arg Tyr Lys Asn Leu Ala Arg
135                 140                 145                 150

AAA AAT ACT CCT TTT ATC CGT GCA TCA GGG TCT GAC CGT GTC GTT GCG        709
Lys Asn Thr Pro Phe Ile Arg Ala Ser Gly Ser Asp Arg Val Val Ala
                155                 160                 165

TCT GCG GAG AAG TTC ATT AAT GGA TTT CGC AAG GCT CAG CTC CAC GAC        757
Ser Ala Glu Lys Phe Ile Asn Gly Phe Arg Lys Ala Gln Leu His Asp
            170                 175                 180

CAT GGC TCC AAA CGT GCT ACG CCA GTT GTC AAT GTG ATT ATC CCT GAA        805
His Gly Ser Lys Arg Ala Thr Pro Val Val Asn Val Ile Ile Pro Glu
            185                 190                 195

ATC GAT GGG TTT AAC AAC ACC CTG GAC CAT AGC ACG TGC GTA TCT TTT        853
Ile Asp Gly Phe Asn Asn Thr Leu Asp His Ser Thr Cys Val Ser Phe
        200                 205                 210

GAG AAT GAT GAG CGG GCG GAT GAA ATT GAA GCC AAT TTC ACG GCA ATT        901
Glu Asn Asp Glu Arg Ala Asp Glu Ile Glu Ala Asn Phe Thr Ala Ile
215                 220                 225                 230

ATG GGA CCT CCG ATC CGC AAA CGT CTG GAA AAT GAC CTC CCT GGC ATC        949
Met Gly Pro Pro Ile Arg Lys Arg Leu Glu Asn Asp Leu Pro Gly Ile
                235                 240                 245

AAA CTT ACA AAC GAG AAT GTA ATA TAT TTG ATG GAT ATG TGC TCT TTC        997
Lys Leu Thr Asn Glu Asn Val Ile Tyr Leu Met Asp Met Cys Ser Phe
            250                 255                 260

GAC ACC ATG GCG CGC ACC GCC CAC GGA ACC GAG CTG TCT CCA TTT TGT       1045
Asp Thr Met Ala Arg Thr Ala His Gly Thr Glu Leu Ser Pro Phe Cys
            265                 270                 275

GCC ATC TTC ACT GAA AAG GAG TGG CTG CAG TAC GAC TAC CTT CAA TCT       1093
Ala Ile Phe Thr Glu Lys Glu Trp Leu Gln Tyr Asp Tyr Leu Gln Ser
        280                 285                 290

CTA TCA AAG TAC TAC GGC TAC GGT GCC GGA AGC CCC CTT GGC CCA GCT       1141
Leu Ser Lys Tyr Tyr Gly Tyr Gly Ala Gly Ser Pro Leu Gly Pro Ala
295                 300                 305                 310

CAG GGA ATT GGC TTC ACC AAC GAG CTG ATT GCC CGA CTA ACG CAA TCG       1189
Gln Gly Ile Gly Phe Thr Asn Glu Leu Ile Ala Arg Leu Thr Gln Ser
                315                 320                 325

CCC GTC CAG GAC AAC ACA AGC ACC AAC CAC ACT CTA GAC TCG AAC CCA       1237
Pro Val Gln Asp Asn Thr Ser Thr Asn His Thr Leu Asp Ser Asn Pro
            330                 335                 340

GCC ACA TTT CCG CTC GAC AGG AAG CTC TAC GCC GAC TTC TCC CAC GAC       1285
Ala Thr Phe Pro Leu Asp Arg Lys Leu Tyr Ala Asp Phe Ser His Asp
            345                 350                 355

AAT AGC ATG ATA TCG ATA TTC TTC GCC ATG GGT CTG TAC AAC GGC ACC       1333
Asn Ser Met Ile Ser Ile Phe Phe Ala Met Gly Leu Tyr Asn Gly Thr
        360                 365                 370
```

```
CAG CCG CTG TCA ATG GAT TCC GTG GAG TCG ATC CAG GAG ATG GAC GGT     1381
Gln Pro Leu Ser Met Asp Ser Val Glu Ser Ile Gln Glu Met Asp Gly
375             380                 385                 390

TAC GCG GCG TCT TGG ACT GTT CCG TTT GGT GCG AGG GCT TAC TTT GAG     1429
Tyr Ala Ala Ser Trp Thr Val Pro Phe Gly Ala Arg Ala Tyr Phe Glu
                395                 400                 405

CTC ATG CAG TGC GAG AAG AAG GAG CCG CTT GTG CGG GTA TTA GTG AAT     1477
Leu Met Gln Cys Glu Lys Lys Glu Pro Leu Val Arg Val Leu Val Asn
            410                 415                 420

GAT CGC GTT GTT CCT CTT CAT GGC TGC GCA GTT GAC AAG TTT GGA CGG     1525
Asp Arg Val Val Pro Leu His Gly Cys Ala Val Asp Lys Phe Gly Arg
        425                 430                 435

TGC ACT TTG GAC GAT TGG GTA GAG GGC TTG AAT TTT GCA AGG AGC GGC     1573
Cys Thr Leu Asp Asp Trp Val Glu Gly Leu Asn Phe Ala Arg Ser Gly
    440                 445                 450

GGG AAC TGG AAG ACT TGT TTT ACC CTA TAAAGGGCGT TGCTCATTC            1620
Gly Asn Trp Lys Thr Cys Phe Thr Leu
455             460

ATAAGTGTTG TGCAGGTATA GGAAGGTTAG GGAATTAGCT GTTTGGCTTT ACTCTTATTA    1680

GACCAAGAAT GATTTGTTTG TTCTCAAGGC CTTCTAGCAT ATCGTCAAGT GGGATAAATC    1740

ACCTATCCTC CATGTGTAGG TGAACCCGCT CTTGCATCAA CCTCTTGTGT TTCAGAGTAG    1800

TTTCACCAAA CATATCCTCG TGTCCTCTCT TCTGCTCTTC GGTCTCATAT TACACTGTTC    1860

TCTATCTATA TCGTCAACAA AACTACCACC CAAACACCAA ATGTCACACT TTCCAGCACG    1920

AAATTTCTTC G                                                        1931

(2) INFORMATION FOR SEQ ID NO: 29:

(i) SEQUENCE CHARACTERISTICS:
        (A) LENGTH: 463 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 26
        (D) OTHER INFORMATION: /note="potential N-glycosylation site"

(ix) FEATURE:
        (A) NAME/KEY: misc_feature
        (B) LOCATION: 41
        (D) OTHER INFORMATION: /note="potential N-glycosylation site"

(ix) FEATURE:
        (A) NAME/KEY: misc_feature
        (B) LOCATION: 103
        (D) OTHER INFORMATION: /note="potential N-glycosylation site"

(ix) FEATURE:
        (A) NAME/KEY: misc_feature
        (B) LOCATION: 118
        (D) OTHER INFORMATION: /note="potential N-glycosylation site"

(ix) FEATURE:
        (A) NAME/KEY: misc_feature
        (B) LOCATION: 203
        (D) OTHER INFORMATION: /note="potential N-glycosylation site"

(ix) FEATURE:
        (A) NAME/KEY: misc_feature
        (B) LOCATION: 226
        (D) OTHER INFORMATION: /note="potential N-glycosylation site"

(ix) FEATURE:
        (A) NAME/KEY: misc_feature
        (B) LOCATION: 331
```

-continued (D) OTHER INFORMATION: /note="potential N-glycosylation site"

(ix) FEATURE:
          (A) NAME/KEY: misc_feature
          (B) LOCATION: 335
          (D) OTHER INFORMATION: /note="potential N-glycosylation site"

(ix) FEATURE:
          (A) NAME/KEY: misc_feature
          (B) LOCATION: 372
          (D) OTHER INFORMATION: /note="potential N-glycosylation site"

(xi) SEQUENCE DESCRIPTION: SEQ ID NO: 29:

Met Ala Phe Phe Thr Val Ala Leu Ser Leu Tyr Tyr Leu Leu Ser Arg
 1               5                  10                  15

Val Ser Ala Gln Ala Pro Val Val Gln Asn His Ser Cys Asn Thr Ala
            20                  25                  30

Asp Gly Gly Tyr Gln Cys Phe Pro Asn Val Ser His Val Trp Gly Gln
        35                  40                  45

Tyr Ser Pro Tyr Phe Ser Ile Glu Gln Glu Ser Ala Ile Ser Glu Asp
    50                  55                  60

Val Pro His Gly Cys Glu Val Thr Phe Val Gln Val Leu Ser Arg His
65                  70                  75                  80

Gly Ala Arg Tyr Pro Thr Glu Ser Lys Ser Lys Ala Tyr Ser Gly Leu
                85                  90                  95

Ile Glu Ala Ile Gln Lys Asn Ala Thr Ser Phe Trp Gly Gln Tyr Ala
            100                 105                 110

Phe Leu Glu Ser Tyr Asn Tyr Thr Leu Gly Ala Asp Asp Leu Thr Ile
        115                 120                 125

Phe Gly Glu Asn Gln Met Val Asp Ser Gly Ala Lys Phe Tyr Arg Arg
    130                 135                 140

Tyr Lys Asn Leu Ala Arg Lys Asn Thr Pro Phe Ile Arg Ala Ser Gly
145                 150                 155                 160

Ser Asp Arg Val Val Ala Ser Ala Glu Lys Phe Ile Asn Gly Phe Arg
                165                 170                 175

Lys Ala Gln Leu His Asp His Gly Ser Lys Arg Ala Thr Pro Val Val
            180                 185                 190

Asn Val Ile Ile Pro Glu Ile Asp Gly Phe Asn Asn Thr Leu Asp His
        195                 200                 205

Ser Thr Cys Val Ser Phe Glu Asn Asp Glu Arg Ala Asp Glu Ile Glu
    210                 215                 220

Ala Asn Phe Thr Ala Ile Met Gly Pro Pro Ile Arg Lys Arg Leu Glu
225                 230                 235                 240

Asn Asp Leu Pro Gly Ile Lys Leu Thr Asn Glu Asn Val Ile Tyr Leu
                245                 250                 255

Met Asp Met Cys Ser Phe Asp Thr Met Ala Arg Thr Ala His Gly Thr
            260                 265                 270

Glu Leu Ser Pro Phe Cys Ala Ile Phe Thr Glu Lys Glu Trp Leu Gln
        275                 280                 285

Tyr Asp Tyr Leu Gln Ser Ser Leu Lys Tyr Tyr Gly Tyr Gly Ala Gly
    290                 295                 300

Ser Pro Leu Gly Pro Ala Gln Gly Ile Gly Phe Thr Asn Glu Leu Ile
305                 310                 315                 320

Ala Arg Leu Thr Gln Ser Pro Val Gln Asp Asn Thr Ser Thr Asn His
                325                 330                 335

Thr Leu Asp Ser Asn Pro Ala Thr Phe Pro Leu Asp Arg Lys Leu Tyr
            340                 345                 350

```
Ala Asp Phe Ser His Asp Asn Ser Met Ile Ser Ile Phe Phe Ala Met
        355                 360                 365

Gly Leu Tyr Asn Gly Thr Gln Pro Leu Ser Met Asp Ser Val Glu Ser
        370                 375                 380

Ile Gln Glu Met Asp Gly Tyr Ala Ala Ser Trp Thr Val Pro Phe Gly
385                 390                 395                 400

Ala Arg Ala Tyr Phe Glu Leu Met Gln Cys Glu Lys Lys Glu Pro Leu
                405                 410                 415

Val Arg Val Leu Val Asn Asp Arg Val Val Pro Leu His Gly Cys Ala
            420                 425                 430

Val Asp Lys Phe Gly Arg Cys Thr Leu Asp Asp Trp Val Glu Gly Leu
            435                 440                 445

Asn Phe Ala Arg Ser Gly Gly Asn Trp Lys Thr Cys Phe Thr Leu
        450                 455                 460
```

(2) INFORMATION FOR SEQ ID NO: 30:

(i) SEQUENCE CHARACTERISTICS:
        (A) LENGTH: 1845 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: join(288..334, 390..1740)

(ix) FEATURE:
        (A) NAME/KEY: intron
        (B) LOCATION: 335..389

(ix) FEATURE:
        (A) NAME/KEY: misc_feature
        (B) LOCATION: 1134..1236
        (D) OTHER INFORMATION: /note= "Position of PCR fragment"

(xi) SEQUENCE DESCRIPTION: SEQ ID NO: 30:

```
TTCCACGCTG AAAGCCTGAC TGCGATTTCC AAGCTGCATG CAGGCTGCTC AACTGCCTGC     60

TTATCTTCAT CAGACGCAGA TACACAACCT GGTCTGTAGA TGCACCCATG ACGGACGAAC    120

GCACCGCTCT CTTGGCCTCC AGGGACCCGG AGGTCGAGGG CGATGAGGTC GCGCCCTCGA    180

CGGCCTCCCA GTCCCTGTTG CAGTTGAGAT CTCGCTGCGA ACGTCGACCG CAGATATGGT    240

TGTCTTCGAC GTTTTCTCGC CTTCGAGGAA GAATTGCTGC TGTGACG ATG AGT CTG      296
                                                 Met Ser Leu
                                                   1

TTG TTG CTG GTG CTG TCC GGC GGG TTG GTC GCG TTA  TA GTATGCTCCT       344
Leu Leu Leu Val Leu Ser Gly Gly Leu Val Ala Leu  Tyr
        5                   10                  15

TCTCTCTGGT CATATTGTTT TCTGCTAACG TTCTCATAAT TGAAG T GTC TCA AGA      399
                                                    Val Ser Arg

AAT CCG CAT GTT GAT AGC CAC TCT TGC AAT ACA GTG GAA GGA GGG TAT     447
Asn Pro His Val Asp Ser His Ser Cys Asn Thr Val Glu Gly Gly Tyr
 20                  25                  30                  35

CAG TGT CGT CCA GAA ATC TCC CAC TCC TGG GGC CAG TAT TCT CCA TTC     495
Gln Cys Arg Pro Glu Ile Ser His Ser Trp Gly Gln Tyr Ser Pro Phe
            40                  45                  50
```

```
TTC TCC CTG GCA GAC CAG TCG GAG ATC TCG CCA GAT GTC CCA CAG AAC      543
Phe Ser Leu Ala Asp Gln Ser Glu Ile Ser Pro Asp Val Pro Gln Asn
             55                  60                  65

TGC AAG ATT ACG TTT GTC CAG CTG CTT TCT CGT CAC GGC GCT AGA TAC      591
Cys Lys Ile Thr Phe Val Gln Leu Leu Ser Arg His Gly Ala Arg Tyr
         70                  75                  80

CCT ACG TCT TCC AAG ACG GAG CTG TAT TCG CAG CTG ATC AGT CGG ATT      639
Pro Thr Ser Ser Lys Thr Glu Leu Tyr Ser Gln Leu Ile Ser Arg Ile
         85                  90                  95

CAG AAG ACG GCG ACT GCG TAC AAA GGC TAC TAT GCC TTC TTG AAA GAC      687
Gln Lys Thr Ala Thr Ala Tyr Lys Gly Tyr Tyr Ala Phe Leu Lys Asp
100             105                 110                 115

TAC AGA TAC CAG CTG GGA GCG AAC GAC CTG ACG CCC TTT GGG GAA AAC      735
Tyr Arg Tyr Gln Leu Gly Ala Asn Asp Leu Thr Pro Phe Gly Glu Asn
                120                 125                 130

CAG ATG ATC CAG TTG GGC ATC AAG TTT TAT AAC CAT TAC AAG AGT CTC      783
Gln Met Ile Gln Leu Gly Ile Lys Phe Tyr Asn His Tyr Lys Ser Leu
                135                 140                 145

GCC AGG AAT GCC GTC CCA TTC GTT CGT TGC TCC GGC TCT GAT CGG GTC      831
Ala Arg Asn Ala Val Pro Phe Val Arg Cys Ser Gly Ser Asp Arg Val
        150                 155                 160

ATT GCC TCG GGG AGA CTT TTC ATC GAA GGT TTC CAG AGC GCC AAA GTG      879
Ile Ala Ser Gly Arg Leu Phe Ile Glu Gly Phe Gln Ser Ala Lys Val
        165                 170                 175

CTG GAT CCT CAT TCA GAC AAG CAT GAC GCT CCT CCC ACG ATC AAC GTG      927
Leu Asp Pro His Ser Asp Lys His Asp Ala Pro Pro Thr Ile Asn Val
180             185                 190                 195

ATC ATC GAG GAG GGT CCG TCC TAC AAT AAC ACG CTC GAC ACC GGC AGC      975
Ile Ile Glu Glu Gly Pro Ser Tyr Asn Asn Thr Leu Asp Thr Gly Ser
                200                 205                 210

TGT CCA GTC TTT GAG GAC AGC AGC GGG GGA CAT GAC GCA CAG GAA AAG     1023
Cys Pro Val Phe Glu Asp Ser Ser Gly Gly His Asp Ala Gln Glu Lys
        215                 220                 225

TTC GCA AAG CAA TTC GCA CCA GCT ATC CTG GAA AAG ATC AAG GAC CAT     1071
Phe Ala Lys Gln Phe Ala Pro Ala Ile Leu Glu Lys Ile Lys Asp His
        230                 235                 240

CTT CCC GGC GTG GAC CTG GCC GTG TCG GAT GTA CCG TAC TTG ATG GAC     1119
Leu Pro Gly Val Asp Leu Ala Val Ser Asp Val Pro Tyr Leu Met Asp
        245                 250                 255

TTG TGT CCG TTT GAG ACC TTG GCT CGC AAC CAC ACA GAC ACG CTG TCT     1167
Leu Cys Pro Phe Glu Thr Leu Ala Arg Asn His Thr Asp Thr Leu Ser
260             265                 270                 275

CCG TTC TGC GCT CTT TCC ACG CAA GAG GAG TGG CAA GCA TAT GAC TAC     1215
Pro Phe Cys Ala Leu Ser Thr Gln Glu Glu Trp Gln Ala Tyr Asp Tyr
                280                 285                 290

TAC CAA AGT CTG GGG AAA TAC TAT GGC AAT GGC GGG GGT AAC CCG TTG     1263
Tyr Gln Ser Leu Gly Lys Tyr Tyr Gly Asn Gly Gly Gly Asn Pro Leu
                295                 300                 305

GGG CCA GCC CAA GGC GTG GGG TTT GTC AAC GAG TTG ATT GCT CGC ATG     1311
Gly Pro Ala Gln Gly Val Gly Phe Val Asn Glu Leu Ile Ala Arg Met
        310                 315                 320

ACC CAT AGC CCT GTC CAG GAC TAC ACC ACG GTC AAC CAC ACT CTT GAC     1359
Thr His Ser Pro Val Gln Asp Tyr Thr Thr Val Asn His Thr Leu Asp
        325                 330                 335

TCG AAT CCG GCG ACA TTC CCT TTG AAC GCG ACG CTG TAC GCA GAT TTC     1407
Ser Asn Pro Ala Thr Phe Pro Leu Asn Ala Thr Leu Tyr Ala Asp Phe
340             345                 350                 355

AGC CAC GAC AAC ACA ATG ACG TCA ATT TTC GCG GCC TTG GGC CTG TAC     1455
Ser His Asp Asn Thr Met Thr Ser Ile Phe Ala Ala Leu Gly Leu Tyr
                360                 365                 370
```

```
AAC GGG ACC GCG AAG CTG TCC ACG ACC GAG ATC AAG TCC ATT GAA GAG       1503
Asn Gly Thr Ala Lys Leu Ser Thr Thr Glu Ile Lys Ser Ile Glu Glu
            375                 380                 385

ACG GAC GGC TAC TCG GCG GCG TGG ACC GTT CCG TTC GGG GGG CGA GCC       1551
Thr Asp Gly Tyr Ser Ala Ala Trp Thr Val Pro Phe Gly Gly Arg Ala
            390                 395                 400

TAT ATC GAG ATG ATG CAG TGT GAT GAT TCG GAT GAG CCA GTC GTT CGG       1599
Tyr Ile Glu Met Met Gln Cys Asp Asp Ser Asp Glu Pro Val Val Arg
    405                 410                 415

GTG CTG GTC AAC GAC CGG GTG GTG CCA CTG CAT GGC TGC GAG GTG GAC       1647
Val Leu Val Asn Asp Arg Val Val Pro Leu His Gly Cys Glu Val Asp
420                 425                 430                 435

TCC CTG GGG CGA TGC AAA CGA GAC GAC TTT GTC AGG GGA CTG AGT TTT       1695
Ser Leu Gly Arg Cys Lys Arg Asp Asp Phe Val Arg Gly Leu Ser Phe
                440                 445                 450

GCG CGA CAG GGT GGG AAC TGG GAG GGG TGT TAC GCT GCT TCT GAG           1740
Ala Arg Gln Gly Gly Asn Trp Glu Gly Cys Tyr Ala Ala Ser Glu
                455                 460                 465

TAGGTTTATT CAGCGAGTTT CGACCTTTCT ATCCTTCAAA CACTGCACAA AGACACACTG     1800

CATGAAATGG TAACAGGCCT GGAGCGTTTT AGAAGGAAAA AAGTT                     1845

(2) INFORMATION FOR SEQ ID NO: 31:

(i) SEQUENCE CHARACTERISTICS:
        (A) LENGTH: 466 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 204
        (D) OTHER INFORMATION: /note="potential N-glycosylation site"

(ix) FEATURE:
        (A) NAME/KEY: misc_feature
        (B) LOCATION: 269
        (D) OTHER INFORMATION: /note="potential N-glycosylation site"

(ix) FEATURE:
        (A) NAME/KEY: misc_feature
        (B) LOCATION: 335
        (D) OTHER INFORMATION: /note="potential N-glycosylation site"

(ix) FEATURE:
        (A) NAME/KEY: misc_feature
        (B) LOCATION: 348
        (D) OTHER INFORMATION: /note="potential N-glycosylation site"

(ix) FEATURE:
        (A) NAME/KEY: misc_feature
        (B) LOCATION: 372
        (D) OTHER INFORMATION: /note="potential N-glycosylation site"

(xi) SEQUENCE DESCRIPTION: SEQ ID NO: 31:

Met Ser Leu Leu Leu Leu Val Leu Ser Gly Gly Leu Val Ala Leu Tyr
 1               5                  10                  15

Val Ser Arg Asn Pro His Val Asp Ser His Ser Cys Asn Thr Val Glu
                20                  25                  30

Gly Gly Tyr Gln Cys Arg Pro Glu Ile Ser His Ser Trp Gly Gln Tyr
            35                  40                  45

Ser Pro Phe Phe Ser Leu Ala Asp Gln Ser Glu Ile Ser Pro Asp Val
        50                  55                  60

Pro Gln Asn Cys Lys Ile Thr Phe Val Gln Leu Leu Ser Arg His Gly
```

```
                65                  70                  75                  80
Ala Arg Tyr Pro Thr Ser Ser Lys Thr Glu Leu Tyr Ser Gln Leu Ile
                    85                  90                  95

Ser Arg Ile Gln Lys Thr Ala Thr Ala Tyr Lys Gly Tyr Tyr Ala Phe
                100                 105                 110

Leu Lys Asp Tyr Arg Tyr Gln Leu Gly Ala Asn Asp Leu Thr Pro Phe
                115                 120                 125

Gly Glu Asn Gln Met Ile Gln Leu Gly Ile Lys Phe Tyr Asn His Tyr
            130                 135                 140

Lys Ser Leu Ala Arg Asn Ala Val Pro Phe Val Arg Cys Ser Gly Ser
145                 150                 155                 160

Asp Arg Val Ile Ala Ser Gly Arg Leu Phe Ile Glu Gly Phe Gln Ser
                165                 170                 175

Ala Lys Val Leu Asp Pro His Ser Asp Lys His Asp Ala Pro Pro Thr
                180                 185                 190

Ile Asn Val Ile Ile Glu Glu Gly Pro Ser Tyr Asn Asn Thr Leu Asp
                195                 200                 205

Thr Gly Ser Cys Pro Val Phe Glu Asp Ser Ser Gly Gly His Asp Ala
            210                 215                 220

Gln Glu Lys Phe Ala Lys Gln Phe Ala Pro Ala Ile Leu Glu Lys Ile
225                 230                 235                 240

Lys Asp His Leu Pro Gly Val Asp Leu Ala Val Ser Asp Val Pro Tyr
                245                 250                 255

Leu Met Asp Leu Cys Pro Phe Glu Thr Leu Ala Arg Asn His Thr Asp
                260                 265                 270

Thr Leu Ser Pro Phe Cys Ala Leu Ser Thr Gln Glu Glu Trp Gln Ala
                275                 280                 285

Tyr Asp Tyr Tyr Gln Ser Leu Gly Lys Tyr Tyr Gly Asn Gly Gly Gly
            290                 295                 300

Asn Pro Leu Gly Pro Ala Gln Gly Val Gly Phe Val Asn Glu Leu Ile
305                 310                 315                 320

Ala Arg Met Thr His Ser Pro Val Gln Asp Tyr Thr Thr Val Asn His
                325                 330                 335

Thr Leu Asp Ser Asn Pro Ala Thr Phe Pro Leu Asn Ala Thr Leu Tyr
                340                 345                 350

Ala Asp Phe Ser His Asp Asn Thr Met Thr Ser Ile Phe Ala Ala Leu
                355                 360                 365

Gly Leu Tyr Asn Gly Thr Ala Lys Leu Ser Thr Thr Glu Ile Lys Ser
            370                 375                 380

Ile Glu Glu Thr Asp Gly Tyr Ser Ala Ala Trp Thr Val Pro Phe Gly
385                 390                 395                 400

Gly Arg Ala Tyr Ile Glu Met Met Gln Cys Asp Asp Ser Asp Glu Pro
                405                 410                 415

Val Val Arg Val Leu Val Asn Asp Arg Val Val Pro Leu His Gly Cys
                420                 425                 430

Glu Val Asp Ser Leu Gly Arg Cys Lys Arg Asp Asp Phe Val Arg Gly
                435                 440                 445

Leu Ser Phe Ala Arg Gln Gly Gly Asn Trp Glu Gly Cys Tyr Ala Ala
            450                 455                 460

Ser Glu
465

(2) INFORMATION FOR SEQ ID NO: 32:
```

(i) SEQUENCE CHARACTERISTICS:
        (A) LENGTH: 1571 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: join(43..89, 147..1494)

(ix) FEATURE:
        (A) NAME/KEY: intron
        (B) LOCATION: 90..146

(ix) FEATURE:
        (A) NAME/KEY: misc_feature
        (B) LOCATION: 894..999
        (D) OTHER INFORMATION: /note= "Position of PCR fragment"

(xi) SEQUENCE DESCRIPTION: SEQ ID NO: 32:

```
AGATTCAACG ACGGAGGAAT CGCAACCCTA ATTGTCGGTA TC ATG GTG ACT CTG         54
                                              Met Val Thr Leu
                                                1

ACT TTC CTG CTT TCG GCG GCG TAT CTG CTT TCT  GG  GTGAGTGGCT            99
Thr Phe Leu Leu Ser Ala Ala Tyr Leu Leu Ser  Gly
 5               10                  15

TGGATCTATT GCTCGGATAG GGCTGTGGTG CTGATTCTGA AACGGAG T AGA GTG         153
                                                      Arg Val

TCT GCG GCA CCT AGT TCT GCT GGC TCC AAG TCC TGC GAT ACG GTA GAC       201
Ser Ala Ala Pro Ser Ser Ala Gly Ser Lys Ser Cys Asp Thr Val Asp
         20                  25                  30

CTC GGG TAC CAG TGC TCC CCT GCG ACT TCT CAT CTA TGG GGC CAG TAC       249
Leu Gly Tyr Gln Cys Ser Pro Ala Thr Ser His Leu Trp Gly Gln Tyr
 35                  40                  45                  50

TCG CCA TTC TTT TCG CTC GAG GAC GAG CTG TCC GTG TCG AGT AAG CTT       297
Ser Pro Phe Phe Ser Leu Glu Asp Glu Leu Ser Val Ser Ser Lys Leu
                 55                  60                  65

CCC AAG GAT TGC CGG ATC ACC TTG GTA CAG GTG CTA TCG CGC CAT GGA       345
Pro Lys Asp Cys Arg Ile Thr Leu Val Gln Val Leu Ser Arg His Gly
             70                  75                  80

GCG CGG TAC CCA ACC AGC TCC AAG AGC AAA AAG TAT AAG AAG CTT GTG       393
Ala Arg Tyr Pro Thr Ser Ser Lys Ser Lys Lys Tyr Lys Lys Leu Val
         85                  90                  95

ACG GCG ATC CAG GCC AAT GCC ACC GAC TTC AAG GGC AAG TTT GCC TTT       441
Thr Ala Ile Gln Ala Asn Ala Thr Asp Phe Lys Gly Lys Phe Ala Phe
     100                 105                 110

TTG AAG ACG TAC AAC TAT ACT CTG GGT GCG GAT GAC CTC ACT CCC TTT       489
Leu Lys Thr Tyr Asn Tyr Thr Leu Gly Ala Asp Asp Leu Thr Pro Phe
115                 120                 125                 130

GGG GAG CAG CAG CTG GTG AAC TCG GGC ATC AAG TTC TAC CAG AGG TAC       537
Gly Glu Gln Gln Leu Val Asn Ser Gly Ile Lys Phe Tyr Gln Arg Tyr
                135                 140                 145

AAG GCT CTG GCG CGC AGT GTG GTG CCG TTT ATT CGC GCC TCA GGC TCG       585
Lys Ala Leu Ala Arg Ser Val Val Pro Phe Ile Arg Ala Ser Gly Ser
                    150                 155                 160

GAC CGG GTT ATT GCT TCG GGA GAG AAG TTC ATC GAG GGG TTC CAG CAG       633
Asp Arg Val Ile Ala Ser Gly Glu Lys Phe Ile Glu Gly Phe Gln Gln
                165                 170                 175
```

```
GCG AAG CTG GCT GAT CCT GGC GCG ACG AAC CGC GCC GCT CCG GCG ATT      681
Ala Lys Leu Ala Asp Pro Gly Ala Thr Asn Arg Ala Ala Pro Ala Ile
    180                 185                 190

AGT GTG ATT ATT CCG GAG AGC GAG ACG TTC AAC AAT ACG CTG GAC CAC      729
Ser Val Ile Ile Pro Glu Ser Glu Thr Phe Asn Asn Thr Leu Asp His
195                 200                 205                 210

GGT GTG TGC ACG AAG TTT GAG GCG AGT CAG CTG GGA GAT GAG GTT GCG      777
Gly Val Cys Thr Lys Phe Glu Ala Ser Gln Leu Gly Asp Glu Val Ala
                215                 220                 225

GCC AAT TTC ACT GCG CTC TTT GCA CCC GAC ATC CGA GCT CGC GCC GAG      825
Ala Asn Phe Thr Ala Leu Phe Ala Pro Asp Ile Arg Ala Arg Ala Glu
            230                 235                 240

AAG CAT CTT CCT GGC GTG ACG CTG ACA GAC GAG GAC GTT GTC AGT CTA      873
Lys His Leu Pro Gly Val Thr Leu Thr Asp Glu Asp Val Val Ser Leu
        245                 250                 255

ATG GAC ATG TGT TCG TTT GAT ACG GTA GCG CGC ACC AGC GAC GCA AGT      921
Met Asp Met Cys Ser Phe Asp Thr Val Ala Arg Thr Ser Asp Ala Ser
    260                 265                 270

CAG CTG TCA CCG TTC TGT CAA CTC TTC ACT CAC AAT GAG TGG AAG AAG      969
Gln Leu Ser Pro Phe Cys Gln Leu Phe Thr His Asn Glu Trp Lys Lys
275                 280                 285                 290

TAC AAC TAC CTT CAG TCC TTG GGC AAG TAC TAC GGC TAC GGC GCA GGC     1017
Tyr Asn Tyr Leu Gln Ser Leu Gly Lys Tyr Tyr Gly Tyr Gly Ala Gly
                295                 300                 305

AAC CCT CTG GGA CCG GCT CAG GGG ATA GGG TTC ACC AAC GAG CTG ATT     1065
Asn Pro Leu Gly Pro Ala Gln Gly Ile Gly Phe Thr Asn Glu Leu Ile
            310                 315                 320

GCC CGG TTG ACT CGT TCG CCA GTG CAG GAC CAC ACC AGC ACT AAC TCG     1113
Ala Arg Leu Thr Arg Ser Pro Val Gln Asp His Thr Ser Thr Asn Ser
        325                 330                 335

ACT CTA GTC TCC AAC CCG GCC ACC TTC CCG TTG AAC GCT ACC ATG TAC     1161
Thr Leu Val Ser Asn Pro Ala Thr Phe Pro Leu Asn Ala Thr Met Tyr
    340                 345                 350

GTC GAC TTT TCA CAC GAC AAC AGC ATG GTT TCC ATC TTC TTT GCA TTG     1209
Val Asp Phe Ser His Asp Asn Ser Met Val Ser Ile Phe Phe Ala Leu
355                 360                 365                 370

GGC CTG TAC AAC GGC ACT GAA CCC TTG TCC CGG ACC TCG GTG GAA AGC     1257
Gly Leu Tyr Asn Gly Thr Glu Pro Leu Ser Arg Thr Ser Val Glu Ser
                375                 380                 385

GCC AAG GAA TTG GAT GGG TAT TCT GCA TCC TGG GTG GTG CCT TTC GGC     1305
Ala Lys Glu Leu Asp Gly Tyr Ser Ala Ser Trp Val Val Pro Phe Gly
            390                 395                 400

GCG CGA GCC TAC TTC GAG ACG ATG CAA TGC AAG TCG GAA AAG GAG CCT     1353
Ala Arg Ala Tyr Phe Glu Thr Met Gln Cys Lys Ser Glu Lys Glu Pro
        405                 410                 415

CTT GTT CGC GCT TTG ATT AAT GAC CGG GTT GTG CCA CTG CAT GGC TGC     1401
Leu Val Arg Ala Leu Ile Asn Asp Arg Val Val Pro Leu His Gly Cys
    420                 425                 430

GAT GTG GAC AAG CTG GGG CGA TGC AAG CTG AAT GAC TTT GTC AAG GGA     1449
Asp Val Asp Lys Leu Gly Arg Cys Lys Leu Asn Asp Phe Val Lys Gly
435                 440                 445                 450

TTG AGT TGG GCC AGA TCT GGG GGC AAC TGG GGA GAG TGC TTT AGT         1494
Leu Ser Trp Ala Arg Ser Gly Gly Asn Trp Gly Glu Cys Phe Ser
                455                 460                 465

TGAGATGTCA TTGTTATGCT ATACTCCAAT AGACCGTTGC TTAGCCATTC ACTTCACTTT   1554

GCTCGAACCG CCTGCCG                                                  1571

(2) INFORMATION FOR SEQ ID NO: 33:
```

```
    (i) SEQUENCE CHARACTERISTICS:
        (A) LENGTH: 465 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 104
        (D) OTHER INFORMATION: /note="potential N-glycosylation site"

(ix) FEATURE:
        (A) NAME/KEY: misc_feature
        (B) LOCATION: 119
        (D) OTHER INFORMATION: /note="potential N-glycosylation site"

(ix) FEATURE:
        (A) NAME/KEY: misc_feature
        (B) LOCATION: 205
        (D) OTHER INFORMATION: /note="potential N-glycosylation site"

(ix) FEATURE:
        (A) NAME/KEY: misc_feature
        (B) LOCATION: 228
        (D) OTHER INFORMATION: /note="potential N-glycosylation site"

(ix) FEATURE:
        (A) NAME/KEY: misc_feature
        (B) LOCATION: 337
        (D) OTHER INFORMATION: /note="potential N-glycosylation site"

(ix) FEATURE:
        (A) NAME/KEY: misc_feature
        (B) LOCATION: 374
        (D) OTHER INFORMATION: /note="potential N-glycosylation site"

(xi) SEQUENCE DESCRIPTION: SEQ ID NO: 33:

Met Val Thr Leu Thr Phe Leu Leu Ser Ala Ala Tyr Leu Leu Ser Gly
 1               5                  10                  15

Arg Val Ser Ala Ala Pro Ser Ala Gly Ser Lys Ser Cys Asp Thr
            20                  25                  30

Val Asp Leu Gly Tyr Gln Cys Ser Pro Ala Thr Ser His Leu Trp Gly
            35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
```

```
                210                 215                 220
Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
                260                 265                 270

Ala Ser Gln Leu Ser Pro Phe Cys Gln Leu Phe Thr His Asn Glu Trp
                275                 280                 285

Lys Lys Tyr Asn Tyr Leu Gln Ser Leu Gly Lys Tyr Tyr Gly Tyr Gly
290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
                340                 345                 350

Met Tyr Val Asp Phe Ser His Asp Asn Ser Met Val Ser Ile Phe Phe
                355                 360                 365

Ala Leu Gly Leu Tyr Asn Gly Thr Glu Pro Leu Ser Arg Thr Ser Val
370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
                420                 425                 430

Gly Cys Asp Val Asp Lys Leu Gly Arg Cys Lys Leu Asn Asp Phe Val
                435                 440                 445

Lys Gly Leu Ser Trp Ala Arg Ser Gly Gly Asn Trp Gly Glu Cys Phe
                450                 455                 460

Ser
465

(2) INFORMATION FOR SEQ ID NO: 34:

(i) SEQUENCE CHARACTERISTICS:
        (A) LENGTH: 1567 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: join(78..124, 177..1527)

(ix) FEATURE:
        (A) NAME/KEY: intron
        (B) LOCATION: 125..176

(ix) FEATURE:
        (A) NAME/KEY: misc_feature
        (B) LOCATION: 930..1035
        (D) OTHER INFORMATION: /note= "Position of PCR fragment"

(ix) FEATURE:
```

(A) NAME/KEY: misc_feature
        (B) LOCATION: 1215..1394
        (D) OTHER INFORMATION: /note= "Position of PCR fragment"

(xi) SEQUENCE DESCRIPTION: SEQ ID NO: 34:

```
ACGTCCCAGG TCGGGACTA CATCCGCTAT GTGGTCCTCT ACTTCGTCGG AAGAATATAC        60

TGTCTCTTGT GGCTACC ATG GGG GTT TTC GTC GTT CTA TTA TCT ATC GCG        110
                   Met Gly Val Phe Val Val Leu Leu Ser Ile Ala
                    1               5                      10

ACT CTG TTC GGC  AG  GTATGTGCAC CGCTCTAGGT TCAACTCGCC TGGTAACTGA       164
Thr Leu Phe Gly Ser
             15

CAAACAGCAC AG C ACA TCG GGC ACT GCG CTG GGC CCC CGT GGA AAT CAC        213
               Thr Ser Gly Thr Ala Leu Gly Pro Arg Gly Asn His
                        20                      25

AGC GAC TGC ACC TCA GTC GAC CGG GGG TAT CAA TGC TTC CCT GAG CTC        261
Ser Asp Cys Thr Ser Val Asp Arg Gly Tyr Gln Cys Phe Pro Glu Leu
 30              35                      40

TCC CAT AAA TGG GGT CTC TAC GCG CCC TAT TTC TCC CTC CAG GAT GAA        309
Ser His Lys Trp Gly Leu Tyr Ala Pro Tyr Phe Ser Leu Gln Asp Glu
 45              50                      55                  60

TCT CCG TTT CCT CTG GAC GTC CCG GAT GAC TGC CAC ATC ACC TTT GTG        357
Ser Pro Phe Pro Leu Asp Val Pro Asp Asp Cys His Ile Thr Phe Val
                 65                  70                  75

CAG GTG CTG GCC CGA CAT GGA GCG CGG TCT CCA ACC GAT AGC AAG ACA        405
Gln Val Leu Ala Arg His Gly Ala Arg Ser Pro Thr Asp Ser Lys Thr
                 80                  85                  90

AAG GCG TAT GCC GCG ACT ATT GCA GCC ATC CAG AAG AAT GCC ACC GCG        453
Lys Ala Tyr Ala Ala Thr Ile Ala Ala Ile Gln Lys Asn Ala Thr Ala
             95                  100                 105

TTG CCG GGC AAA TAC GCC TTC CTG AAG TCG TAC AAT TAC TCC ATG GGC        501
Leu Pro Gly Lys Tyr Ala Phe Leu Lys Ser Tyr Asn Tyr Ser Met Gly
        110                 115                 120

TCC GAG AAC CTG AAC CCC TTC GGG CGG AAC CAA CTG CAA GAT CTG GGC        549
Ser Glu Asn Leu Asn Pro Phe Gly Arg Asn Gln Leu Gln Asp Leu Gly
125                 130                 135                 140

GCC CAG TTC TAC CGT CGC TAC GAC ACC CTC ACC CGG CAC ATC AAC CCT        597
Ala Gln Phe Tyr Arg Arg Tyr Asp Thr Leu Thr Arg His Ile Asn Pro
                145                 150                 155

TTC GTC CGG GCC GCG GAT TCC TCC CGC GTC CAC GAA TCA GCC GAG AAG        645
Phe Val Arg Ala Ala Asp Ser Ser Arg Val His Glu Ser Ala Glu Lys
            160                 165                 170

TTC GTC GAG GGC TTC CAA AAC GCC CGC CAA GGC GAT CCT CAC GCC AAC        693
Phe Val Glu Gly Phe Gln Asn Ala Arg Gln Gly Asp Pro His Ala Asn
        175                 180                 185

CCT CAC CAG CCG TCG CCG CGC GTG GAT GTA GTC ATC CCC GAA GGC ACC        741
Pro His Gln Pro Ser Pro Arg Val Asp Val Val Ile Pro Glu Gly Thr
    190                 195                 200

GCC TAC AAC AAC ACG CTC GAG CAC AGC ATC TGC ACC GCC TTC GAG GCC        789
Ala Tyr Asn Asn Thr Leu Glu His Ser Ile Cys Thr Ala Phe Glu Ala
205                 210                 215                 220

AGC ACC GTC GGC GAC GCC GCG GCA GAC AAC TTC ACT GCC GTG TTC GCG        837
Ser Thr Val Gly Asp Ala Ala Ala Asp Asn Phe Thr Ala Val Phe Ala
                225                 230                 235

CCG GCG ATC GCC AAG CGT CTG GAG GCC GAT CTG CCC GGC GTG CAG CTG        885
Pro Ala Ile Ala Lys Arg Leu Glu Ala Asp Leu Pro Gly Val Gln Leu
            240                 245                 250

TCC GCC GAC GAC GTG GTC AAT CTG ATG GCC ATG TGT CCG TTC GAG ACG        933
Ser Ala Asp Asp Val Val Asn Leu Met Ala Met Cys Pro Phe Glu Thr
        255                 260                 265
```

```
GTC AGC CTG ACC GAC GAC GCG CAC ACG CTG TCG CCG TTC TGC GAC CTC      981
Val Ser Leu Thr Asp Asp Ala His Thr Leu Ser Pro Phe Cys Asp Leu
    270                 275                 280

TTC ACC GCC GCC GAG TGG ACG CAG TAC AAC TAC CTG CTC TCG CTG GAC     1029
Phe Thr Ala Ala Glu Trp Thr Gln Tyr Asn Tyr Leu Leu Ser Leu Asp
285                 290                 295                 300

AAG TAC TAC GGC TAC GGC GGC GGC AAT CCG CTG GGC CCC GTG CAG GGC     1077
Lys Tyr Tyr Gly Tyr Gly Gly Gly Asn Pro Leu Gly Pro Val Gln Gly
                305                 310                 315

GTG GGC TGG GCG AAC GAG CTG ATC GCG CGG CTG ACG CGC TCC CCC GTC     1125
Val Gly Trp Ala Asn Glu Leu Ile Ala Arg Leu Thr Arg Ser Pro Val
            320                 325                 330

CAC GAC CAC ACC TGC GTC AAC AAC ACC CTC GAC GCC AAC CCG GCC ACC     1173
His Asp His Thr Cys Val Asn Asn Thr Leu Asp Ala Asn Pro Ala Thr
        335                 340                 345

TTC CCG CTG AAC GCC ACC CTC TAC GCG GAC TTT TCG CAC GAC AGT AAC     1221
Phe Pro Leu Asn Ala Thr Leu Tyr Ala Asp Phe Ser His Asp Ser Asn
350                 355                 360

CTG GTG TCG ATC TTC TGG GCG CTG GGT CTG TAC AAC GGC ACC AAG CCC     1269
Leu Val Ser Ile Phe Trp Ala Leu Gly Leu Tyr Asn Gly Thr Lys Pro
365                 370                 375                 380

CTG TCG CAG ACC ACC GTG GAG GAT ATC ACC CGG ACG GAC GGG TAC GCG     1317
Leu Ser Gln Thr Thr Val Glu Asp Ile Thr Arg Thr Asp Gly Tyr Ala
                385                 390                 395

GCC GCC TGG ACG GTG CCG TTT GCC GCC CGC GCC TAC ATC GAG ATG ATG     1365
Ala Ala Trp Thr Val Pro Phe Ala Ala Arg Ala Tyr Ile Glu Met Met
            400                 405                 410

CAG TGT CGC GCG GAG AAG CAG CCG CTG GTG CGC GTG CTG GTC AAC GAC     1413
Gln Cys Arg Ala Glu Lys Gln Pro Leu Val Arg Val Leu Val Asn Asp
        415                 420                 425

CGT GTC ATG CCG CTG CAC GGC TGC GCG GTG GAT AAT CTG GGC AGG TGT     1461
Arg Val Met Pro Leu His Gly Cys Ala Val Asp Asn Leu Gly Arg Cys
    430                 435                 440

AAA CGG GAC GAC TTT GTG GAG GGA CTG AGC TTT GCG CGG GCA GGA GGG     1509
Lys Arg Asp Asp Phe Val Glu Gly Leu Ser Phe Ala Arg Ala Gly Gly
445                 450                 455                 460

AAC TGG GCC GAG TGT TTC TGATGTACAT GCTGTAGTTA GCTTTGAGTC            1557
Asn Trp Ala Glu Cys Phe
                465

CTGAGGTACC                                                          1567

(2) INFORMATION FOR SEQ ID NO: 35:

(i) SEQUENCE CHARACTERISTICS:
        (A) LENGTH: 466 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 27
        (D) OTHER INFORMATION: /note="potential N-glycosylation site"

(ix) FEATURE:
        (A) NAME/KEY: misc_feature
        (B) LOCATION: 120
        (D) OTHER INFORMATION: /note="potential N-glycosylation site"

(ix) FEATURE:
        (A) NAME/KEY: misc_feature
        (B) LOCATION: 207
        (D) OTHER INFORMATION: /note="potential N-glycosylation site"
```

```
    (ix) FEATURE:
         (A) NAME/KEY: misc_feature
         (B) LOCATION: 230
         (D) OTHER INFORMATION: /note="potential N-glycosylation site"

(ix) FEATURE:
         (A) NAME/KEY: misc_feature
         (B) LOCATION: 352
         (D) OTHER INFORMATION: /note="potential N-glycosylation site"

(ix) FEATURE:
         (A) NAME/KEY: misc_feature
         (B) LOCATION: 376
         (D) OTHER INFORMATION: /note="potential N-glycosylation site"

(xi) SEQUENCE DESCRIPTION: SEQ ID NO: 35:

Met Gly Val Phe Val Leu Leu Ser Ile Ala Thr Leu Phe Gly Ser
 1               5                  10                  15

Thr Ser Gly Thr Ala Leu Gly Pro Arg Gly Asn His Ser Asp Cys Thr
            20                  25                  30

Ser Val Asp Arg Gly Tyr Gln Cys Phe Pro Glu Leu Ser His Lys Trp
        35                  40                  45

Gly Leu Tyr Ala Pro Tyr Phe Ser Leu Gln Asp Glu Ser Pro Phe Pro
    50                  55                  60

Leu Asp Val Pro Asp Asp Cys His Ile Thr Phe Val Gln Val Leu Ala
65                  70                  75                  80

Arg His Gly Ala Arg Ser Pro Thr Asp Ser Lys Thr Lys Ala Tyr Ala
                85                  90                  95

Ala Thr Ile Ala Ala Ile Gln Lys Asn Ala Thr Ala Leu Pro Gly Lys
            100                 105                 110

Tyr Ala Phe Leu Lys Ser Tyr Asn Tyr Ser Met Gly Ser Glu Asn Leu
        115                 120                 125

Asn Pro Phe Gly Arg Asn Gln Leu Gln Asp Leu Gly Ala Gln Phe Tyr
    130                 135                 140

Arg Arg Tyr Asp Thr Leu Thr Arg His Ile Asn Pro Phe Val Arg Ala
145                 150                 155                 160

Ala Asp Ser Ser Arg Val His Glu Ser Ala Glu Lys Phe Val Glu Gly
                165                 170                 175

Phe Gln Asn Ala Arg Gln Gly Asp Pro His Ala Asn Pro His Gln Pro
            180                 185                 190

Ser Pro Arg Val Asp Val Ile Pro Glu Gly Thr Ala Tyr Asn Asn
        195                 200                 205

Thr Leu Glu His Ser Ile Cys Thr Ala Phe Glu Ala Ser Thr Val Gly
    210                 215                 220

Asp Ala Ala Asp Asn Phe Thr Ala Val Phe Ala Pro Ala Ile Ala
225                 230                 235                 240

Lys Arg Leu Glu Ala Asp Leu Pro Gly Val Gln Leu Ser Ala Asp Asp
                245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Ala
        275                 280                 285

Glu Trp Thr Gln Tyr Asn Tyr Leu Leu Ser Leu Asp Lys Tyr Tyr Gly
    290                 295                 300

Tyr Gly Gly Asn Pro Leu Gly Pro Val Gln Gly Val Gly Trp Ala
305                 310                 315                 320

Asn Glu Leu Ile Ala Arg Leu Thr Arg Ser Pro Val His Asp His Thr
```

-continued

```
                        325                 330                 335
Cys Val Asn Asn Thr Leu Asp Ala Asn Pro Ala Thr Phe Pro Leu Asn
                340                 345                 350
Ala Thr Leu Tyr Ala Asp Phe Ser His Asp Ser Asn Leu Val Ser Ile
            355                 360                 365
Phe Trp Ala Leu Gly Leu Tyr Asn Gly Thr Lys Pro Leu Ser Gln Thr
        370                 375                 380
Thr Val Glu Asp Ile Thr Arg Thr Asp Gly Tyr Ala Ala Ala Trp Thr
385                 390                 395                 400
Val Pro Phe Ala Ala Arg Ala Tyr Ile Glu Met Met Gln Cys Arg Ala
                405                 410                 415
Glu Lys Gln Pro Leu Val Arg Val Leu Val Asn Asp Arg Val Met Pro
                420                 425                 430
Leu His Gly Cys Ala Val Asp Asn Leu Gly Arg Cys Lys Arg Asp Asp
            435                 440                 445
Phe Val Glu Gly Leu Ser Phe Ala Arg Ala Gly Gly Asn Trp Ala Glu
    450                 455                 460
Cys Phe
465
```

HEAT TOLERANT PHYTASES

CROSS REFERENCE TO RELATED APPLICATION

This application is a continuation of U.S. application Ser. No. 08/868,435 filed Jun. 3, 1997, now U.S. Pat. No. 6,291,221, which is a divisional of U.S. application Ser. No. 08/744,231 filed Nov. 5, 1996, now U.S. Pat. No. 6,358,722, which is a contiuation-in-part of U.S. application Ser. No. 08/424,757 filed Apr. 18, 1995 now abandoned.

BACKGROUND OF THE INVENTION

Phosphorus is an essential element for the growth of all organisms. In livestock production, feed must be supplemented with inorganic phosphorus in order to obtain a good growth is performance of monogastric animals (for example, pigs, poultry and fish).

In contrast, no inorganic phosphate needs to be added to the feedstuffs of ruminant animals. Microorganisms, present in the rumen, produce enzymes which analyze the conversion of phytate (myo-inositolhexakis-phosphate) to inositol and inorganic phosphate.

Phytate occurs as a storage phosphorus source in virtually all feed substances originating from plants. Phytate comprises 1–3% of all nuts, cereals, legumes, oil seeds, spores and pollen. Complex salts of phytic acid are termed phytin. Phytic acid is considered to be an anti-nutritional factor since it chelates minerals such as calcium, zinc, magnesium, iron and may also react with proteins, thereby decreasing the bioavailability of protein and nutritionally important minerals.

Phytate phosphorous passes through the gastro-intestinal tract of monogastric animals and is excreted in the manure. Though some hydrolysis of phytate does occur in the colon, the thus-released inorganic phosphorus has no nutritional value since inorganic phosphorus is absorbed only in the small intestine. As a consequence, a significant amount of the nutritionally important phosphorus is not used by monogastric animals, despite its presence in the feed.

The excretion of phytate phosphorus in manure has further consequences. Intensive livestock production has increased enormously during the past decades. Consequently, the amount of manure produced has increased correspondingly and has caused environmental problems in various parts of the world. This is due, in part, to the accumulation of phosphate from manure in surface waters which has caused eutrophication. For other background information, see European Patent Application Publication No. 420 358.

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A phytase was first described in rice bran in 1907 [Suzuki et al., Bull. Coll. Agr. Tokyo Imp. Univ. 7, 495 (1907)] and phytases from Aspergillus species in 1911 [Dox and Golden, J. Biol. Chem. 10, 183–186 (1911)]. Phytases have also been found in wheat bran, plant seeds, animal intestines and in microorganisms [Howsen and Davis, Enzyme Microb. Technol. 5, 377–382 (1983), Lambrechts et al., Biotech. Lett. 14, 61–66 (1992), Shieh and Ware, Appl. Microbiol. 16, 1348–1351 (1968)].

The cloning and expression of the phytase from *Aspergillus niger* (ficuum) has been described by Van Hartingsveldt et al., in Gene, 127, 87–94 (1993) and in European Patent Application, Publication No. 420 358 and from *Aspergillus niger* var awamori by Piddington et al. in Gene 133, 55–62 (1993).

Since phytases used so far in agriculture have certain disadvantages, it is an object of the present invention to provide new phytases or polypeptides having phytase activity with improved properties. Since it is known that phytases used so far lose activity during feed pelleting process due to heat treatment, improved heat tolerance would be such an improved property.

So far, phytases have not been reported in thermotolerant fungus with the exception of *Aspergillus fumigatus* [Dox and Golden et al., J. Biol. Chem. 10, 183–186 (1911)] and *Rhizopus oryzae* [Howson and Davies, Enzyme Microb. Technol. 5, 377–382 (1993)]. Thermotolerant phytases have been described originating from *Aspergillus terreus* Strain 9A-1 [Temperature optimum 70° C.; Yamada et al., Agr. Biol. Chem. 32, 1275–1282 (1968)] and *Schwanniomyces castellii* [Temperature optimum 77° C.; Segueilha et al., Bioeng. 74, 7–11 (1992)]. However for commercial use in agriculture such phytases must be available in large quantities. Accordingly it is an object of the present invention to provide DNA sequences coding for heat tolerant phytases. Improved heat tolerance of phytases encoded by such DNA sequences can be determined by assays known in the art, for example, by the processes used for feed pelleting or assays determining the heat dependence of the enzymatic activity itself as described, for example, by Yamada et al. (s.a.).

It is furthermore an object of the present invention to screen fungi which show a certain degree of thermotolerance for phytase production. Such screening can be made as described, for example, in Example 1. In this way heat tolerant fungal strains, listed in Example 1, have been identified for the first time to produce a phytase.

Heat tolerant fungal strains, see for example, those listed in Example 1, can then be grown as known in the art, for example, as indicated by their supplier, for example, the American Tissue Type Culture Collection (ATCC), Deutsche Sammlung von Mikroorganismen und Zellkulturen GmbH (DSM), Agricultural Research Service Culture Collection (NRRL) and the Centralbureau voor Schimmelcultures (CBS) from which such strains are available or as indicated, for example, in Example 2.

Further improved properties are, for example, an improved substrate specificity regarding phytic acid [myo-inositol(1,2,3,4,5,6)hexakisphosphate] which is a major storage form of phosphorous in plants and seeds. Since for the complete release of the six phosphate groups from phytic acid, a phytase and a pH 2.5. acid phosphatase activity are required, a polypeptide having phytase and pH 2.5 acid phosphatase activity would be highly desirable. For example, International Patent Application Publication No. 94/03072 discloses an expression system which allows the expression of a mixture of phytate degrading enzymes in desired ratios. However, it would be even more desirable to have both such activities in a single polypeptide. Therefore it is also an object of the present invention to provide DNA sequences coding for such polypeptides. Phytase and phosphatase activities can be determined by assays known in the state of the art or described, for example, in Example 9.

Another improved property is, for example, a so called improved pH-profile. This means, for example, two phytin degrading activity maxima, for example, one at around pH 2.5 which could be the pH in the stomach of certain animals and another at around pH 5.5 which could be the pH after the stomach in certain animals. Such pH profile can be determined by assays known in the state of the art or described, for example, in Example 9. Accordingly it is also an object of the present invention to provide DNA sequences coding for such improved polypeptides.

It is yet another object of the present invention to provide a DNA sequence coding for a polypeptide having phytase activity and which DNA sequence is derived from a fungus selected from the group consisting of *Acrophialophora levis, Aspergillus terreus, Aspergillus fumigatus, Aspergillus nidulans, Aspergillus sojae, Calcarisporiella thermophila, Chaetomium rectopilium, Corynascus thermophilus*, Humicola sp., *Mycelia sterilia, Myrococcum thermophilum, Myceliophthora thermophila, Rhizomucor miehei, Sporotrichum cellulophilum, Sporotrichum thermophile, Scytalidium indonesicum* and *Talaromyces thermophilus* or a DNA sequence coding for a fragment of such a polypeptide which fragment still has phytase activity, or more specifically such a DNA sequence wherein the fungus is selected from the group consisting of *Acrophialophora levis, Aspergillus fumigatus, Aspergillus nidulans, Aspergillus terreus, Calcarisporiella thermophila, Chaetomium rectopilium, Corynascus thermophilus, Sporotrichum cellulophilum, Sporotrichum thermophile, Mycelia sterilia, Myceliophthora thermophila* and *Talaromyces thermophilus*, or more specifically such a DNA sequence wherein the fungus is selected from the group consisting of *Aspergillus terreus, Myceliophthora thermophila, Aspergillus fumigatus, Aspergillus nidulans* and *Talaromyces thermophilus*. DNA sequences coding for a fragment of a polypeptide of the present invention can, for example, be between 1350 and 900, preferably between 900 and 450 and most preferably between 450 and 150 nucleotides long and can be prepared on the basis of the DNA sequence of the complete polypeptide by recombinant methods or by chemical synthesis with which one skilled in the art is familiar with.

Furthermore it is an object of the present invention to provide a DNA sequence which codes for a polypeptide having phytase activity and which DNA sequence is selected from the following:

(a) the DNA sequence of FIG. 1 [SEQ ID NO:1] or its complementary strand;

(b) a DNA sequence which hybridizes under standard conditions with sequences defined under (a) or preferably with the coding region of such sequences or more preferably with a region between positions 491 to 1856 of such DNA sequences or even more preferably with a genomic probe obtained by preferably random priming using DNA of Aspergillus terreus 9A1 as described in Example 12.

(c) a DNA sequence which, because of the degeneracy of the genetic code, does not hybridize with sequences of (a) or (b), but which codes For polypeptides having exactly the same amino acid sequences as the polypeptides encoded by these DNA sequences; and (d) a DNA sequence which is a fragment of the DNA sequences specified in (a), (b) or (c).

"Standard conditions" for hybridization mean in this context the conditions which are generally used by one skilled in the art to detect specific hybridization signals and which are described, for example, by Sambrook et al., "Molecular Cloning" second edition, Cold Spring Harbor Laboratory Press 1989, New York, or preferably so called stringent hybridization and non-stringent washing conditions or more preferably so called stringent hybridization and stringent washing conditions one skilled in the art is familiar with and which are described, for example, in Sambrook et al. (s.a.) or even more preferred the stringent hybridization and non-stringent or stringent washing conditions as given in Example 12. "Fragment of the DNA sequences" means in this context a fragment which codes for a polypeptide still having phytase activity as specified above.

It is also an object of the present invention to provide a DNA sequence which codes for a polypeptide having phytase activity and which DNA sequence is selected from the following:

(a) the DNA sequence of FIG. 2 [SEQ ID NO:3] or its complementary strand;

(b) a DNA sequence which hybridizes under standard conditions with sequences defined under (a) or preferably a region which extends to about at least 80% of the coding region optionally comprising about between 100 to 150 nucleotides of the 5' end of the non-coding region of such DNA sequences or more preferably with a region between positions 2068 to 3478 of such DNA sequences or even more preferably with a genomic probe obtained by preferably random priming using DNA of Myceliophthora thermophila as described in Example 12.

(c) a DNA sequence which, because of the degeneracy of the genetic code, does not hybrida&e with sequences of (a) or (b), but which codes for polypeptides having exactly the same amino acid sequences as the polypeptides encoded by these DNA sequences; and (d) a DNA sequence which is a fragment of the DNA sequences specified in (a), (b) or (c).

"Fragments" and "standard conditions" have the meaning as given above.

It is also an object of the present invention to provide a DNA sequence which codes for a polypeptide having phytase activity and which DNA sequence is selected from the following:

(a) a DNA sequence comprising one of the DNA sequences of FIGS. 4 [SEQ ID NO:5], 5 [SEQ ID NO:7], 6 [SEQ ID NO:9] or 10A and B ["aterr21", SEQ ID NO:13; "aterr58": SEQ ID NO:14] or its complementary strand;

(b) a DNA sequence which hybridizes under standard conditions with sequences defined under (a) or preferably with such sequences comprising the DNA sequence of FIG. 4 [SEQ ID NO:5] isolatable from *Talaromyces thermophilus*, or of FIG. 5 [SEQ ID NO:7] isolatable from *Aspergillus fumigatus*, or of FIG. 6 [SEQ ID NO:9] isolatable from *Aspergillus nidulans* or of one or both of the sequences given in FIGS. 10A and B ["aterr21", SEQ ID NO:13; "aterr58": SEQ ID NO:14] isolatable from *Aspergillus terreus* (CBS 116.46) or more preferably with a region of such DNA sequences spanning at least 80% of the coding region or most preferably with a genomic probe obtained by random priming using DNA of *Talaromyces thermophilus* or *Aspergillus fumigatus* or *Aspergillus nidulans* or *Aspergillus terreus* (CBS 116.46) as described in Example 12;

(c) a DNA sequence which, because of the degeneracy of the genetic code, does not hybridize with sequences of (a) or (b) but which codes for polypeptides having exactly the same amino acid sequences as the polypeptides encoded by these DNA sequences; and (d) a DNA sequence which is a fragment of the DNA sequences specified in (a), (b) or (c).

It is furthermore an object of the present invention to provide a DNA sequence which codes for a polypeptide having phytase activity and which DNA sequence is selected from a DNA sequence comprising the DNA sequence of FIG. 4 [SEQ ID NO:5] isolatable from *Talaromyces thermophilus*, of FIG. 5 [SEQ ID NO:7] isolatable from *Aspergillus fumigatus*, of FIG. 6 [SEQ ID NO:9] isolatable from *Aspergillus nidulans* or of FIGS. 10A and B ["aterr21": SEQ ID NO:13; "aterr58": SEQ ID NO:14] isolatable from *Aspergillus terreus* (CBS 116.46) or which DNA sequence is a degenerate variant or equivalent thereof.

"Fragments" and "standard conditions" have the meaning as given above. "Degenerate variant" means in this context a DNA sequence which because of the degeneracy of the genetic code has a different nucleotide sequence as the one referred to but codes for a polypeptide with the same amino acid sequence. "Equivalent" refers in this context to a DNA sequence which codes for polypeptides having phytase activity with an amino acid sequence which differs by deletion, substitution and/or addition of one or more amino acids, preferably up to 50, more preferably up to 20, even more preferably up to 10 or most preferably 5, 4, 3 or 2, from the amino acid sequence of the polypeptide encoded by the DNA sequence to which the equivalent sequence refers to. Amino acid substitutions which do not generally alter the specific activity are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse (the three letter abbreviations are. used for amino acids and are standard and known in the art).

Such equivalents can be produced by methods known in the state of the art and described, for example, in Sambrook et al. (s.a.). Whether polypeptides encoded by such equivalent sequences still have a phytase activity can be determined by one of the assays known in the art or, for example, described in Example 9.

It is also an object of the present invention to provide one of the aforementioned DNA sequences which code for a polypeptide having phytase activity which DNA sequence is derived from a fungus, or more specifically such a fungus selected from one of the above mentioned specific groups of fungi.

Furthermore it is an object of the present invention to provide a DNA sequence which codes for a polypeptide having phytase activity and which DNA sequence hybridizes under standard conditions with a probe which is a product of a PCR reaction with DNA isolated from a fungus of one of the above mentioned groups of fungi and the following pair of PCR primer:

"ATGGA(C/T)ATGTG(C/T)TC(N)TT(C/T)GA" [SEQ ID NO:15] as sense primer and

"TT(A/G)CC(A/G)GC(A/G)CC(G/A)TG(N)CC(A/G)TA" [SEQ ID NO: 16] as anti-sense primer.

"Standard conditions" have the meaning given above. "Product of a PCR reaction" means preferably a product obtainable or more preferably as obtained by a reaction described in Example 12 referring back to Example 11.

Furthermore it is an object of the present invention to provide a DNA sequence which codes for a polypeptide having phytase activity and which DNA sequence hybridizes under standard conditions with a probe which is a product of a PCR reaction with DNA isolated from Aspergillus terreus (CBS 116.46) and the following two pairs of PCR primers:

(a) "ATGGA(C/T)ATGTG(C/T)TC(N)TT(C/T)GA" [SEQ ID NO:15] as the sense primer and

"TT(A/G)CC(A/G)GC(A/G)CC(G/A)TG(N)CC(A/G)TA" [SEQ ID NO:16] as the anti-sense primer; and (b) "ITA(C/T)GC(N)GA(C/T)TT(C/T)TC(N)CA(C/T)GA-" [SEQ ID NO:17] as the sense primer and "CG(G/A)TC(G/A)TT(N)AC(N)AG(N)AC(N)CO [SEQ ID NO:18] as the anti-sense primer.

"Standard conditions" are as defined above and the term "product of a PCR reaction" means preferably a product obtainable gor more preferably as obtained by a reaction described in Example 11.

It is furthermore an object of the present invention to provide a DNA sequence coding for a chimeric construct having phytase activity which chimeric construct comprises a fragment of a DNA sequence as specified above. The chimeric construct can comprise a fragment of a DNA sequence derived from a fungus. The fragment of a DNA sequence from a fungus can be fused to the fragment of another DNA sequence from another fungus. The N-terminal end of a DNA sequence from a fungus can be fused at its C-terminal end to the fragment of another DNA sequence from different fungus. The fungus from which the fragments can be selected include those from *Acrophialophora levis, Aspergillus terreus, Aspergillus fumigatus, Aspergillus nidulans, Aspergillus sojae, Calcarisporiella thermophila, Chaetomium rectopilium, Corynascus thermophilus*, Humicola sp., *Mycelia sterilia, Myrococcum thermophilum, Myceliophthora thermophila, Rhizomucor miehei, Sporotrichum cellulophilum, Sporotrichum thermophile, Scytalidium indonesicum* and *Talaromyces thermophilus*, preferably selected from the group consisting of *Acrophialophora levis, Aspergillus fumigatus, Aspergillus nidulans, Aspergillus terreus, Calcarisporiella thermophila, Chaetomium rectopilium, Corynascus thermophilus, Sporotrichum cellulophilum, Sporotrichum thermophile, Mycelia sterilia, Myceliophthora thermophila* and *Talaromyces thermophilus*, more preferably selected from the group consisting of *Aspergillus terreus, Myceliophthora thermophila, Aspergillus fumigatus, Aspergillus nidulans* and *Talaromyces thermophilus*, and even more preferably such a DNA sequence wherein the chimeric construct consists at its N-terminal end of a fragment of the *Aspergillus niger* phytase fused at its C-terminal end to a fragment of the *Aspergillus terreus* phytase, or more preferably such a DNA sequence with the specific nucleotide sequence as shown in FIG. 7 [SEQ ID NO:11] and a degenerate variant or equivalent thereof, wherein "degenerate variant" and "equivalent" have the meanings as given above.

It is furthermore an object of the present invention to provide for the partial sequence of a 6 kb HindIII/KpnI insert of clone 1 (see FIG. 13, discussed herein) (SEQ ID NO:28), which includes the complete phytase-encoding gene of *Aspergillus nidulans*, a protein of 463 amino acids (SEQ ID NO:29).

It is furthermore an object of the present invention to provide for the partial sequences of a 5.5 kb EcoRI/SacI insert of clone Tt29-132 (see FIG. 17, discussed herein) (SEQ ID NO:30), which includes the complete phytase-encoding gene of *Talaromyces thermophilus*, a protein of 466 amino acids (SEQ ID NO:31).

It is furthermore an object of the present invention to provide for the partial sequence of a 6 kb BamHI fragment (see FIG. 19 discussed herein) (SEQ ID NO: 32), which included the complete phytase-encoding gene of *Aspergillus fumigatus*, a protein of 465 amino acids (SEQ ID NO:33).

It is furthermore an object of the present invention to provide for the partial sequence of a 2 kb KpnI insert of clone 227 (see FIG. 21 discussed herein) (SEQ ID NO:34), which includes the complete phytase-encoding gene of *Aspergillus terreus* (CBS116.46), a protein of 466 amino acids (SEQ ID NO:35).

Furthermore it is an object of the present invention to provide a DNA sequence as specified above wherein the encoded polypeptide is a phytase.

Furthermore, it is an object of the present invention to provide the polypeptides encoded by the above described DNA sequences which have phytase activity and fragments of the polypeptides which retain phytase activity, and in particular those polypeptides of SEQ ID NO:2, SEQ ID NO:4, SEQ ID NO:6, SEQ ID NO:8, SEQ ID NO:10, SEQ ID NO:12, SEQ ID NO:29, SEQ ID NO:11, SEQ ID NO:33, and SEQ ID NO:35.

Genomic DNA or cDNA from fungal strains can be prepared as known in the art [see for example, Yelton et al., Procd. Natl. Acad. Sci. USA, 1470–1474 (1984) or Sambrook et al., s.a., or other standard reference for preparing CDNA from fungi] or, for example, as specifically described in Example 2.

The cloning of the DNA-sequences of the present invention from such genomic DNA can then be effected, for example, by using the well known polymerase chain reaction (PCR) method. The principles of this method are outlined for example, by White et al. (1989), whereas improved methods are described for example, in Innis et al. [PCR Protocols: A guide to Methods and Applications, Academic Press, Inc. (1990)]. PCR is an in vitro method for producing large amounts of a specific DNA of defined length and sequence from a mixture of different DNA-sequences. Thereby, PCR is based on the enzymatic amplification of the specific DNA fragment of interest which is flanked by two oligonucleotide primers which are specific for this sequence and which hybridize to the opposite strands of the target sequence. The primers are oriented with their 3' ends pointing toward each other. Repeated cycles of heat denaturation of the template, annealing of the primers to their complementary sequences and extension of the annealed primers with a DNA polymerase result in the amplification of the segment between the PCR primers. Since the extension product of each primer can serve as a template for the other, each cycle essentially doubles the amount of the DNA fragment produced in the previous cycle. By utilizing the thermostable Taq DNA polymerase, isolated from the thermophilic bacteria Thermus aquaticus, it has been possible to avoid denaturation of the polymerase which necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition by non-target fragments for enzyme and primers. In this way the specific sequence of interest is highly amplified and can be easily separated from the non-specific sequences by methods known in-the art, for example, by separation on an agarose gel and cloned by methods known in the art using vectors as described for example, by Holten and Graham in Nucleic Acid Res. 19, 1156 (1991), Kovalic et. al. in Nucleic Acid Res. 19, 4560 (1991), Marchuk et al. in Nucleic Acid Res. 19, 1154 (1991) or Mead et al. in Bio/Technology 9, 657–663 (1991).

The oligonucleotide primers used in the PCR procedure can be prepared as known in the art and described for example, in Sambrook et al. (1989 "Molecular cloning" 2nd edt., Cold Spring Harbor Laboratory Press, Cold Spring Harbor).

The specific primers used in the practice of the present invention have been designed as degenerate primers on the basis of DNA-sequence comparisons of known sequences of the *Aspergillus niger* phytase, the *Aspergillus niger* acid phosphatase, the *Saccharomyces cerevisiae* acid phosphatase and the *Schizosaccharomyces pombe* acid phosphatase (for sequence information see, for example, European Bioinformatics Institute (Hinxton Hall, Cambridge, GB). The degeneracy of the primers was reduced by selecting some codons according to a codon usage table of *Aspergillus niger* prepared on the basis of known sequences from *Aspergillus niger*. Furthermore it has been found that the amino acid at the C-terminal end of the amino acid sequences used to define the specific probes should be a conserved amino acid in all acid phosphatases including phytases specified above but the rest of the amino acids should be more phytase than phosphatase specific.

Such amplified DNA-sequences can than be used to screen DNA libraries of DNA of, for example, fungal origin by methods known in the art (Sambrook et al., s.a.) or as specifically described in Examples 5–7.

Once complete DNA-sequences of the present invention have been obtained they can be integrated into vectors by methods known in the art and described for example, in Sambrook et al. (s.a.) to overexpress the encoded polypeptide in appropriate host systems. However, one skilled in the art knows that also the DNA-sequences themselves can be used to transform the suitable host systems of the invention to get overexpression of the encoded polypeptide. Appropriate host systems are for example fungi, like Aspergilli, for example, Aspergillus niger ATCC 91421 or *Aspergillus ficuum* [NRRL 31351 or like Trichoderma, for example, *Trichoderma reesei* or yeasts, like Saccharomyces, for example, *Saccharomyces cerevisiae* or Pichia, like *Pichia pastoris*, all available from ATCC. Bacteria which can be used are for example, *E. coli*, Bacilli as, for example, *Bacillus subtilis* or Streptomyces, for example, *Streptomyces lividans* (see for example, Anné and Mallaert in FEMS Microbiol. Letters 114, 121 (1993). *E. coli*, which could be used are *E. coli* K12 strains for example, M15 [described as DZ 291 by Villarejo et al. in J. Bacteriol. 120, 466–474 (1974)], HB 101 [ATCC No. 33694] or *E. coli* SG13009 (Gottesman et al., J. Bacteriol. 148, 265–273 (1981)].

Vectors which can be used for expression in fungi are known in the art and described for example, in EP 420 358, or by Cullen et al. [Bio/Technology 5, 369–376 (1987)] or Ward in Molecular Industrial Mycology, Systems and Applications for Filamentous Fungi, Marcel Dekker, New York (1991), Upshall et al. [Bio/Technology 5, 1301–1304 (1987)] Gwynne et al. [Bio/Technology 5, 71–79 (1987)], Punt et al. [J. of Biotechnology 17, 19–34 (1991)] and for yeast by Sreekrishna et al. [J. Basic Microbiol. 28, 265–278 (1988), Biochem. 28, 4117–4125 (1989)], Hitzemann et al. [Nature A, 717–722 (1981)] or in EP 183 070, EP 183 071, EP 248 227, EP 263 311. Suitable vectors which can be used for expression in *E. coli* are mentioned, for example, by Sambrook et al. [s.a.] or by Fiers et al. in Procd. 8 th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, for example, in EP 405 370, Procd. Nat. Acad. Sci. USA, 81, 439 (1984) by Yansura and Henner, Meth. Enzym. 185, 199–228 (1990) or EP 207 459.

Either such vectors already carry regulatory elements, for example, promotors or the DNA-sequences of the present invention can be engineered to contain such elements. Suitable promotor-elements which can be used are known in the art and are, for example, for *Trichoderma reesei* the cbh1- [Haarki et al., Biotechnology 7, 596–600 (1989)] or the pki1-promotor [Schindler et al., Gene 130, 271–275 (1993)], for *Aspergillus oryzae* the amy-promotor [Christensen et al., Abstr. 19 th Lunteren Lectures on Molecular Genetics F23 (1987), Christensen et al., Biotechnology 6, 1419–1422 (1988), Tada et al., Mol. Gen. Genet. 229, 301 (1991)], for *Aspergillus niger* the glaA- [Cullen et al., Bio/Technology 5, 369–376 (1987), Gwynne et al., Bio/Technlogy 5, 713–719 (1987), Ward in Molecular Industrial Mycology, Systems and Applications for Filamentous Fungi, Marcel Dekker, New York, 83–106 (1991)], alcA- [Gwynne et al., Bio/Technology 5, 71–719 (1987)], suc1- [Boddy et al. Current Genetics, 24, 60–66 (1993)], aphA- [MacRae et al., Gene 71, 339–348 (1988), MacRae et al., Gene 132, 193–198 (1993)], tpiA- [McKnight et al., Cell 46, 143–147 (1986), Upshall et al., Bio/Technology 5, 1301–1304 (1987)], gpdA- [Punt et al., Gene 69, 49–57 (1988), Punt et al., J. of Biotechnology 17, 19–37 (1991)] and the pkiA-promotor [de Graaff et al., Curr. Genet. 22, 21–27 (1992)]. Suitable promotor-elements which could be used for expression in yeast are known in the art and are, for example, the pho5-promotor [Vogel et al., Molecular and Cellular Biology, 2050–2057 (1989); Rudolf and Hinnen, Proc. Natl. Acad. Sci. 84, 1340–1344 (1987)] or the gap-promotor for expression in Saccharamyces cerevisiae und for *Pichia pastoris*, for example, the aox1-promotor [Koutz et al. Yeast 5, 167–177 (1989); Sreekrishna et al., J. Basic Microbiol. 28, 265–278 (1988)].

Accordingly vectors comprising DNA sequences of the present invention, preferably for the expression of said DNA sequences in bacteria or a fungal or a yeast host and such transformed bacteria or fungal or yeast hosts are also an object of the present invention.

Once such DNA-sequences have been expressed in an appropriate host cell in a suitable medium the encoded phytase can be isolated either from the medium in the case the phytase is secreted into the medium or from the host organism in case such phytase is present intracellularly by methods known in the art of protein purification or described, for example, in EP 420 358. Accordingly a process for the preparation of a polypeptide of the present invention characterized in that transformed bacteria or a host cell as described above is cultured under suitable culture conditions and the polypeptide is recovered therefrom and a polypeptide when produced by such a process or a polypeptide encoded by a DNA sequence of the present invention are also an object of the present invention.

Once obtained the polypeptides of the present invention can be characterized regarding their activity by assays known in the state of the art or as described, for example, by Engelen et al. [J. AOAC Intern. 77, 760–764 (1994)] or in Example 9. Regarding their properties which make the polypeptides of the present invention useful in agriculture any assay known in the art and described for example, by Simons et al. (British Journal of Nutrition 64, 525–540 (1990)], Schöner et al. [J. Anim. Physiol. a. Anim. Nutr. 66, 248–255 (1991)], Vogt [Arch. Geflügelk. 56, 93–98 (1992)], Jongbloed et al. [J. Anim. Sci., 70, 1159–1168 (1992)], Perney et al. [Poultry Science 72, 2106–2114 (1993)], Farrell et al., [J. Anim. Physiol. a. Anim. Nutr. 69, 278–283 (1993), Broz et al., [British Poultry Science 35, 273–280 (1994)] and Düngelhoef et al. [Animal Feed Science and Technology 49, 1–10 (1994)] can be used. Regarding their thermotolerance any assay known in the state of the art and described, for example, by Yamada et al. (s.a.), and regarding their pH and substrate specificity profiles any assays known in the state of the art and described, for example, in Example 9 or by Yamada et al., s.a., can be used.

In general the polypeptides of the present invention can be used without being limited to a specific field of application for the conversion of phytate to inositol and inorganic phosphate.

Furthermore the polypeptides of the present invention can be used in a process for the preparation of compound food or feeds wherein the components of such a composition, for example, feed and other nutrients, are mixed with one or more polypeptides of the present invention. The feed can then be fed to those animals, especially monogastic animals (for example, pigs and poultry). Accordingly compound food or feeds comprising one or more polypeptides of the present invention are also an object of the present invention. One skilled in the art is familiar with their process of preparation. Such compound foods or feeds can further comprise additives or components generally used for such purpose and known in the state of the art.

It is furthermore an object of the present invention to provide a method for the reduction of levels of phytate in animal manure characterized in that an animal is fed such a feed composition in an amount effective in converting phytate contained in the feedstuff to inositol and inorganic phosphate.

BRIEF DESCRIPTION OF THE DRAWINGS

FIG. 1 shows that amino acid sequence of the phytase from *Aspergillus terreus* strain 9A1 and its encoding DNA sequence (SEQ ID NO: 1).

FIG. 2 shows the amino acid sequence of the phytase from *Myceliophthora thermophila* and its encoding DNA sequence (SEQ ID NO: 3).

FIG. 4 shows the amino acid sequence of the phytase from *Talaromyces thermophilus* and its encoding DNA sequence (SEQ ID NO: 5).

FIG. 5 shows the amino acid sequence of the phytase from *Aspergillus fumigatus* and its encoding DNA sequence (SEQ ID NO: 7).

FIG. 6 shows the amino acid sequence of the phytase from *Aspergillus nidulans* and its encoding DNA sequence (SEQ ID NO: 9).

FIG. 7 shows the amino acid sequence of the phytase from the fusion construct of *Aspergillus niger* and *Aspergillus terreus* and its encoding DNA sequence (SEQ ID NO: 11).

FIG. 10 shows DNA sequences of two different PCR fragments obtained and their comparison to relevant parts of the phytase gene of *Aspergillus terreus* 9A1. Relevant parts of the phytase gene of *Aspergillus terreus* 9A1 "9A1" (top lines) (1) and the PCR fragments of *Aspergillus terreus* CBS 116.46 "aterr21" (SEQ ID NO: 13) (bottom lines). Panel A: Fragment obtained with primer pair 8 plus 9 (aterr2 1. Panel B: Fragment obtained with primer pair 10 plus 11 (aterr58 (SEQ ID NO: 14).

FIG. 11: DNA fragments of phytase genes from different fungi obtained by PCR using primers 8 [SEQ ID NO:16] and 9 [SEQ ID NO:16], a: *T. thermophilus* (PCRTth); b: *A. fumigatus* (PCRAfu); c)*A. nidulans* (PCRAni); d:*A. terreus* CBS116.46 (PCRAteCBS89). PCR amplified DNA fragment of *A. terreus* CBS116.46 obtained with primers 10 [SEQ ID NO:17] and 11 (SEQ ID NO:18]: e) (PCRAteCBS1011). The underlined sequence in panel d) shows the position of the Aterr21 primer. The underlined sequence in e) shows the antisense sequence of primer Aterr58. The sequence originating from the primers used to obtain these fragments is not included.

FIG. 13: Clone 1 was obtained by screening partial, size selected HindIII/KpnI libraries (5–7 kb), with the PCRAni probe as outlined herein. Partial sequence of the 6 kb HindIII/KpnI insert of clone 1, including the complete phytase-encoding gene of *A. nidulans*. The intron is indicated by lower-case letters. Potential-N-glycosylation sites are marked with a +. The position of the PCR fragment is indicated by the underlined sequence (SEQ. ID NO: 28).

FIG. 17: Partial sequence of the 5.5 kb EcoRI/SacI insert of Tt29-132, carrying the complete phytase-encoding gene of *T. thermophilus*. The intron is indicated by lower-case letters. Potential N-glycosylation sites are marked with a +. The position of the PCR fragment is indicated by the underlined sequence (SEQ ID NO: 30).

FIG. 19: Partial sequence of the 6 kb BamHI fragment including the complete phytase-encoding gene of *A. fumigatus*. The intron is indicated by lower-case letters. Potential N-glycosylation sites are marked with a +(SEQ ID NO: 32).

FIG. 21: Partial sequence of the 2 kb KpnI insert of clone 227 including the complete phytase-encoding gene of *A. terreus* CBS116.46. The intron is indicated by lower-case letters. Potential N-glycosylation sites are marked with a +. The position of the PCR fragment is indicated by the underlined sequence (SEQ ID NO: 34).

DETAILED DESCRIPTION OF THE INVENTION

EXAMPLES

Deposit of Biological Material

Figure 3A:
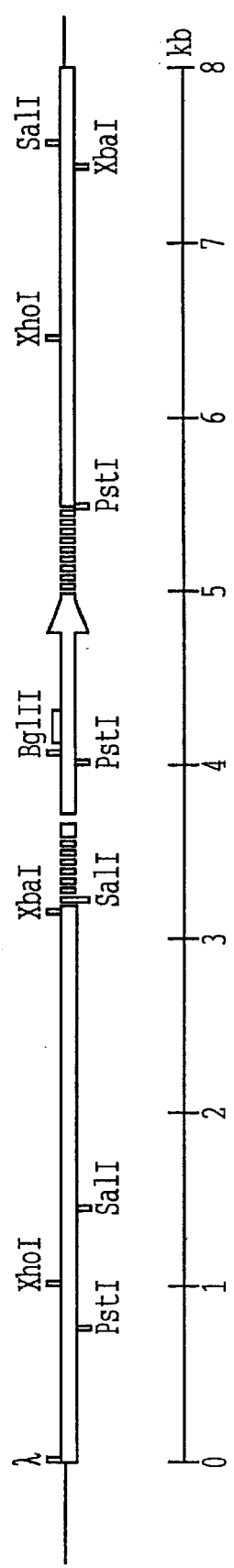
FIG. 3A shows a restriction map for the DNA of *Aspergillus terreus*.
Figure 3B:
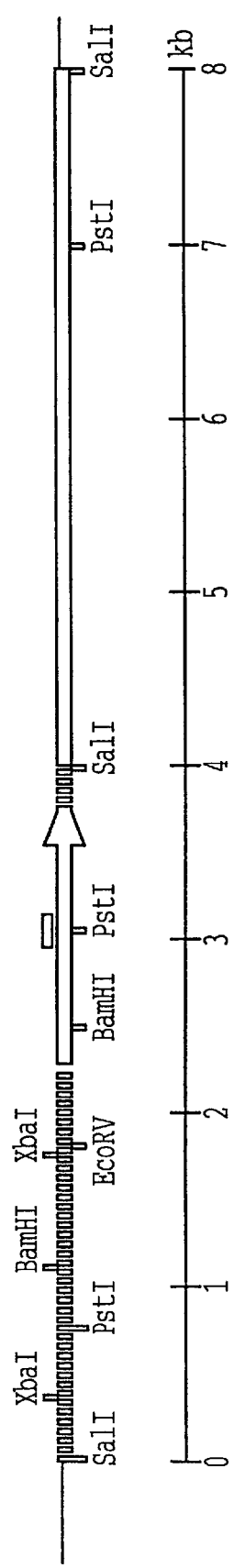
FIG. 3B shows a restriction map for the DNA of *Myceliophthora thermophila*.

The *Aspergillus terreus* CBS 116.46 strain was deposited under the terms of the Budapest Treaty on Mar. 3, 1995 at the Centralbureau voor Schimmel-cultures, Oosterstraat 1, P.O. Box 273, 3740 AG BAARN, The Netherlands, and it was given the deposit No: CBS 220.95.

The *Aspergillus terreus* 9A1 strain was deposited under the terms of the Budapest Treaty on Mar. 17, 1994 at the DSM-DEUTSCHE SAMMLUNG VON, MIKROORGANISMEN UND ZELLKULTUREN, GmbH, Maacheroder Weg 1b, D-38124 Braunschweig, and it was given the deposit No.: DSM 9076.

| Specific media and solutions used | |
|---|---|
| Complete medium (Clutterbuck) | |
| Glucose | 10 g/l |
| —CN solution | 10 ml/l |
| Sodium nitrate | 6 g/l |
| Bacto peptone (Difco Lab., Detroit, MI, USA) | 2 g/l |
| Yeast Extract (Difco) | 1 g/l |
| Casamino acids (Difco) | 1.5 g/l |
| Modified trace element solution | 1 ml/l |
| Vitamin solution | 1 ml/l |
| M3 Medium | |
| Glucose | 10 g/l |
| —CN Solution | 10 ml/l |
| Modified trace element solution | 1 ml/l |
| Ammonium nitrate | 2 g/l |
| M3 Medium - Phosphate | |
| M3 medium except that —CN is replaced with —CNP | |
| M3 Medium - Phosphate + Phytate | |
| M3 Medium - Phosphate with the addition of 5 g/l of $Na_{12}$ Phytate (Sigma #P-3168; Sigma, St. Louis, MO, USA) | |
| Modified trace element solution | |
| CuSO4 | 0.04% |
| FeSO4.7H$_2$O | 0.08% |
| Na$_2$MoO$_4$.2H$_2$O | 0.08% |
| ZnSO$_4$.7H$_2$O | 0.8% |
| B$_4$Na$_2$O$_7$.10H$_2$O | 0.004% |
| MnSO$_4$.H$_2$O | 0.08% |
| Vitamin Solution | |
| Riboflavin | 0.1% |
| Nicotinamide | 0.1% |
| p-amino benzoic acid | 0.01% |
| Pyridoxine/HCl | 0.05% |
| Aneurine/HCl | 0.05% |

-continued

Specific media and solutions used

| | |
|---|---|
| Biotin | 0.001% |
| —CN Solution | |
| | |
| $KH_2PO_4$ | 140 g/l |
| $K_2PO_4.3H_2O$ | 90 g/l |
| KCl | 10 g/l |
| $MgSO_4.7H_2O$ | 10 g/l |
| —CNP Solution | |
| | |
| HEPES | 47.6 g/200 mls |
| KCl | 2 g/200 mls |
| $MgSO_4.7H_2O$ | 2 g/200 mls |

Example 1
Screening Fungi for Phytase Activity

Fungi were screened on a three plate system, using the following three media: "M3" a defined medium containing phosphate); "M3-P" (M3 medium lacking phosphate); and "M3 P+Phytate" (M3 medium lacking phosphate but containing phytate as a sole phosphorus source). Plates were made with agarose to decrease the background level of phosphate.

Fungi were grown on the medium and at the temperature recommended by the supplier. Either spores or mycelium were transferred to the test plates and incubated at the recommended temperature until growth was observed.

The following thermotolerant strains were found to exhibit growth consistent with the production of an extracellular phytase:

*Myceliophthora thermophila* [ATCC 48102]
*Talaromyces thermophilus* [ATCC 20186]
*Aspergillus fumigatus* [ATCC 346251]

Example 2
Growth of Fungi and Dreparation of Genomic DNA

Strains of *Myceliophthora thermophila, Talaromyces thermophilus, Aspergillus fumigatus, Aspergillus nidulans* and *Aspergillus terreus* 9A-1 were grown in Potato Dextrose Broth (Difco Lab., Detroit, Mich., USA) or complete medium (Clutterbuck). *Aspergillus terreus* 9A-1 and *Aspergillus nidulans* have been deposited under the Budapest Treaty for patent purposes at the DSM in Braunschweig, BRD at Mar. 17, 1994 under accession number DSM 9076 and at Feb. 17, 1995 under accession number DSM 9743, respectively.

Genomic DNA was Prepared as Follows:

Medium was innoculated at a high density with spores and grown overnight (O/N) with shaking. This produced a thick culture of small fungal pellets. The mycelium was recovered by filtration blotted dry and weighed. Up to 2.0 g was used per preparation. The mycelium was ground to a fine powder in liquid nitrogen and immediately added to 10 mls of extraction buffer (200 mM Tris/HCl, 250 mM NaCl, 25 mM EDTA, 0.5% SDS, pH 8.5) and mixed well. Phenol (7 mls) was added to the slurry and mixed and then chloroform (3 mls) was also added and mixed well. The mixture was centrifuged (20,000 g) and the aqueous phase recovered. RNase A was added to a final concentration of 250 $\mu$/ml and incubated at 37° C. for 15 minutes. The mixture was then extracted with 1 volume of chloroform and centrifuged (10,000 g, 10 minutes). The aqueous phase was recovered and the DNA precipitated with 0.54 volumes of RT isopropanol for 1 hour at room temperature (RT). The DNA was recovered by spooling and resuspended in water.

The Resultant DNA was Further Purified as Follows:

A portion of the DNA was digested with proteinase K for 2 hrs at 37 °C. and then extracted repeatedly (twice to three times) with an equal volume of phenol/chloroform and then ethanol precipitated prior to resuspension in water to a concentration of approximately 1 $\mu g/\mu l$.

Example 3
Degenerate PCR

PCR was performed essentially according to the protocol of Perkin Elmer Cetus [(PEC); Norwalk, Conn., USA]. The following two primers were used (bases indicated in brackets are either/or):

Phyt 8: 5' ATG GA(C/T) ATG TG(C/T) TC(N) TT(C/T) GA 3' [SEQ ID NO:15]

Degeneracy =32
Tm High =60° C./Tm Low 52° C.

Phyt 9: 5' TT(A/G) CC(A/G) GC(A/G) CC(G/A) TG(N) CC(G/A) TA 3'
[SEQ ID NO:16]
Tm High =70° C./Tm Low 58° C.

A typical Reaction was Performed as Follows:

| | |
|---|---|
| $H_2O$ | 24.5 $\mu l$ |
| 10× PEC GeneAmp Buffer | 5 $\mu l$ |
| GeneAmp dNTP's (10 mM) | 8 $\mu l$ |
| Primer 1 (Phyt 8, 100 $\mu M$) | 5 $\mu l$ |
| Primer 2 (Phyt 9, 100 $\mu M$) | 5 $\mu l$ |
| DNA (~1 $\mu g/\mu l$) | 1 $\mu l$ |
| Taq Polymerase (PEC) | 0.5 $\mu l$ |
| | 50 $\mu l$ |

All components with the exception of the Taq polymerase were incubated at 95 ° C. for 10 minutes and then 50° C. for 10 minutes and then the reaction placed on ice. The Taq polymerase (Amplitaq, F. Hoffmann-La Roche, Basel, CH) was then added and 35 cycles of PCR performed in a Triothermoblock (Biometra, Göttingen, DE) according to the following cycle profile:

95° C./60"
50° C./90"
72° C./120"

An aliquot of the reaction was analyzed on 1.5% agarose gel.

Example 4
Subcloning and Sequencing of PCR Fragments

PCR products of the expected size (approximately 146 bp predicted from the *Aspergillus niger* DNA-sequence) were excised from low melting point agarose and purified from a NACS—PREPAC—column (BRL Life Technologies Inc., Gaithersburg, Md., USA) essentially according to the manufacturer's protocol. The fragment was polyadenylated in 50 $\mu l$ 100 mM Sodiumcacodylate pH6.6, 12.5 mM Tris/HCI pH 7.0, 0.1 mM Dithiothreitol, 125 $\mu g/ml$ bovine serum albumin, 1 mM $CoCl_2$, 20 $\mu MdATP$, 10 units terminal deoxytransferase (Boehringer Mannheim, Mannheim, DE) for 5 minutes at 37° C. and cloned into the p123T vector [Mitchell et al., PCR Meth. App. 2, 81–82 (1992)].

Alternatively, PCR fragments were purified and cloned using the "Sure Clone" ligation kit (Pharmacia) following the manufacturers instructions.

Sequencing was performed on dsDNA purified on a Quiagen-column (Diagen GmbH, Hilden, DE) using the dideoxy method and the Pharmacia T7 kit (Pharmacia, LKB Biotechnology AB, Uppsala, SE) according to the protocol supplied by the manufacturer.

Example 5
Construction and Screening of Lambda Fix II Libraries

The fragments from *Aspergillus terreus* Strain 9A-1 and *Myceliophthora thermophila* were used to probe BamHI and BglII southerns to determine the suitable restriction enzyme to use to construct genomic libraries in the Lambda Fix II vector (Strategene, La Jolla, Calif., USA). Lambda Fix II can only accept inserts from 9–23 kb. Southerns were performed according to the following protocol. Genomic DNA (10 gg) was digested in a final volume of 200 µl. The reaction without enzyme was prepared and incubated on ice for 2 hours. The enzyme (50 units) was added and the reaction incubated at the appropriate temperature for 3 hours. The reaction was then extracted with an equal volume of phenol/chloroform and ethanol precipitated. The resuspended DNA in loading buffer was heated to 65° C. for 15 minutes prior to separation on a 0.7% agarose gel (O/N 30 V). Prior to transfer the gel was washed twice in 0.2 M HCl/10'/room temperature (RT) and then twice in 1 M NaCl/0.4 M NaOH for 15' at RT. The DNA was transferred in 0.4 M NaOH in a capillary transfer for 4 hours to Nytran 13 N nylon membrane (Schleicher and Schuell AG, Feldbach, Zürich, CH). Following transfer the membrane was exposed to UV. [Auto cross-link, UV Stratalinker 2400, Stratagene (La Jolla, Calif., USA)].

The membrane was prehybridized in hybridization buffer [50% formamide, 1% sodium dodecylsulfate (SDS), 10% dextransulfate, 4×SSPE (180 mM NaCl, 10 mM NaH$_2$PO$_4$, 1 mM EDTA, ph 7.4)] for 4 hours at 42° C. and following addition of the denatured probe O/N at 42° C. The blot was washed:

1×SSPE/0.5% SDS/RT/30 minutes
0.1×SSPE/0.1% SDS/RT/30 minutes
0.1×SSPE/0.1% SDS/65° C./30 minutes Results indicate that *Aspergillus terreus* Strain 9A-1 genomic DNA digested with BamHI and *Myceliophthora thermophila* genomic DNA digested with BglII produce fragments suitable for cloning into the lambda Fix II vector.

The construction of genomic libraries of *Aspergillus terreus* Strain 9A-1 and *Myceliophthora thermophila* in Lambda Fix II was performed according to the manufacturer's protocols (Stratagene).

The lambda libraries were plated out on 10 137 mm plates for each library. The plaques were lifted to Nytran 13N round filters and treated for 1 minute in 0.5 M NaOH/1.5 M NaCl followed by 5 minutes in 0.5 M Tris-HCl pH 8.0/1.5 M NaCl. The filters were then treated in 2×SSC for 5 minutes and air dried. They were then fixed with UV (1 minute, UV Stratalinker 2400, Stratagene). The filters were hybridized and washed as above. Putative positive plaques were cored and the phage soaked out in SM buffer (180 mM NaCl, 8 MM MgSO$_4$.7H$_2$O, 20mM Tris/HCl pH 7.5, 0.01% gelatin). This stock was diluted and plated out on 137 mm plates. Duplicate filters were lifted and treated as above. A clear single positive plaque from each plate was picked and diluted in SM buffer. Three positive plaques were picked. Two from *Aspergillus terreus* Strain 9A-1 (9A1λ17 and 9A1λ22) and one from *Myceliophthora thezmophila* (MTλ27).

Example 6
Preparation of Lambda DNA and Confirmation of the Clones

Lambda DNA was prepared from the positive plaques. This was done using the "Magic Lambda Prep" system (Promega Corp., Madison, Wis., USA) and was according to the manufactures specifications. To confirm the identity of the clones, the lambda DNA was digested with PstI and SalI and the resultant blot probed with the PCR products. In all cases this confirmed the clones as containing sequences complementary to the probe.

Example 7
Subcloning and Sequencing of Phytase Genes

DNA from 9A1λ17 was digested with PstI and the resultant mixture of fragments ligated into pBluescript II SK+ (Stratagene) cut with PstI and treated with shrimp alkaline phosphatase (United States Biochemical Corp., Cleveland, Ohio, USA). The ligation was O/N at 16° C. The ligation mixture was transformed into XL-1 Blue Supercompetent cells (Stratagene) and plated on LB Plates containing 0.5 mM isopropyl-β-D-thiogalactopyranoside (IPTG), 40 µg/ml 5-bromo-4-chloro-3-indoyl-β-D-galactopyranoside (Xgal), 50 µg/ml ampicillin.

DNA from 9Aλ17 was digested with BglII and XbaI and the resultant mixture ligated into pBluescript II SK+ digested with BamHI/XbaI. Ligation, transformation and screening were performed as described above.

DNA from MTλ27 was digested with SalI and the resultant mixture of fragments ligated into pBluescript II SK+ cut with SalI and treated with shrimp alkaline phosphatase. The ligation was O/N at 16° C. The ligation mixture was transformed into XL1 Blue Supercompetent cells and plated on LB Plates containing Xgal/IPTG and ampicillin.

Colonies from the above transformations were picked and "gridded" approximately 75 to a single plate. Following O/N incubation at 37° C. the colonies were lifted to a nylon filter ("Hybond-N", Amersham Corp., Arlington Heights, Ill., USA) and the filters treated with 0.5 M NaOH for 3 minutes, 1 M Tris/HCl pH7.5 twice for 1 minute, then 0.5 M Tris/HCl pH7.5/1.5 M NaCl for 5 minutes. The filters were air dried and then fixed with UV (2 minutes, UV Stratalinker 2400, Stratagene). The filters were hybridized with the PCR products of Example 5. Positive colonies were selected and DNA prepared. The subclones were sequenced as previously described in Example 4. Sequences determined are shown in FIG. 1 (FIG. 1) for the phytase from *Aspergillus terreus* strain 9A1 and its encoding DNA sequence, FIG. 2 for the phytase from *Myceliophthora thermophila* and its encoding DNA-sequence, FIG. 3A shows a restriction map for the DNA of *Aspergillus terreus* (wherein the arrow indicates the coding region, and the strips the regions sequenced in addition to the coding region) and 3B for *M. thermophila*, and FIG. 4 for the phytase from *Talaromyces thermophilus* and its encoding DNA sequence, FIG. 5 for the phytase from *Aspergillus fumigatus* and its encoding DNA-sequence and FIG. 6 for the phytase from *Aspergillus nidulans* and its encoding DNA-sequence. The sequences for the phytases and its encoding DNA-sequences from *Talaromyces thermophilus*, *Aspergillus fumigatus* and *Aspergillus nidulans* were obtained in the same way as described for those of *Aspergillus terreus* strain 9A1 and *Myceliophthora thermophila* in Examples 2–7. Bases are given for both strands in small letters by the typically used one letter code abbreviations. Derived amino acid sequences of the phytase are given in capital letters by the typically used one letter code below the corresponding DNA-sequence.

Example 8
Construction of a Chimeric Construct Between *A. niger* and *A. terreus* Phytase DNA-sequences All constructions were made using standard molecular biological procedures as described by Sambrook et al., (1989) (Molecular Cloning, A Laboratory Manual, Cold Spring Harbor Laboratory Press, NY).

The first 146 amino acids (aa) of the *Aspergillus niger* phytase, as described in EP 420 358, were fused to the 320 Cterminal aa of the *Aspergillus terreus* 9A1 gene. A NcoI site was introduced at the ATG start codon when the *A. niger* phytase gene was cloned by PCR. The intron found in the *A. niger* phytase was removed by site directed mutagenesis (Bio-Rad kit, Cat Nr 170–3581; Bio-Rad, Richmond, Calif., USA) using the following primer (wherein the vertical dash indicates that the sequence to its left hybridizes to the 3' end of the first exon and the sequence to its right hybridizes to the 5' end of the second exon):
5'-AGTCCGGAGGTGACT|CCAGCTAGGAGATAC-3' [SEQ ID NO:19].

To construct the chimeric construct of phytases from *A. niger* and *A. terreus* an Eco 47III site was introduced into the *A. niger* coding sequence to aid cloning. PCR with a mutagenic primer (5' CGA TTC GTA gCG CTG GTA G 3') in conjunction with the T3 primer was used to produce a DNA fragment that was cleaved with BamHI and Eco 47III. The BamHI/Eco 47III fragment was inserted into BamHI/Eco 47III cut p9A1Pst (Example 7). FIG. 7 shows the amino acid sequence of the fusion construct and its encoding DNA-sequence.

Example 9

Expression of Phytases

Construction of Expression Vectors

For expression of the fusion construct in *A. niger* an expression cassette was chosen where the fusion gene was under control of the inducible *A. niger* glucoamylase (glaA) promoter.

For the complete *A. terreus* 9A1 gene, expression cassettes with the constitutive *A. nidulans* glyceraldehyde-3-phosphate dehydrogenase (gpdA) promoter were made.

All genes used for expression in *A. niger* carried their own signal sequence for secretion.

Construction of Vector pFPAN1

Figure 8:
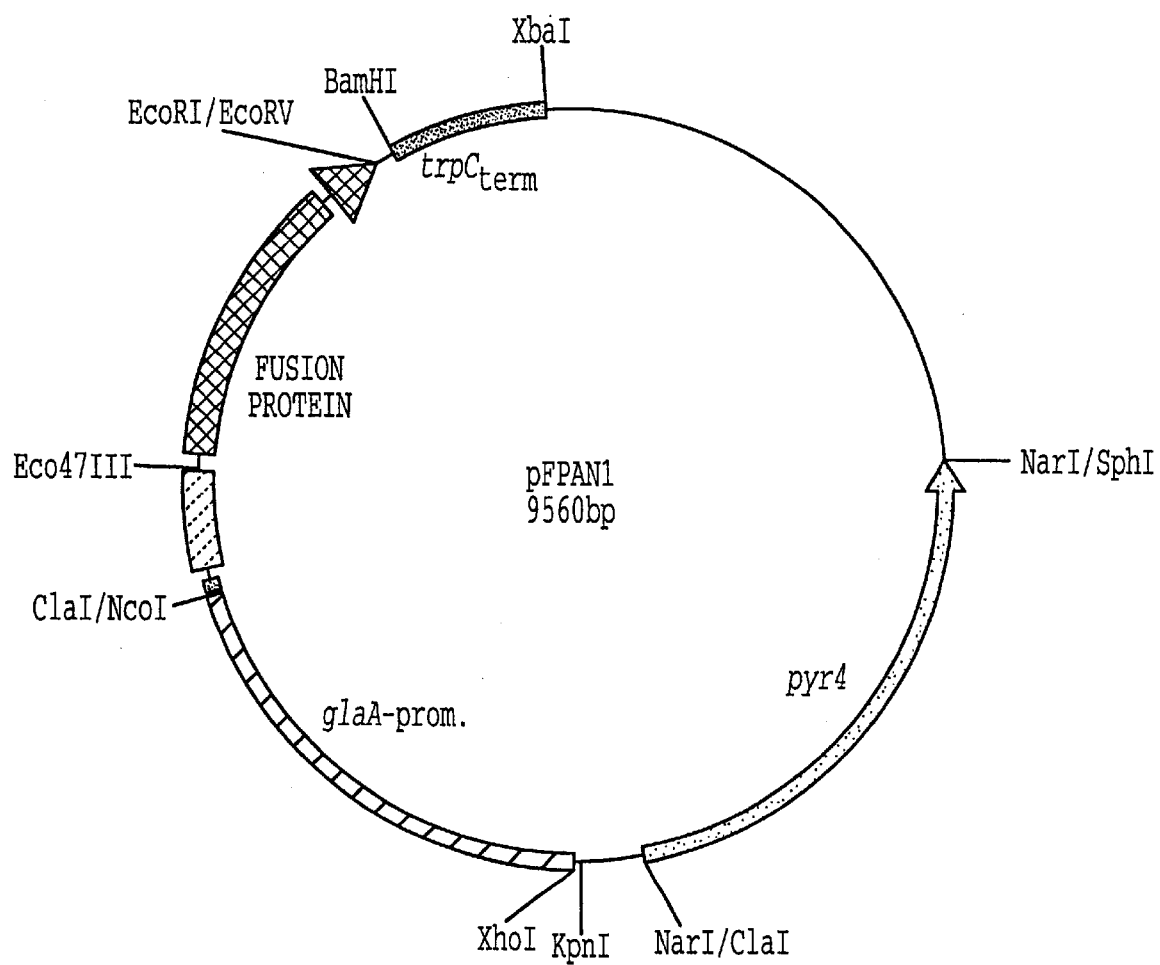
FIG. 8 shows physical map of vector pFPAN1.

The *A. niger* glucoamylase (glaA) promoter was isolated as a 1960 bp XhoI/ClaI fragment from plasmid pDH33 [Smith et al. (1990), Gene 88: 259–262] and cloned into pBluescriptSK+-vector (pBS) [Stratagene, La Jolla, Calif., USA] containing the 710 bp BamHI/XbaI fragment of the *A. nidulans* trpC terminator. The plasmid with the cassette was named pGLAC. The fusion gene, as described in Example 8, was put under control of the *A. niger* glaA promoter by ligating the blunt ended NcoI/EcoRI fragment to the blunt ended ClaI site and the EcoRV site of plasmid pGLAC. The correct orientation was verified by restriction enzyme digests. The entire cassette was transferred as a KpnI/XbaI fragment to pUC19 (New England Biolabs, GmbH, Schwalbach, BRD), that carried the Neurospora crassa pyr4 gene (pUC19-pyr4), a selection marker in uridine auxotrophic Aspergilli, resulting in vector pFPAN1 (see FIG. 8 with restriction sites and coding regions as indicated; crossed out restriction sites indicate sites with blunt end ligation).

Construction of Vector pPAT1

Figure 9:
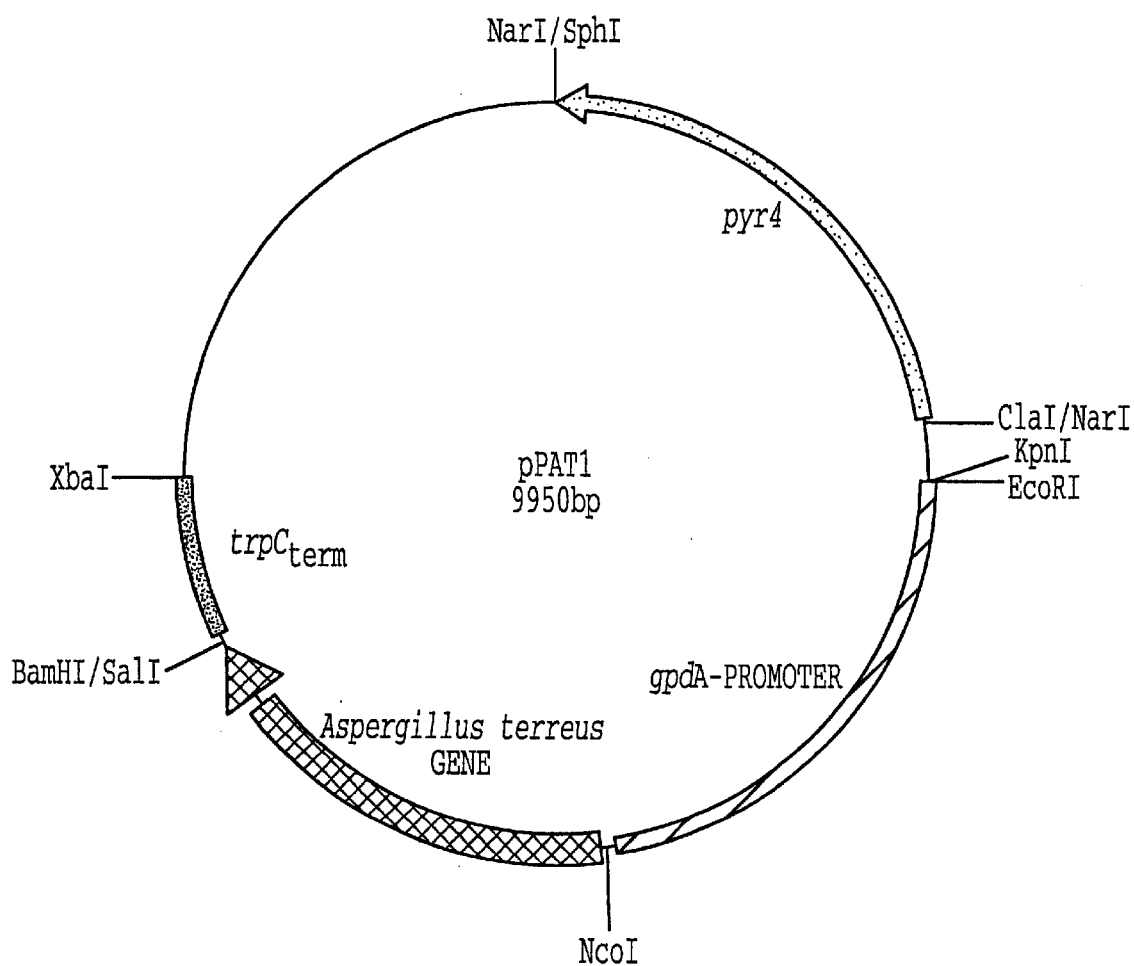
FIG. 9 shows physical map of plasmid pPAT1.

The *A. nidulans* glyceraldehyd-3-phosphate dehydrogenase (gpdA) promoter was isolated as a ~2.3 kb EcoRI/NcoI fragment from plasmid pAN52-1 [Punt et al. (1987), Gene 56: 117–124], cloned into pUC19-NcoI (pUC19 having a SmaI-site replaced by a NcoI-site), reisolated as EcoRI/BamHI fragment and cloned into pBS with the trpC terminator as described above. The obtained cassette was named pGPDN. The *A. terreus* gene was isolated as a NcoI/EcoRI fragment, where the EcoRI site was filled in to create blunt ends. Plasmid pGPDN was cut with BamHI and NcoI. The BamHI site was filled in to create blunt ends. The NcoI/EcoRI(blunt) fragment of the *A. terreus* gene was cloned between the gpda promoter and trpC terminator. The expression cassette was isolated as KpnI/XbaI fragment and cloned into pUC19-pyr4 resulting in plasmid pPAT1 (see FIG. 9; for explanation of abbreviations see legend to FIG. 8).

Expression of the Fusion Protein in *Aspergillus niger*

A) Transformation

The plasmid pFPAN1 was used to transform *A. niger* by using the transformation protocol as described by Ballance et al. [(1983), Biochem. Biophys. Res. Commun 112, 284–289] with some modifications:

YPD medium (1% yeast extract, 2% peptone, 2% dextrose) was inoculated with $10^6$ spores per ml and grown for 24 hours at 30° C. and 250 rpm cells were harvested using Wero-Lene N tissue (No. 8011.0600 Wernli AG Verbandstoffabrik, 4852 Rothrist, CH) and once washed with buffer (0.8 M KCl, 0.05 M $CaCl_2$, in 0.01 M succinate buffer; pH 5.5)

for protoplast preparation only lysing enzymes (SIGMA L2265, St. Louis, Mo., USA) were used the cells were incubated for 90 min at 30° C. and 100 rpm, and the protoplasts were separated by filtration (Wero-Lene N tissue)

the protoplasts were once washed with STC (1 M sorbitol, 0.05 M $CaCl_2$, 0.01 M Tris/HCl pH 7.5) and resuspended in the same buffer 150 μl protoplasts (~$10^8$/ml) were gently mixed with 10–15 μg plasmid DNA and incubated at room temperature (RT) for 25 min polyethylene glycol (60% PEG 4000, 50 mM $CaCl_2$, 10 mM Tris/HCl pH 7.5) was added in three steps, 150 μl, 200 μl and 900 μl, and the sample was further incubated at room temperature (RT) for 25 min 5 ml STC were added, centrifuged and the protoplasts were resuspended in 2.5 ml YGS (0.5% yeast extract, 2% glucose, 1.2 M sorbitol)

the sample was incubated for 2 hours at 30° C. (100 rpm) centrifuged and the protoplasts were resuspended in 1 ml 1.2 M sorbitol the transformed protoplasts were mixed with 20 ml minimal regeneration medium (0.7% yeast nitrogen base without amino acids, 2% glucose, 1 M sorbitol, 1.5% agar, 20 mM Tris/HCl pH 7.5 supplemented with 0.2 g arginine and 10 mg nicotinamide per liter)

the plates were incubated at 30° C. for 3–5 days

B) Expression

Single transformants were isolated, purified and tested for overproduction of the fusion protein. 100 ml M25 medium (70 g maltodextrin (Glucidex 17 D, Sugro Basel, CH), 12.5 g yeast extract, 25 g casein-hydrolysate, 2 g $KH_2PO_4$, 2 g $K_2SO_4$, 0.5 g $MgSO_4.7H_2O$, 0.03 g $ZnCl_2$, 0.02g $CaCl_2$, 0.05 g $MnSO_4.4H_2O$, 0.05 g $FeSO_4$ per liter pH 5.6) were inoculated with $10^6$ spores per ml from transformants FPAN1#11, #13, #16, #E25, #E30 respectively #E31 and incubated for 5 days at 30° C. and 270 rpm. Supernatant was collected and the activity determined. The fusion protein showed the highest activity with phytic acid as substrate at pH 2.5, whereas with 4-nitrophenyl phosphate as substrate it showed two activity optima at pH 2.5 and 5.0 (Table 1).

C) Activity Assay a) Phytic Acid

A 1 ml enzyme reaction contained 0.5 ml dialyzed supernatant (diluted if necessary) and 5.4 mM phytic acid (SIGMA P-3168). The enzyme reactions were made in 0.2 M sodium acetate buffer pH 5.0, respectively 0.2 M glycine buffer pH 2.5. The samples were incubated for 15 min at 37° C. The reactions were stopped by adding 1 ml 15% TCA (trichloroacetic acid).

For the colour reaction 0.1 ml of the stopped sample was diluted with 0.9 ml distilled water and mixed with 1 ml reagent solution (3 volumes 1 M $H_2SO_4$, 1 volume 2.5% $(NH_4)_6Mo_7O_{24}$, 1 volume 10% ascorbic acid). The samples were incubated fot 20 min at 50° C. and the blue color was measured spetrophotometrically at 820 nm. Since the assay is based on the release of phosphate a phosphate standard curve, 11–45 nmol per ml, was used to determine the activity of the samples.

b) 4-Nitrophenyl Phosphate

A 1 ml enzyme reaction contained 100 µl dialyzed supernatant (diluted if necessary) and 1.7 mM 4-nitrophenyl phosphate (Merck, 6850, Darmstadt, BRD). The enzyme reactions were made in 0.2 M sodium acetate buffer pH 5.0, respectively 0.2 M glycine buffer pH 2.5. The samples were incubated for 15 min at 37° C. The reactions were stopped by adding 1 ml 15% TCA.

For the determination of the enzyme activity the protocol described above was used.

TABLE 1

| Trans- | SUBSTRATE | | | |
|---|---|---|---|---|
| | *Phytic Acid | | *4-Nitrophenyl phosphate | |
| formant | pH 5.0 | pH 2.5 | pH 5.0 | pH 2.5 |
| A. niger[1)] | 0.2 | 1 | 1 | 2 |
| FPAN1 #11 | 6 | 49 | 173 | 399 |
| FPAN1 #13 | 2 | 21 | 60 | 228 |
| FPAN1 #16 | 1 | 16 | 46 | 153 |
| FPAN1 #E25 | 3 | 26 | 74 | 228 |
| FPAN1 #E30 | 3 | 43 | 157 | 347 |
| FPAN1 #E31 | 3 | 39 | 154 | 271 |

*Units per ml: 1 unit = 1 µmol phosphate released per min at 37° C.
[1)]not transformed Expression of the *Aspergillus terreus* 9A1 gene in *Aspergillus niger*

*A. niger* NW205 was transformed with plasmid pPAT1 as described above. Single transformants were isolated, purified and screened for overproduction of the *A. terreus* protein. 50 ml YPD medium were inoculated with 106 spores per ml from transformants PAT1#3, #10, #11, #13 and #16 and incubated for 3 days at 30° C. and 270 rpm. Supernatant was collected and the activity determined as described above except that the pH for the enzyme reactions were different. The enzyme showed its main activity at pH 5.5 with phytic acid as substrate and at pH 3.5 with 4-nitrophenyl phosphate as substrate (Table 2).

TABLE 2

| Trans- | SUBSTRATE | | | |
|---|---|---|---|---|
| | *Phytic Acid | | *4-Nitrophenyl phosphate | |
| formant | pH 5.5 | pH 3.5 | pH 5.5 | pH 3.5 |
| A. niger[1)] | 0 | 0 | 0 | 0.1 |
| PAT1 #3 | 10 | 0 | 0.2 | 0.7 |
| PAT1 #10 | 9 | 0 | 0.2 | 0.8 |
| PAT1 #11 | 5 | 0 | 0.1 | 0.5 |

TABLE 2-continued

| Trans- | SUBSTRATE | | | |
|---|---|---|---|---|
| | *Phytic Acid | | *4-Nitrophenyl phosphate | |
| formant | pH 5.5 | pH 3.5 | pH 5.5 | pH 3.5 |
| PAT1 #13 | 9 | 0 | 0.2 | 0.7 |
| PAT1 #16 | 5 | 0 | 0.1 | 0.5 |

*Units per ml: 1 unit = 1 µmol phosphate released per min at 37° C.
[1)]not transformed Example 10

Fermentation of *Aspergillus niger* NW 205 Transformants

A) Transformant FPAN1#11

Preculture medium [30 g maltodextrin (Glucidex 17 D), 5 g yeast extract, 10 g casein-hydrolysate, 1 g $KH_2PO_4$, 0.5 g $MgSO_4.7H_2O$, 3 g Tween 80 per liter; pH 5.5] was inoculated with $10^6$ spores per ml in a shake flask and incubated for 24 hours at 34° C. and 250 rpm.

A 10 liter fermenter was inoculated with the pre-culture to a final dilution of the pre-culture of 1:100. The batch fermentation was run at 30° C. with an automatically controlled dissolved oxygen concentration of minimum 25% ($PO_2 \geq 25\%$). The pH was kept at 3.0 by automatic titration with 5 M NaOH. The medium used for the fermentation was: 35 g maltodextrin, 9.4 g yeast extract, 18.7 g casein-hydrolysate, 2 g $KH_2PO_4$, 0.5 g $MgSO_4.7H_2O$, 2 g $K_2SO_4$, 0.03 g $ZnCl_2$, 0.02 g $CaCl_2$, 0.05 g $MnSO_4.4H_2O$, 0.05 g $FeSO_4$ per liter; pH 5.6.

Enzyme activities reached after 3 days under these conditions were 35 units/ml respectively 16 units/ml at pH 2.5 respectively pH 5.0 with phytic acid as substrate and 295 units/ml respectively 90 units/ml at pH 2.5 respectively pH 5.0 and 4-nitrophenyl phosphate as substrate.

B) Transformant PAT1#11

Preculture, inoculation of the fermenter and the fermentation medium were as described above, except that the pH was kept at 4.5 by automatic titration with 5 M NaOH.

Enzyme activities reached after 4 days under these conditions were 17.5 units/ml at pH 5.5 with phytic acid as substrate and 2 units/ml at pH 3.5 with 4-nitrophenyl phosphate as substrate.

Example 11

Isolation of PCR Fragments of a Phytase Gene of *Asperailus terreus* (CBS 116.46)

Two different primer pairs were used for PCR amplification of fragments using DNA of *Aspergillus terreus* [CBS 116.46]. The primers used are shown in the Table below.

| Fragment amplified | Primers | Oligonucleotide sequences (5' to 3') |
|---|---|---|
| 8 plus 9 about 150 bp | 8 | ATGGA(C/T)ATGTG(C/T)TC(N)TT(C/T)GA [SEQ ID NO:15] Amino acids 254–259: MDMCSF |
| | 9 | TT(A/G)CC(A/G)GC(A/G)CC(G/A)TG(N)CC(A/G)TA [SEQ ID NO:16] Amino acids 296–301: YGHGAG |
| 10 plus 11 about | 10 | TA(C/T)GC(N)GA(C/T)TT(C/T)TC(N)CA(C/T)GA [SEQ ID NO:17] |

-continued

| Fragment amplified | Primers | Oligonucleotide sequences (5' to 3') |
|---|---|---|
| 250 bp | 11 | Amino acids 349–354: YADFSH<br>CG(G/A)TC(G/A)TT(N)AC(N)AG(N)AC(N)C<br>[SEQ ID NO:18]<br>Amino acids 416–422: RVLVNDR |

DNA sequences in bold show the sense primer and in italics the antisense primer. The primers correspond to the indicated part of the coding sequence of the *Aspergillus niger* gene. The combinations used are primers 8 plus 9 and 10 plus 11. The Taq-Start antibody kit from Clontech (Palo Alto, Calif., USA) was used according to the manufacturer's protocol. Primer concentrations for 8 plus 9 were 0.2 mM and for primers 10 plus 11 one mM. Touch-down PCR was-used for amplification [Don, R. H. et al. (1991), Nucleic Acids Res. 19, 4008]. First the DNA was denatured for 3 min at 95° C. Then two cycles were done at each of the following annealing temperatures: 60° C., 59° C., 58° C., 57° C., 56° C., 55° C., 54° C., 53° C., 52° C. and 51° C., with an annealing time of one min. each. Prior to annealing the incubation was heated to 95° C. for one min and after annealing elongation was performed for 30 sec at 72° C. Cycles 21 to 35 were performed as follows: denaturation one min at 95° C., annealing one min at 50° C. and elongation for 30 sec at 72° C.

Two different PCR fragments were obtained. The DNA sequences obtained and their comparison to relevant parts of the phytase gene of *Aspergillus terreus* 9A1 are shown in FIG. 10 [relevant parts of the phytase gene of *Aspergillus terreus* 9A1 "9A1 "(top lines) (1) and the PCR fragments of *Aspergillus terreus* CBS 116.46 "aterr2" (bottom lines). Panel A: Fragment obtained with primer pair 8 plus. 9 (aterr21). Panel B: Fragment obtained with primer pair 10 plus 11 (aterr58). DNA sequences of *Aspergillus terreus* CBS 116.46 (top lines) are compared with those of *Aspergillus terreus* 9A1 (1) (bottom lines). PCR amplifications were performed as described in the legend to Table 4. Panel A: The bold gc sequence (bases 16 plus 17) in the aterr21 fragment could possibly be cg (DNA sequencing uncertainty). Panel B: The N at position 26 of the aterr58 PCR fragment could possibly represent any of the four nucleotides].

Example 12

Cross Hybridizations under Non-stringent and Stringent Washing Conditions

Five mg's of genomic DNA of each strain listed in Table 3 were incubated with 4 units of HindIII or PstI, respectively, per mg of DNA at 37° C. for 4 hours. After digestion, the mixtures were extracted with phenol and DNAs were precipitated with ethanol. Samples were then analyzed on 0.8% agarose gels. DNA-s were transferred to Nytran membranes (Schleicher & Schuell, Keene, N.H., USA) using 0.4M NaOH containing 1M NaCl as transfer solution. Hybridizations were performed for 18 hours at 42° C. The hybridization solution contained 50% formamide, 1% SDS, 10% dextran sulphate, 4×SSPE (1×SSPE=0.18M NaCl, 1 mM EDTA, 10 mM $NaH_2PO_4$, pH 7.4), 0.5% blotto (dried milk powder in $H_2O$) and 0.5 mg salmon sperm DNA per ml. The membranes were washed under non-stringent conditions using as last and most-stringent washing condition incubation for 30 min at room temperature in 0.1×SSPE containing 0.1% SDS. The probes (labeled at a specific activity of around $10^9$ dpm/mg DNA) used were the PCR fragments generated with primers 8 plus 9 (see Example 11) using genomic DNA of *Myceliophthora thermophila; Mycelio. thermo.; Aspergillus nidulans, Asperg. nidul.; Aspergillus fumigatus, Asperg. fumig.,; Aspergillus terreus* 9A1, *Asperg. torrous* 9A1. *Talaromyces thermophilus, Talarom. thermo*. The MT2 genomic probe was obtained by random priming (according to the protocol given by Pharmacia, Uppsala, Sweden) and spans 1410 bp, from the BspEI site upstream of the N-terminus of the *Mycelo. thezmo.* phytase gen to the PvuII site in the C-terminus (positions 2068 is to 3478). The AT2 genomic probe was obtained by random priming and spans 1365 bp, from the ApaI site to the NdeI site of the Auperg. terreus 9A1 phytase gene (positions 491 to 1856). The AN2 DNA probe was obtained by random priming and spans the complete coding sequence (1404 bp) of the *Asperg. niger* gene (EP 420 358). Results are given in Table 3. ["\*" except for weak signal corresponding to a non-specific 20 kb fragment; In case of the very weak cross-hybridization signal at 20 kb seen with DNA from *Aspergillus niger* using the PCR fragment from *Talaromyces thermophilus* this signal is unspecific, since it differs significantly from the expected 10 kb HindIII-fragment, containing the phytase gene; "\*\*" signal due to only particle digest of DNA].

For cross-hybridizations with stringent washing conditions membranes were further washed for 30 min. at 65° C. in 0.1×SSPE containing 0.1% SDS. Results are shown in Table 4 [$^{(1)}$ only the 10.5-kb HindIII fragment is still detected, the.6.5-kb HindIII fragment disappeared (see Table 3)].

TABLE 3

| | PCR Probes | | | | | Genomic Probes | | DNA Probes |
|---|---|---|---|---|---|---|---|---|
| Source of DNA used for cross-hybrization | Band (kb) detected with Probe of Asperg. fumig. | Band (kb) detected with Probe of Asperg. nidul. | Band (kb) detected with Probe of Asperg. terreus 9A1 | Band (kb) detected with Probe of Mycelio. thermo. | Band (kb) detected with Probe of Talarom. thermo. | Band (kb) detected with genomic Probe MT2 of Mycelio. thermo. | Band (kb) detected with genomic Probe AT2 of Asperg. terreus 9A1 | Band (kb) detected with cDNA Probe AN2 of Asperg. niger (control) |
| *Acrophialophora levis* [ATCC 48380] | no | no | no | no | no | 8-kb | no | no |
| *Aspergillus niger* [ATCC 9142] (control) | no | no | no | no | no* | no | no | 10 kb HindIII |
| *Aspergillus terreus* [CBS 116.46] | no | no | 11-kb HindIII | no | no | no | 11-kb HindIII | no |
| *Aspergillus sojae* [CBS 126.59] | no | no | no | no | no* | no | 3.7-kb HindIII | no |
| *Calcarisporiella* | no | no | 10.5-kb | no | no | 10.5-kb | 10.5-kb | no |

TABLE 3-continued

| | PCR Probes | | | | | Genomic Probes | | DNA Probes |
|---|---|---|---|---|---|---|---|---|
| Source of DNA used for cross-hybrization | Band (kb) detected with Probe of Asperg. fumig. | Band (kb) detected with Probe of Asperg. nidul. | Band (kb) detected with Probe of Asperg. terreus 9A1 | Band (kb) detected with Probe of Mycelio. thermo. | Band (kb) detected with Probe of Talarom. thermo. | Band (kb) detected with genomic Probe MT2 of Mycelio. thermo. | Band (kb) detected with genomic Probe AT2 of Asperg. terreus 9A1 | Band (kb) detected with cDNA Probe AN2 of Asperg. niger (control) |
| thermophila [ATCC 22718] | | | HindIII | | | HindIII | HindIII | |
| Chaetomium rectopilium [ATCC 22431] | no | no | no | no | no | >20-kb** HindIII | >20-kb** HindIII | no |
| Corynascus thermophilus [ATCC 22066] | no | no | no | no | no | 10.5-kb HindIII | no | no |
| Humicola sp. [ATCC 60849] | no | no | no | no | no | 9.5-kb HindIII | no | no |
| Mycelia sterilia [ATCC 20350] | no | no | no | 6-kb HindIII | no | 6-kb HindIII | 6-kb HindIII | no |
| Myrococcum thermophilum [ATCC 22112] | no | no | no | no | 4.8-kb HindIII | no | no | no |
| Rhizomucor miehei [ATCC 22064] | no | 3.8-kb HindIII | no | no | no | no | no | no |
| Sporotrichum cellulophilum [ATCC 20494] | no | no | no | 6-kb HindIII 2.1/3.7-kb PstI | no | 6-kb and 10.5-kb HindIII | 6-kb and 10.5-kb HindIII | no |
| Sporotrichum thermophile [ATCC 22482] | no | no | no | 6-kb HindIII 2.1/3.7-kb PstI | 6-kb HindIII | 6-kb HindIII | 6-kb HindIII | no |
| Scytalidium indonesicum [ATCC 46858] | no | no | no | no | no | 9-kb HindIII | no | no |
| Aspergillus fumigatus [ATCC 34625] | 2.3-kb HindIII | no | no | no | no | no | no | no |
| Aspergillus nidulans [DSM 9743] | no | 9.5-kb HindIII | no | no | no | no | 9.5-kb HindIII | no |
| Aspergillus terreus 9A1 [DSM 9076] | no | no | 10.5-kb HindIII | no | 6.5-kb HindIII | 10.5-kb HindIII | 10.5-kb HindIII | no |
| Myceliophthora thermophila [ATCC 48102] | no | no | no | 6.5-kb HindIII | no | 6.5-kb HindIII | 6.5-kb HindIII | no |
| Talaromyces thermophilus [ATCC 20186] | no | no | no | no | 9.5-kb HindIII | no | no | no |

TABLE 4

| Source of DNA used for cross-hybriziation | Probe Asperg. fumig. | Probe Asperg. nidul. | Probe Asperg. terreus 9A1 | Probe Mycelio. thermo. | Probe Talarom. thermo. | Genomic Probe of MT2 Mycelio. thermo. | Genomic Probe of AT2 Asperg. terreus 9A1 | DNA Probe of AN2 Asperg. niger (control) |
|---|---|---|---|---|---|---|---|---|
| Acrophiolophora levis | | | | | | yes | | |
| Aspergillus niger (control) | | | | | | | | yes |
| Aspergillus terreus (CBS 116.46) | | | yes | | | | yes | |
| Calcarisporiella thermophila | | | yes | | | | yes | |
| Chaetomium rectopilium | | | | | | yes | | |
| Corynascus thermophilus | | | | | | yes | | |
| Sporotrichum cellulophilum | | | | yes | | yes | yes[(1)] | |
| Sporotrichum thermophile | | | | yes | | yes | | |
| Aspergillus fumigatus | yes | | | | | | | |
| Aspergillusd nidulans | | yes | | | | | | |
| Aspergillus terreus 9A1 | | | yes | | | | yes | |
| Mycelia sterilia | | | | | | yes | | |
| Myceliophthora thermophila | | | | yes | | yes | | |
| Talaromyces thermophilus | | | | | yes | | | |

The complete phytase encoding genes of Aspergllus nidulans, Talaromyces thermophilus, Aspergillus fumigatus, and Aspergillus terreus (CBS116.46) are provided for in a manner set forth below.

Organisms and growth conditions: Aspergillus nidulans (DSM 9743), Aspergillus fumigatus (ATCC 34625), Aspergillus terreus (CBS 116.46) and Talaromyces thermophilus (ATCC 20186) were grown on potato dextrose broth (Difco Lab., Detroit, Mich., USA) at 28° C. except for T. thermophilus, a thermotolerant fungus, which was grown at 45° C. Transformed E. coli (TG-1) were grown in Luria broth (LB) at 37° C. with 100 μg/ml ampicillin for selection.

Genomic DNA: Fungal mycelium was obtained by incubating potato dextrose medium at a high density with spores O/N (200 rpm) at the temperatures indicated above. Up to 2 grams of the mycelium, obtained by filtration through a Whatmann filter, were used for the isolation of genomic DNA as described in the present application.

DNA amplification: Genomic DNA of the coding regions of the different phytase genes was amplified using PCR on a Gene Amp Kit (Perkin Elmer Cetus) according to the manufacturer's instructions using degenerate primers:

Primer 8: 5' -ATGGA(C/T)ATGTG(C/T)TC(N)TT(C/T) GA-3' [SEQ ID NO:15]
Primer 9: 5'-TT(A/G)CC(A/G)GC (A/G)CC(G/A)TG(N) CC(A/G)TA-3' [SEQ ID NO:16]
Primer 10: 5'-TA(C/T)GC(N)GA(C/T)TT(C/T)TC(N)CA (C/T) GA-3' [SEQ ID NO:17]
Primer 11: 5'-CG(G/A)TC(G/A)TT(N)AC(N)AG(N)AC (N)C-3' [SEQ ID NO:18]

For *T. thermophilus* all components of the reaction, including the primers 8 [SEQ ID NO:15] and 9 [SEQ ID NO:16] at a final concentration of 10 mM, but with the exception of the Taq polymerase, were incubated at 95° C. for 10 min and 50° C. for 1 min before the reaction was placed on ice. The Taq polymerase was then added and 35 cycles of PCR performed according to the following cycle profiles: 60 sec, 95° C./60 sec, 50° C./90 sec, 72° C./120 sec.

For *A. nidulans, A. terreus* CBS116.46 and *A. fumigatus* a "touch-down" PCR with a final primer concentration of 0.2 mM for primers 8 [SEQ ID NO:151 and 9 [SEQ ID NO:16] was performed as described in Don, R. H., Cox, P. T., Wainwright, B. J., Baker, K., Mattick, J. S., "Touchdown" PCR to circumvent spurious priming during gene amplification. Nucleic Acids Res., 19:4008 (1991).]. In the case of *A. terreus* CBS116.46 additional amplifications with primers 10 [SEQ ID NO:17] and 11 [SEQ ID NO:18] at a final concentration of 1 mM were also done. In all "touch-down" reactions first the DNA was denatured for 3 min at 95° C., followed by two cycles at each of the following annealing temperatures: 60° C., 59° C., 58° C., 57° C., 56° C., 55° C., 54° C., 53° C., 52 and 51° C., with an annealing time of one min each. Prior to annealing the incubation was heated to 95° C. for one min and after annealing elongation was performed for 30 sec at 72° C. Cycles 21 to 35 were performed as follows: denaturation one min at 95° C., annealing one min at 50° C. and elongation for 30 sec at 72° C. As template, 1 μg of the genomic DNA was used in a total reaction mixture of 50 μl.

Primers Aterr21, Aterr58, Terr380 and Terr1810 were used to isolate the complete *A. terreus* CBS 116.46 phytase gene by PCR (see results). The *A. terreus* CBS 116.46 specific primer, Aterr21 (5'-CTGTCGCCGTTCTGCGACC TC-3') [SEQ ID NO:20] and Aterr 58 (5'CGGTGCCGTTGTACAGACCCAGC-3') [SEQ ID NO:21] were designed using the nucleotide sequence of the two PCR fragments obtained with primers 8 [SEQ ID NO:15] and 9 [SEQ ID NO:16] and primers 10 [SEQ ID NO:17] and 11 [SEQ ID NO:18] on genomic DNA of *A. terreus* CBS116.46 (see FIG. 11). Primer Terr380 (5'ATGGGCTTTCTTGCCATTGT-3') [SEQ ID NO:22] and Terrl8 1O (5'TCAGAAACAATCCGCCCAAGTT-3') [SEQ ID NO:23] are specific for the 5' and 3' of the coding sequence of the phytase gene of *A. terreus* 9A1.

In all cases an aliquot of the reaction was analysed on 1.5% agarose gel. PCR products of the expected size were excised from the agarose and isolated by centrifugation of the gel slices through siliconized glass wool as described by Heery, D. M., Gannon, F. and Powell, R., A simple method for subcloning DNA fragments from gel slices. Trends. Genet., 6:173 (1990) or using a GENECLEAN Kit (BIO101.Inc.) essentially according to the manufacturer's protocol. The fragment was subsequently cloned 25 into pUC 18 using the Sure-Clone ligation kit (Pharmacia).

Southern blot analysis: Southern hybridization experiments were performed to construct genomic maps to find appropriate DNA fragments carrying the phytase gene. Genomic DNA (3 μg) was digested with the different restriction enzymes as indicated in the legends of the figures and electrophoresed on a 0.75% agarose gel. The transfer to Zeta-Probe blotting membranes (BIO-RAD) was done as described in Southern, E. M., Detection of specific sequences among DNA fraaments separated by gel electrophoresis. J. Mol. Biol., 98:503 (1975). Prehybridization and hybridization was in 7% SDS, 1% BSA (fraction V; Boehringer), 0.5M $Na_2HPO_4$, pH 7.2 at 65° C. Probes derived from PCR products of the respective phytase genes (see FIG. 11) were labeled with ($\alpha$-$^{32}$P)-dGTP (Amersham) by random-priming according to Sambrook, J., Fritsch, E. F., Maniatis, T., Molecular Cloning: a laboratory manual. Second Edition ed. 1989, Cold Spring Harbor N.Y., Cold Spring Harbor Laboratory Press, U.S.A. and used in the hybridization experiments. After hybridization the membranes were washed twice for 5 minutes in 2×SSC., 1% SDS at room temperature and twice for 15 minutes in 0.1% SSC., 0.1% SDS at 65° C. before exposure O/N on Kodak X-Omat AR film.

Library construction: Prior to the partial library construction, Southern blot analysis with a given probe was done in order to identify a specific restriction fragment of interest. Subsequently 10–20 μg of genomic DNA was digested with the appropriate restriction enzymes and electrophoresed on an agarose gel. According to comigrating DNA markers, the region of interest was cut out of the gel, the DNA isolated and subcloned into the pBluescriptII— (KS) vector. Transformation of the ligation mixture into *E. coli* TG-1 cells resulted in partial genomic libraries carrying the fragment of interest. The genomic *A. fumigatus* (NIH stock#5233) Lambda FIXII library was obtained from Stratagene (cat. Nr. 946055). The size of the cloned fragments, generated by partial Sau3AI digestion of genomic DNA were in the range of 9–22 kb, according to the manufacturer.

Screening of genomic libraries: *E. coli* transformants of the partial genomic libraries of *A. nidulans, A. terreus* CBS 116.46 and *T. thermophilus* were screened using the colony lift assay described in Sambrook, J., Fritsch, E. F., Maniatis, T., Molecular Cloning: a laboratory manual. Second Edition ed. 1989, Cold Spring Harbor N.Y., Cold Spring Harbor Laboratory Press, U.S.A. and the appropriate probe (see FIG. 11). The *A. fumigatus* Lambda FIXII library was screened according to the manufacturer's instructions using the DNA fragment PCRAfu as probe. Putative positive plaques were cored and subjected to a second round of purification. A clear single positive plaque was picked and used to make a large scale phage preparation as described in Sambrook, J., Fritsch, E. F., Maniatis, T., Molecular Cloning: a laboratory manual. Second Edition ed. 1989, Cold Spring Harbor N.Y., Cold Spring Harbor Laboratory Press, U.S.A. The analysis of the DNA insert and further subcloning steps are outlined herein.

DNA sequencing: The sequence was determined by the dideoxy chain termination technique described in Sanger, F., Nicklen, S. and Coulson, A. R., DNA sequencing with chain-terminating inhibitors. Proc. Natl. Acad. Sci. USA., 74:5463–5467 (1977) using the Sequenase Kit (United States Biochemical). Both strands were completely sequenced and the sequence analyzed using the GCG sequence analysis software package (Version 8.0) by Genetics Computer, Inc. See Devereux, J., Haeberli, P. and Smithies, O., A comprehensive set of sequence analysis programs for the VAX. Nucleic Acids Res., 12:387–395 (1984).

Cloning fragments of phytase genes by PCR: To have suitable probes for the library screening, specific DNA fragments of the different phytases were obtained by performing PCR on. genomic DNA of the individual fungi using degenerate primers as described above. These degenerate PCR amplifications on genomic DNA with primers 8 [SEQ ID NO:15] and 9 [SEQ ID NO:16] gave discrete bands of about 120 to 130 bp for *A. nidulans, A. fumigatus, T. thermophilus* and about 150 bp for *A. terreus* CBS 116.46. Furthermore amplification with primers 10 [SEQ ID NO:17] and 11 [SEQ ID NO:18] on genomic DNA of *A. terreus* CBS116.46 gave a amplification product of 220 bp. The sequences of these fragments are shown in FIG. 11.

Figure 12:
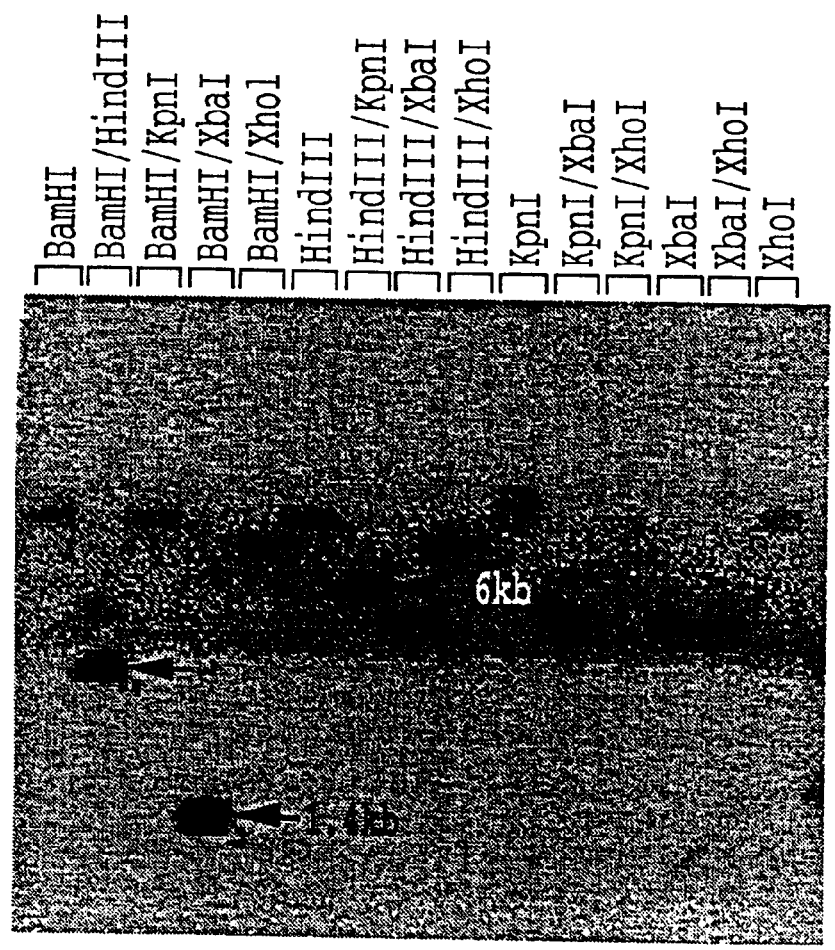
FIG. 12: Southern blot hybridization analysis of *A. nidulans* genomic DNA digested with the restriction enzymes shown on top of each lane and hybridized to the radiolabelled PCRAni probe.

The *A. nidulans* phytase: To identify and isolate DNA fragments carrying the putative phytase gene the PCR fragment PCRAni (FIG. 11) was used to probe a Southern blot carrying chromosomal DNA of *A. nidulans* digested with different restriction enzymes (FIG. 12). The 6 kb HindIII/KpnI fragment hybridizing to the probe seemed the most suitable for cloning Genomic *A. nidulans* DNA was digested with HindIII and KpnI and electrophoresed on an agarose gel. According to comigrating DNA markers, the region of about 5–7 kb was cut out of the gel and the DNA isolated. One positive transformant, clone 1, was chosen and the sequence determined. FIG. 13 shows 1931 nts of the insert [SEQ ID NO:28] carrying the complete phytase gene. The encoded protein [SEQ ID NO:29] consists of 463 amino acids with a theoretical MW of 51785 Da and is interrupted by a single intron with a predicted length of 54 nts and positioned close to the 5' of the gene. In the open reading frame (ORF) upstream of the intron there is one additional potential initiation codon at position 125–127 followed by a putative signal peptide, however when the amino acid sequences of all known phytases are aligned the ATG at position 158 –160 is the most likely translation start site.

Figure 14:
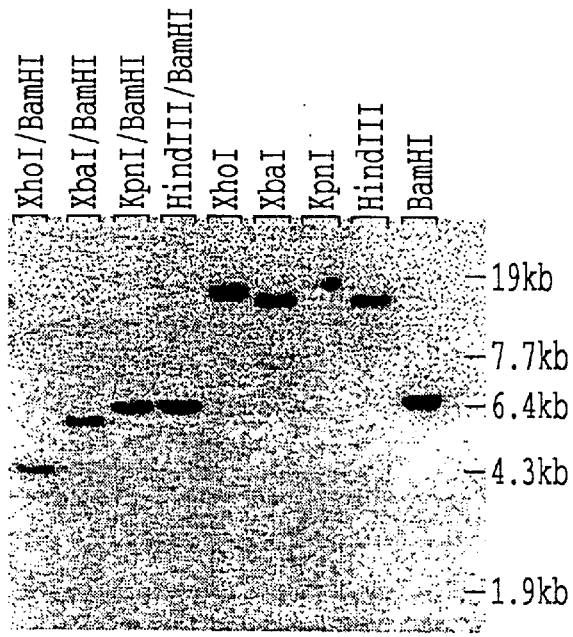
FIG. 14: Southern blot hybridization analysis of *T. thermophilus* genomic DNA digested with the restriction enzymes shown on top of each lane and hybridized to the radiolabelled PCRTth probe. The 4.7 kb XbaI/BamHI fragment was obtained by screening a partial, size selected XbaI/BamHI library (4–5 kb), with the PCRTth probe as outlined herein resulting in clone Tt29.
Figure 15:
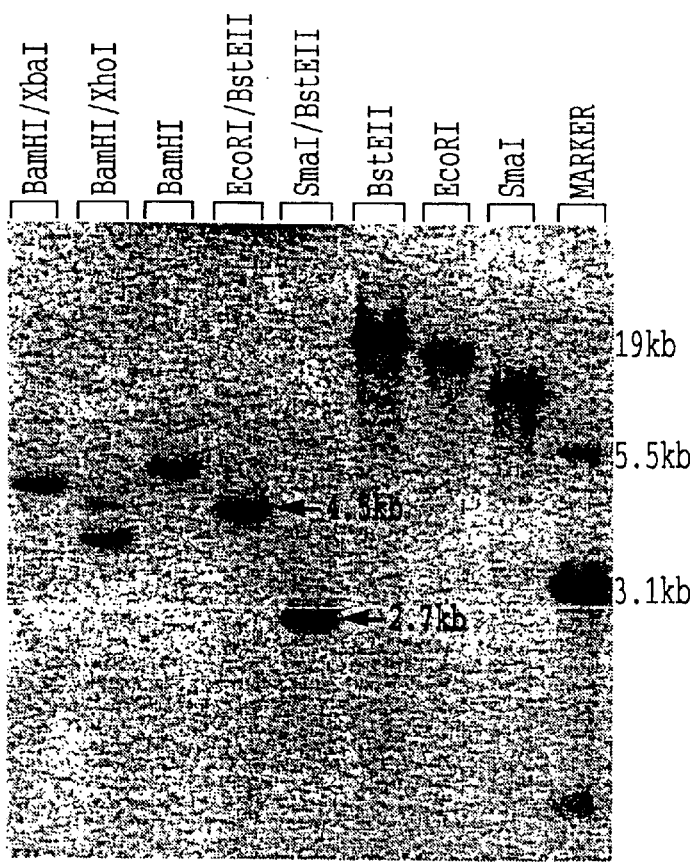
FIG. 15: Southern blot hybridization analysis of *T. thermophilus* genomic DNA digested with the restriction enzymes shown on top of each lane and hybridized to the radiolabelled BamHI/BstEII probe. To get the indicated 4.5 kb EcoRI/BstEII fragment, size selected (4–5 kb) genomic DNA digested with EcoRI and BstEII was isolated and cloned into the BstEII/EcoRI site of clone Tt29 resulting in clone Tt29-132.
Figure 16:
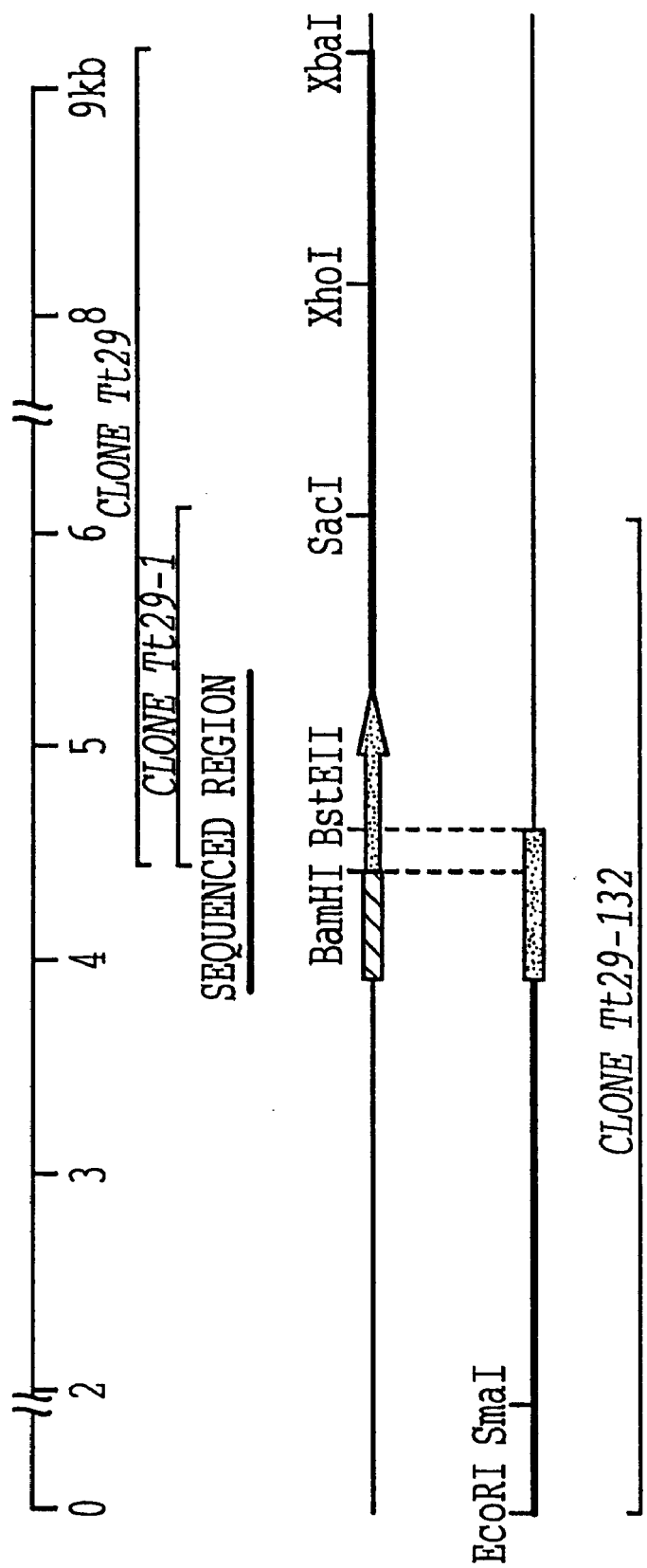
FIG. 16: Map of the region covered by the inserts of clones Tt29, Tt29-1 and Tt29-132 spanning 9.2 kb of the genomic DNA of *T. thermophilus*. The position and direction of the transcription of the phytase gene is indicated.

The *T. themchiwus* phytase: A partial library with BamHI/XbaI fragments of about 4.7 kb was constructed based on the Southern blot analysis results with genomic DNA of *T. thermophilus* (FIG. 14). One positive transformant, clone Tt29, was chosen and sequencing reactions with primer and reverse primer performed. Sequencing data showed that the BamHI restriction site was present within the phytase gene and therefore only part of the complete gene had been isolated. Comparison of the amino acid sequence to known phytase proteins predicted that we had cloned the C-terminus of the putative phytase gene. To get the missing N-terminus a chromosome walking approach was taken using 5' end of clone Tt29 (a 370 bp BamHI-BstEII fragment) as probe, to hybridize to *T. thermophilus* genomic DNA double digested with BstEII and a number of other restriction enzymes (FIG. 15). The 4.5 kb EcoRI/BstEII DNA fragment identified by the probe was the most appropriate for cloning. Genomic DNA digested with EcoRI and BstEII and having a size between 4 and 5 kb was isolated and subcloned into the EcoRI and BstEII sites of plasmid Tt29–1. Plasmid Tt29-1 is a shorter variant of construct Tt29, and was obtained by deleting a 3.6 kb. SacI fragment. This reduction of the plasmid size was done to avoid instability problems which potentially could arise when cloning the 4.5 kb EcoRI-BstEII fragment into the plasmid Tt29, already containing a 4.7 kb DNA insert. Transformant carrying the Tt29-132 construct were identified by hybridization to the BamHI-BstEII DNA probe. One positive clone carrying the EcoRI-SacI insert of approx. 5.5 kb was chosen and the phytase sequence determined. FIG. 16 shows a linear map of the position of the insert of the plasmid clones Tt29, Tt29-1 and Tt29-132.

The 1845 nts of the insert Tt29–132 [SEQ ID NO:30] are shown in FIG. 17. The phytase gene of *T. thermophilus* encodes, interrupted by a single intron located similar to the above mentioned phytase genes, a protein [SEQ ID NO:31] of 466 amino acids. The theoretical molecular weight is 51450 Da.

One additional potential initiation codon is present upstream at position 236–238 followed by a putative signal sequence. However based on amino acid homology comparisons to the other phytases the ATG at position 288–290 is the most likely translation initiation site.

Figure 18:
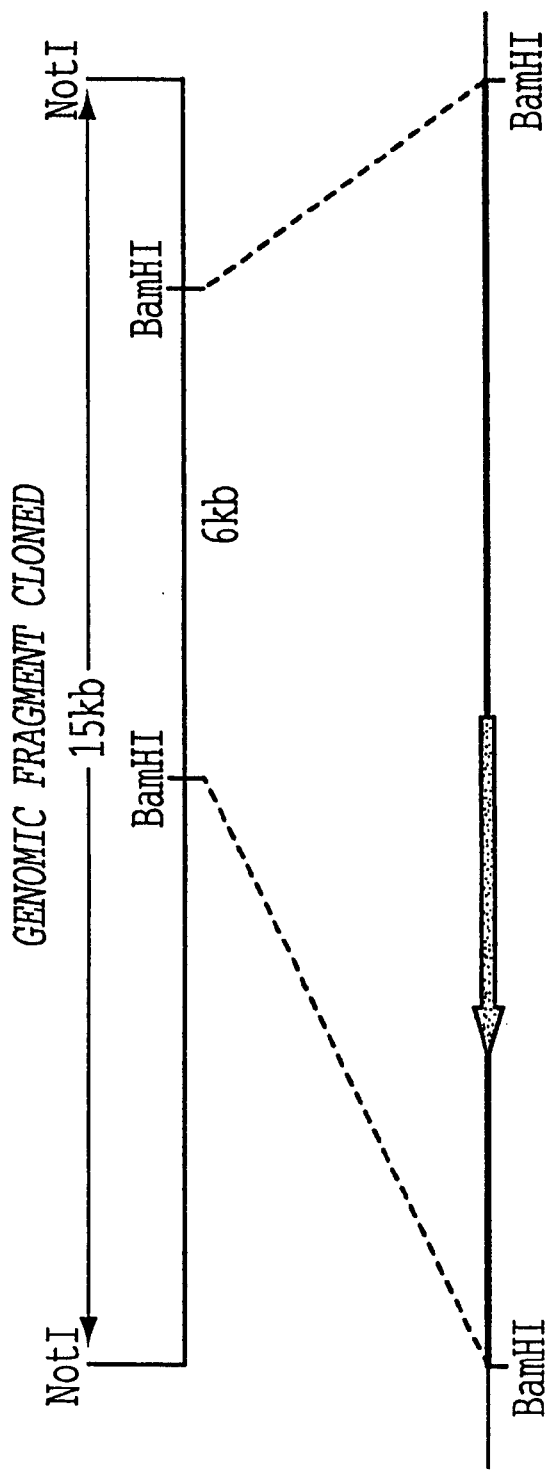
FIG. 18: Map of 15 kb NotI insert of the positive Lambda clone isolated from the FIXII *A. fumigatus* genomic DNA library containing the phytase gene. The position of the subcloned 6 kb BamHI fragment containing the the phytase gene and the direction of the transcription are indicated.

The *A. fumigatus* phytase: Screening of $5.3 \times 10^6$ plaques of the *A. fumigatus* FIXII library with the probe PCRAfu gave 115 hybridizing plaques. Two plaques were picked and subjected to a second round of purification. Bacteriophage DNA of the two candidates was isolated and digested with NotI. The Lambda clone having the largest insert (approx. 15 kb) was further mapped by restriction analysis and genomic Southern. FIG. 18 shows the position of the BamHI fragment within the insert of the bacteriophage lambda clone. The 6 kb BamHI fragment giving a strong signal with the above mentioned probe was isolated, subcloned and part of the sequence encoding the phytase gene was determined. FIG. 19 shows 1571 nts of the insert [SEQ ID NO:32] carrying the complete phytase gene. One single intron of 56 nts is found close to the 5' of the gene. This is in accordance with the aforementioned phytase genes. The enzyme. consists of 465 amino acids [SEQ ID NO:33] with a theoretical MW of 50704 Da.

Figure 20:
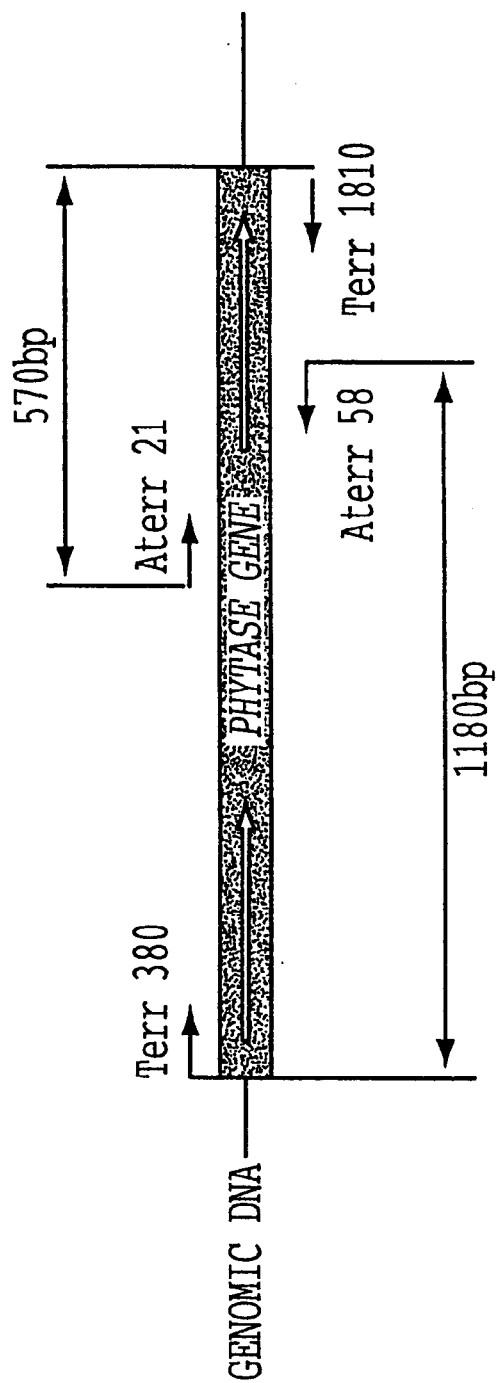
FIG. 20: Map of the *A. terreus* strain 9A1 phytase showing the position of the different primers used for PCR amplifications on genomic DNA of *A. terreus* CBS116.46. The expected size of the two PCR products are also indicated.

The *A. terres* CBS 116.46 phytase: Based on the high sequence identity seen between both strains of *A. terreus*, 9A1 and CBS 116.46, we tried to isolate the phytase gene of the latter strain by PCR, using primers derived from the 5' and 3' of the *A. terreus* 9A1 sequence (Terr 380 [SEQ ID NO:22] and Terr 1810 [SEQ ID NO:23] ) and two internal primers (Aterr 21 [SEQ ID NO:20] and Aterr 58 [SEQ ID NO:21]) derived from the *A. terreus* CBS 116.46 DNA fragments described in FIG. 11. FIG. 20 outlines the position of the primers on the phytase gene of *A. terreus* strain 9A1 and the expected amplification products. Only primer Atterr 21 [SEQ ID NO:20] and Terr 1810 [SEQ ID NO:23] gave a product with an expected size of about 570 bp. The PCR fragment was cloned into the SmaI site of pUC18, resulting in plasmid pUC18–569. Sequencing of the insert confirmed that we had cloned the C-terminus of the phytase gene. The missing N-terminus of the gene was cloned basically as described for the other phytases. Southern blot analysis of genomic DNA of *A. terreus* CBS-116.46, with the 570 bp *A. terreus* CBS116.46 DNA piece as probe, identified a KpnI/KpnI fragment of 2 kb carrying the complete phytase gene. The region of about 2 kb was isolated and used to construct a partial genomic library. One *E. coli* transformant, clone 227, hybridizing to the probe was then used for further analysis. FIG. 21 shows 1567 nts of the insert [SEQ ID NO:34]. The encoded phytase has 466 amino acids [SEQ ID NO:35] and a theoretical molecular weight of 51054 Da.

The phytases from *Aspergillus fumigatus, A. nidulans, A. terreus* 9A1*, A. terreus* CBS, and *Myceliophthora thermophila* were overexpressed in *A. niger* or *Hansenula polymozpha* and purified to apparent homogeneity. After removal of the cells, the clear culture supernatant was concentrated by ultrafiltration and subjected to buffer exchange on a Fast Desalting Column HR 10/10

Figure 22:
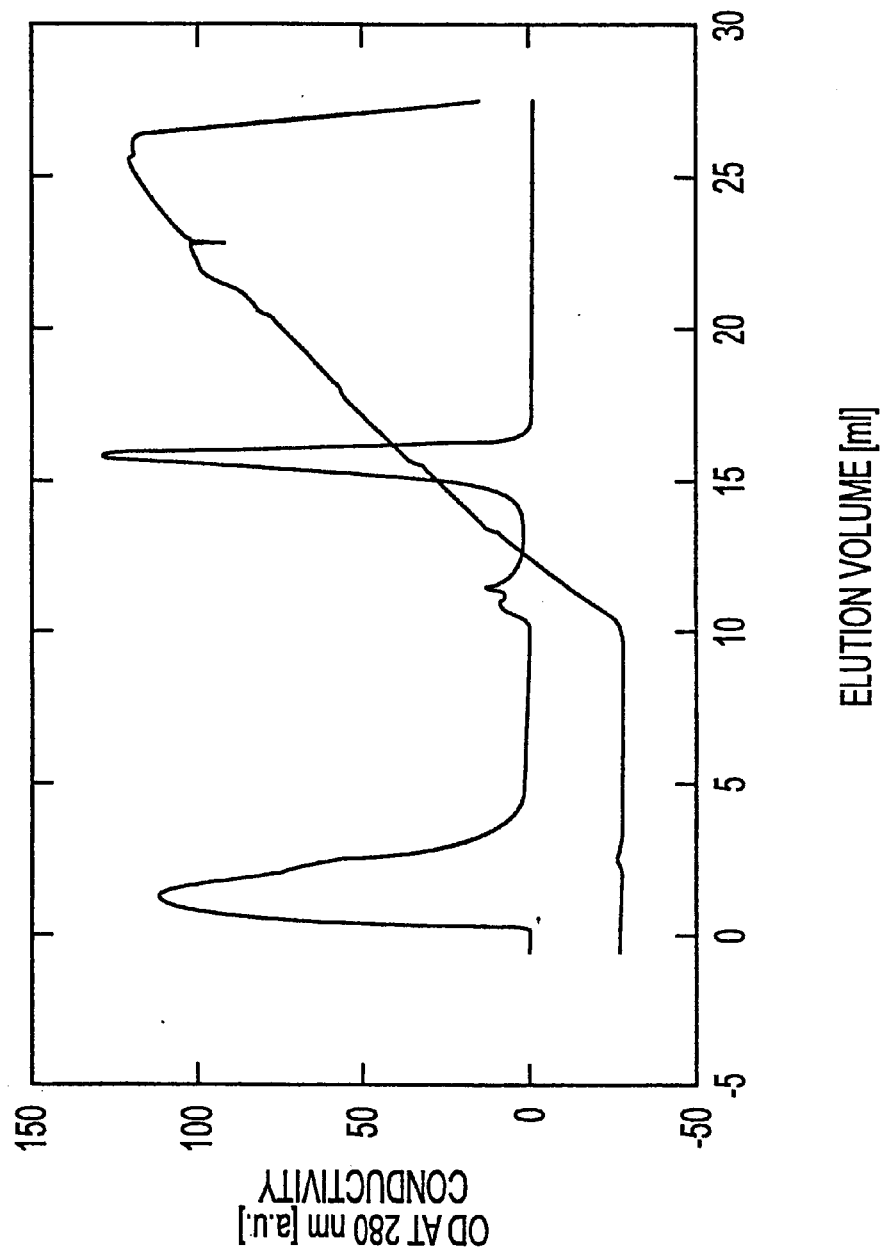
FIG. 22: Purification of *A. fumigatus* phytase. The $OD_{280}$ and conductivity traces are shown. All contaminants eluted either in the break-through fractions or early in the gradient (around 10 ml). *A. fumigatus* phytase was eluted as a symmetrical and homogeneous peak at approx. 15 ml.

(Pharmacia). Final purification was achieved by cation exchange chromatography on either a Mono S HR 5/5 (Pharmacia) or a Poros HS/M column (PerSeptive Biosystems) in the case of A. fumigatus phytase (FIG. 22). The sample was loaded in a buffer containing 10 mM sodium acetate, pH 5.0. A. fumigatus phytase was eluted ith a linear gradient from 10 mM sodium acetate, pH 5.0 to 10 mM sodium acetate, 1 M NaCl, pH 5.0. Anion exchange chromatography on a Poros HQ/M column (PerSeptive Biosystems) was used in the case of the other phytases.

In order to corroborate the identities of the purified proteins, samples were separated by SDS-PAGE and blotted onto PVDF membranes (Immobilon-P$^{SQ}$, Millipore). N-terminal sequencing of the proteins was done by automated Edman degradation on an Applied Biosystems 494A sequencer with on-line microbore phenylthiohydantoin detection. The results of the N-terminal sequencing are set forth in Table 5.

TABLE 5

N-terminal sequences of the purified proteins

| | |
|---|---|
| Aspergillus fumigatus phytase: | SKSXDTVDLGY |
| Aspergillus nidulans phytase: | VVQNHSX |
| | NHSXNTA |
| Aspergillus terreus 9A1 phytase: | SDXNSVDHGY |
| Myceliophthora thermophila phytase: | SESRP |

For the determination of the specific activity of the respective proteins, protein concentration was calculated from $OD_{280}$ according to the theoretical absorption calculated from the amino acid sequences. Phytase activity was measured in an assay mixture containing 0.5% phytic acid (~5 mM), 200 mM sodium acetate, pH 5.0. After a 15 min-incubation period at 37° C., the reaction was stopped by addition of an equal volume of 15% TCA. The liberated phosphate ions were quantified by mixing 100 µl of the assay mixture with 900 µl $H_2O$ and 1 ml of 0.6 M $H_2SO_4$, 2% ascorbic acid and 0.5% ammonium molybdate. Standard solutions of potassium phosphate were used as reference. One unit (U) is defined as the amount of protein liberating 1 µmol of inorganic phosphate per minute at 37° C.

TABLE 6

Specific activities (in U/mg protein) of the purified phytases

| | | |
|---|---|---|
| Aspergillus fumigatus phytase: | 25.1 ± 5.1 | (n = 16) |
| Aspergillus nidulans phytase: | 28.6 ± 4.4 | (n = 7) |
| Aspergillus terreus 9A1 phytase: | 141.6 ± 7.1 | (n = 3) |
| Aspergillus terreus CBS phytase: | 203.8 ± 12.2 | (n = 5) |
| Myceliophthora thermophila phytase: | 41.8 ± 4.4 | (n = 3) |

Figure 23:
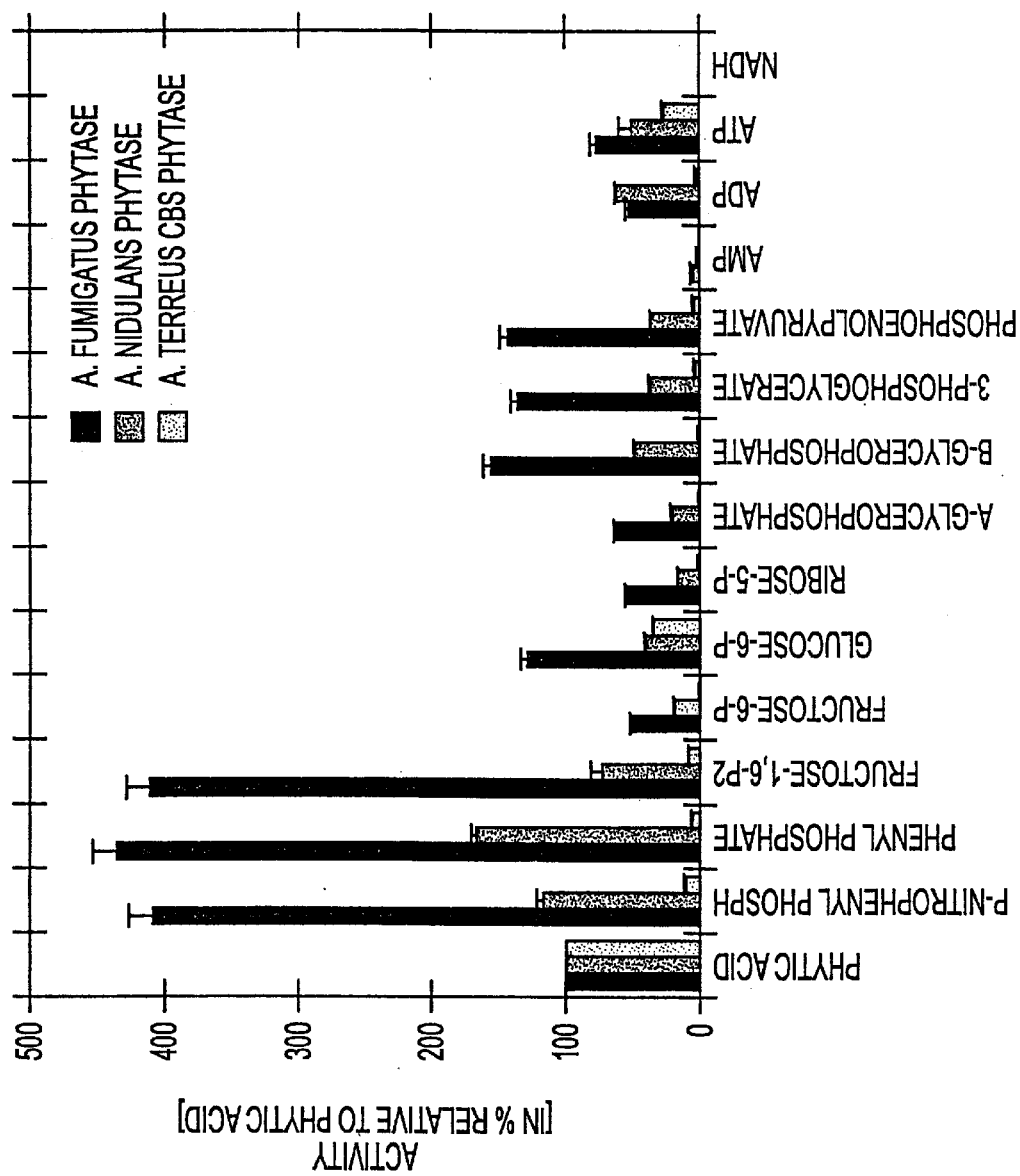
FIG. 23: Substrate specificities of purified *A. fumigatus, A. nidulans* and *A. terreus* CBS phytase. The activities found with these substrates were expressed relative (in %) to the activity found with phytic acid.

For the investigation of the substrate specificities of A. fumigatus, A. nidulans and A. terreus CBS phytase, phytic acid was replaced in the activity assay by 5 mM-concentrations of pnitrophehyl phosphate, phenyl phosphate, fructose 1,6-diphosphate, fructose 6-phosphate, glucose 6-phosphate, ribose 5-phosphate, α-glycerophosphate, β-glycerophosphate, 3-phosphoglycerate, AMP, ADP, ATP, or NADH. The activities found with these substrates were expressed relative (in %) to the activity found with phytic acid. The results of. the substrate specificities are set forth in FIG. 23.

What is claimed is:

1. A purified and isolated polynucleotide comprising SEQ ID NO: 32 or a polynucleotide that hybridizes to the complete complementary strand of SEQ ID NO: 32 under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS, wherein the polynucleotide that hybridizes to the complement of SEQ ID: 32 encodes a polypeptide having phytase activity.

2. A purified and isolated polynucleotide according to claim 1 wherein the polynucleotide that hybridizes to SEQ ID NO: 32 is derived from a fungus, wherein the fungus is selected from the group consisting of *Acrophialophora levis, Aspergillus terreus, Aspergillus fumigatus, Aspergillus nidulans, Aspergillus sojae, Calcarisporiella thermophila, Chaetomium rectopilium, Corynascus thermophilus,* Humicola sp., *Mycelia sterilia, Myrococcum thermophilum, Myceliophthora thermophila, Rhizomucor miehei, Sporotrichum cellulophilum, Sporotrichum thermophile, Scytalidium indonesicum* and *Talaromyces thermophilus.*

3. The purified and isolated polynucleotide of claim 2 wherein the fungus is selected from the group consisting of *Acrophialophora levis, Aspergillus fumigatus, Aspergillus nidulans, Aspergillus terreus, Calcarisporiella thermophila, Chaetomium rectopilium, Corynascus thermophilus, Sporotrichum cellulophilum, Sporotrichum thermophile, Mycelia sterilia, Myceliophthora thermophila* and *Talaromyces thermophilus.*

4. The purified and isolated polynucleotide of claim 3 wherein the fungus is selected from the group consisting of *Aspergillus terreus, Myceliophthora thermophila, Aspergillus fumigatus, Aspergillus nidulans* and *Talaromyces thermophilus.*

5. The purified and isolated polynucleotide of claim 4 wherein the fungus is *Aspergillus fumigatus.*

6. A purified and isolated polynucleotide derived from *Aspergillus fumigatus* which encodes a polypeptide having phytase activity selected from the following:

(a) SEQ ID NO: 32;

(b) a polynucleotide that hybridizes to the complete complementary strand of SEQ ID NO: 32 under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS; and (c) a polynucleotide which, because of the degeneracy of the genetic code, does not hybridize with the complete complementary strand of the polynucleotides of (a) or (b) under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS but which codes for polypeptides having exactly the same amino acid sequences as the polypeptides encoded by the polynucleotides of (a) or (b).

7. A purified and isolated polynucleotide which encodes a polypeptide having phytase activity wherein the polynucleotide is a product of a PCR reaction with DNA derived from *Asperqillus fumigatus* and the following pair of PCR primers: SEQ ID NO:15 as the sense primer and SEQ ID NO:16 as the anti-sense primer.

8. The purified and isolated polynucleotide of claim 1 wherein the polynucleotide consists of SEQ ID NO: 32.

9. A vector comprising SEQ ID NO: 32 or a polynucleotide that hybridizes to the complete complementary strand of SEQ ID NO: 32 under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS, wherein the polynucleotide that hybridizes to the complement of SEQ ID NO: 32 encodes a polypeptide having phytase activity.

10. A vector according to claim 9 wherein the polynucleotide that hybridizes to SEQ ID NO: 32 is derived from a fungus, wherein the fungus is selected from the group consisting of *Acrophialophora levis, Aspergillus terreus, Aspergillus fumigatus, Aspergillus nidulans, Aspergillus sojae, Calcarisporiella thermophila, Chaetomium rectopilium, Corynascus thermophilus,* Humicola sp., *Mycelia sterilia, Myrococcum thermophilum, Myceliophthora thermophila, Rhizomucor miehei, Sporotrichum cellulophilum, Sporotrichum thermophile, Scytalidium indonesicum* and *Talaromyces thermophilus.*

11. The vector of claim 10 wherein the fungus is selected from the group consisting of *Acrophialophora levis, Aspergillus fumigatus, Aspergillus nidulans, Aspergillus terreus, Calcarisporiella thermophila, Chaetomium rectopilium, Corynascus thermophilus, Sporotrichum cellulophilum, Sporotrichum thermophile, Mycelia sterilia, Myceliophthora thermophila* and *Talaromyces thermophilus.*

12. The vector of claim 11 wherein the fungus is selected from the group consisting of *Aspergillus terreus, Myceliophthora thermophila, Aspergillus fumigatus, Aspergillus nidulans,* and *Talaromyces thermophilus.*

13. The vector of claim 12, wherein the fungus is *Aspergillus fumigatus.*

14. A vector comprising a polynucleotide derived from *Aspergillus fumigatus*, which encodes a polypeptide having phytase activity selected from the following:
  (a) SEQ ID NO: 32;
  (b) a polynucleotide that hybridizes to the complete complementary strand of SEQ ID NO: 32 under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS; and
  (c) a polynucleotide which, because of the degeneracy of the genetic code, does not hybridize with the complete complementary strand of the polynucleotides of (a) or (b), under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS but which codes for polypeptides having exactly the same amino acid sequences as the polypeptides encoded by the polynucleotides of (a) or (b).

15. A vector comprising a polynucleotide which encodes a polypeptide having phytase activity wherein the polynucleotide is a product of a PCR reaction with DNA derived from *Asiergillus fumigatus* and the following pair of PCR primers: SEQ ID NO:15 as the sense primer and SEQ ID NO:16 as the anti-sense primer.

16. The vector of claim 9 suitable for the expression of the polynucleotide in a bacterial host cell, a fungal host cell or a yeast host cell.

17. The vector of claim 9 wherein the polynucleotide consists of SEQ ID NO: 32.

18. A host cell transformed by a SEQ ID NO: 32 or a polynucleotide that hybridizes to the complete complementary strand of SEQ ID NO: 32 under the following conditions: hybridization at 42° C. for 18 hours in a hybridization solution containing 4×SSPE, 50% formamide, 1% SDS, 10% dextran sulfate, 0.5% blotto, and 0.5 mg/ml salmon sperm DNA, wash for 30 minutes at room temperature in 0.1×SSPE containing 0.1% SDS, wherein the polynucleotide that hybridizes to the complement of SEQ ID NO: 32 encodes a polypeptide having phytase activity.

19. The transformed host cell of claim 18 wherein the host cell is a bacterial, fungal or yeast host cell.

20. The transformed host cell of claim 19 wherein the polynucleotide consists of SEQ ID NO: 32.

21. A host cell transformed by a polynucleotide which encodes a polypeptide having phytase activity wherein the polynucleotide is a product of a PCR reaction with DNA derived from *Aspergillus fumigatus* and the following pair of PCR primers: SEQ ID NO:15 as the sense primer and SEQ ID NO:16 as the anti-sense primer.

22. A host cell according to claim 18 wherein the polynucleotide that hybridizes to the complement of SEQ ID NO: 32 is derived from a fungus, wherein the fungus is selected from the group consisting of *Acrophialophora levis, Aspergillus terreus, Aspergillus fumigatus, Aspergillus nidulans, Aspergillus sojae, Calcarisporiella thermophila, Chaetomium rectopilium, Corynascus thermophilus,* Humicola sp., *Mycelia sterilia, Myrococcum thermophilum, Myceliophthora thermophila, Rhizomucor miehei, Sporotrichum cellulophilum, Sporotrichum thermophile, Scytalidium indonesicum* and *Talaromyces thermophilus.*

23. The transformed host cell according to claim 22, wherein the fungus is selected from the group consisting of *Acrophialophora levis, Aspergillus fumigatus, Aspergillus nidulans, Aspergillus terreus, Calcarisporiella thermophila, Chaetomium rectopilium, Corynascus thermophilus, Sporotrichum cellulophilum, Sporotrichum thermophile, Mycelia sterilia, Myceliophthora thermophila* and *Talaromyces thermophilus.*

24. The transformed host cell according to claim 23, wherein the fungus is selected from the group consisting of *Aspergillus terreus, Myceliophthora thermophila, Aspergillus fumigatus, Aspergillus nidulans* and *Talaromyces thermophilus.*

* * * * *